United States Patent
Firminger et al.

(10) Patent No.: US 9,886,729 B2
(45) Date of Patent: Feb. 6, 2018

(54) COMPUTATIONAL SYSTEMS AND METHODS FOR HEALTH SERVICES PLANNING AND MATCHING

(75) Inventors: Shawn P. Firminger, Redmond, WA (US); Jason Garms, Redmond, WA (US); Roderick A. Hyde, Redmond, WA (US); Edward K. Y. Jung, Bellevue, WA (US); Chris Demetrios Karkanias, Sammamish, WA (US); Eric C. Leuthardt, St. Louis, MO (US); Royce A. Levien, Lexington, MA (US); Richard T. Lord, Tacoma, WA (US); Robert W. Lord, Seattle, WA (US); Mark A. Malamud, Seattle, WA (US); John D. Rinaldo, Jr., Bellevue, WA (US); Clarence T. Tegreene, Bellevue, WA (US); Kristin M. Tolle, Redmond, WA (US); Lowell L. Wood, Jr., Bellevue, WA (US)

(73) Assignee: Gearbox, LLC, Bellevue, WA (US)

( * ) Notice: Subject to any disclaimer, the term of this patent is extended or adjusted under 35 U.S.C. 154(b) by 0 days.

(21) Appl. No.: 12/658,256

(22) Filed: Feb. 4, 2010

(65) Prior Publication Data

US 2010/0305963 A1 Dec. 2, 2010

Related U.S. Application Data

(63) Continuation-in-part of application No. 12/381,377, filed on Mar. 10, 2009, now abandoned, and a
(Continued)

(51) Int. Cl.
*G06Q 50/22* (2012.01)
*G06F 19/00* (2011.01)
*G06Q 10/10* (2012.01)

(52) U.S. Cl.
CPC ......... *G06Q 50/22* (2013.01); *G06F 19/3425* (2013.01); *G06F 19/3481* (2013.01); *G06Q 10/10* (2013.01); *G06F 19/325* (2013.01); *G06F 19/328* (2013.01); *G06F 19/345* (2013.01); *G06F 19/3443* (2013.01); *G06F 19/3456* (2013.01)

(58) Field of Classification Search
CPC ...... G06Q 50/22; G06Q 50/24; A61B 5/0006; A61B 8/565; G06F 19/345
USPC ....................................................... 705/2–3
See application file for complete search history.

(56) References Cited

U.S. PATENT DOCUMENTS

| 5,106,482 A | 4/1992 | Milstein et al. |
| 5,716,382 A | 2/1998 | Snell |

(Continued)

OTHER PUBLICATIONS

MediBid; "MediBid is the Marketplace for Medicine®"; printed on Apr. 25, 2011; pp. 1-2; located at http://www.medibid.com.
(Continued)

*Primary Examiner* — Joseph D Burgess

(57) ABSTRACT

Systems and methods are described relating to accepting an indication of at least one attribute of an individual; activating at least one sensor at least partially based on the accepting an indication of at least one attribute of the individual; accepting sensor data from the at least one sensor; and presenting a set of health care options at least partially based on the accepting sensor data from the at least one sensor.

51 Claims, 30 Drawing Sheets

Related U.S. Application Data continuation-in-part of application No. 12/381,680, filed on Mar. 12, 2009, now abandoned, and a continuation-in-part of application No. 12/587,239, filed on Oct. 2, 2009, now abandoned, and a continuation-in-part of application No. 12/587,313, filed on Oct. 5, 2009, and a continuation-in-part of application No. 12/589,124, filed on Oct. 16, 2009, now abandoned, and a continuation-in-part of application No. 12/589,171, filed on Oct. 19, 2009, now abandoned, and a continuation-in-part of application No. 12/589,639, filed on Oct. 26, 2009, now abandoned, and a continuation-in-part of application No. 12/589,728, filed on Oct. 27, 2009, now abandoned, and a continuation-in-part of application No. 12/590,104, filed on Nov. 2, 2009, now abandoned, and a continuation-in-part of application No. 12/590,163, filed on Nov. 3, 2009, now abandoned, and a continuation-in-part of application No. 12/590,250, filed on Nov. 4, 2009, now abandoned, and a continuation-in-part of application No. 12/590,335, filed on Nov. 5, 2009, now abandoned, and a continuation-in-part of application No. 12/592,439, filed on Nov. 24, 2009, now abandoned, and a continuation-in-part of application No. 12/592,541, filed on Nov. 25, 2009, now abandoned, and a continuation-in-part of application No. 12/592,768, filed on Dec. 2, 2009, now Pat. No. 8,095,384, and a continuation-in-part of application No. 12/592,859, filed on Dec. 3, 2009, now abandoned, and a continuation-in-part of application No. 12/655,474, filed on Dec. 30, 2009, now abandoned, and a continuation-in-part of application No. 12/655,580, filed on Dec. 31, 2009, now abandoned, and a continuation-in-part of application No. 12/657,429, filed on Jan. 20, 2010, and a continuation-in-part of application No. 12/657,498, filed on Jan. 21, 2010, now abandoned, and a continuation-in-part of application No. 12/657,980, filed on Jan. 29, 2010, and a continuation-in-part of application No. 12/658,056, filed on Feb. 1, 2010, now abandoned, and a continuation-in-part of application No. 12/658,166, filed on Feb. 3, 2010, now abandoned.

(56) References Cited

U.S. PATENT DOCUMENTS

| | | |
|---|---|---|
| 5,718,247 A | 2/1998 | Frankel |
| 5,738,104 A | 4/1998 | Lo et al. |
| 5,911,132 A | 6/1999 | Sloane |
| 5,926,794 A | 7/1999 | Fethe |
| 6,012,053 A | 1/2000 | Pant et al. |
| 6,014,654 A | 1/2000 | Ariyoshi |
| 6,019,507 A | 2/2000 | Takaki |
| 6,023,685 A | 2/2000 | Brett et al. |
| 6,067,523 A | 5/2000 | Bair et al. |
| 6,155,974 A | 12/2000 | Fish |
| 6,231,187 B1 | 5/2001 | Munoz et al. |
| 6,315,719 B1 | 11/2001 | Rode et al. |
| 6,334,192 B1 | 12/2001 | Karpf |
| 6,480,730 B2 | 11/2002 | Darrow et al. |
| 6,584,445 B2 | 6/2003 | Papageorge |
| 6,807,531 B1 | 10/2004 | Kanai |
| 6,829,499 B1 | 12/2004 | Shahinpoor et al. |
| 6,915,297 B2 | 7/2005 | Chou |
| 7,079,977 B2 | 7/2006 | Osorio et al. |
| 7,120,486 B2 | 10/2006 | Leuthardt et al. |
| 7,194,301 B2 | 3/2007 | Jenkins et al. |
| 7,283,856 B2 | 10/2007 | Boling |
| 7,387,607 B2 | 6/2008 | Holt et al. |
| 7,406,453 B2 | 7/2008 | Mundie et al. |
| 7,424,409 B2 | 9/2008 | Ben-Gal et al. |
| 7,502,650 B2 | 3/2009 | Kieval |
| 7,519,540 B2 | 4/2009 | Mayaud |
| 7,711,580 B1 | 5/2010 | Hudson |
| 7,720,708 B1 | 5/2010 | Elkins, II et al. |
| 7,901,368 B2* | 3/2011 | Flaherty .............. A61H 1/0255 601/33 |
| 7,941,351 B1 | 5/2011 | Rosenfeld et al. |
| 7,949,580 B1 | 5/2011 | Boyer et al. |
| 2002/0059132 A1 | 5/2002 | Quay et al. |
| 2002/0065758 A1* | 5/2002 | Henley .......................... 705/37 |
| 2002/0141629 A1 | 10/2002 | Schreck |
| 2003/0046113 A1* | 3/2003 | Johnson ............... G06Q 10/10 705/3 |
| 2003/0091964 A1 | 5/2003 | Yeager |
| 2003/0101086 A1 | 5/2003 | San Miguel |
| 2003/0130927 A1 | 7/2003 | Kellam et al. |
| 2003/0191669 A1 | 10/2003 | Fitzgerald et al. |
| 2003/0212673 A1 | 11/2003 | Kadayam et al. |
| 2004/0015337 A1 | 1/2004 | Thomas et al. |
| 2004/0193529 A1 | 9/2004 | Asher et al. |
| 2005/0125289 A1 | 6/2005 | Beyda et al. |
| 2005/0149364 A1 | 7/2005 | Ombrellaro |
| 2005/0177051 A1 | 8/2005 | Almen |
| 2006/0136264 A1* | 6/2006 | Eaton ................. G06Q 30/0206 705/2 |
| 2006/0143043 A1 | 6/2006 | McCallie, Jr. et al. |
| 2006/0230033 A1 | 10/2006 | Halevy et al. |
| 2006/0279732 A1 | 12/2006 | Wang et al. |
| 2006/0290885 A1* | 12/2006 | Covannon ............... A61F 9/008 351/212 |
| 2007/0027714 A1 | 2/2007 | Fenno |
| 2007/0087901 A1 | 4/2007 | Brassil et al. |
| 2007/0106143 A1 | 5/2007 | Flaherty |
| 2007/0150024 A1* | 6/2007 | Leyde .................. A61B 5/0476 607/45 |
| 2007/0156647 A1 | 7/2007 | Shen et al. |
| 2007/0192300 A1 | 8/2007 | Reuther et al. |
| 2007/0214008 A1 | 9/2007 | Jung et al. |
| 2007/0250343 A1 | 10/2007 | Sohal |
| 2007/0265507 A1 | 11/2007 | de Lemos |
| 2007/0271119 A1* | 11/2007 | Boerger ................. G06F 19/328 705/2 |
| 2007/0288262 A1 | 12/2007 | Sakaue et al. |
| 2008/0065468 A1 | 3/2008 | Berg et al. |
| 2008/0091086 A1 | 4/2008 | Legere et al. |
| 2008/0147582 A1 | 6/2008 | Micaelian et al. |
| 2008/0154912 A1 | 6/2008 | Weber et al. |
| 2008/0158579 A1 | 7/2008 | Ohga et al. |
| 2008/0172214 A1 | 7/2008 | Col et al. |
| 2008/0215570 A1 | 9/2008 | Maloney et al. |
| 2008/0215627 A1 | 9/2008 | Higgins et al. |
| 2008/0287746 A1 | 11/2008 | Reisman |
| 2009/0006419 A1 | 1/2009 | Savitsky et al. |
| 2009/0023391 A1 | 1/2009 | Falck |
| 2009/0030334 A1 | 1/2009 | Anderson et al. |
| 2009/0036757 A1 | 2/2009 | Brockway et al. |
| 2009/0043801 A1 | 2/2009 | LeClair et al. |
| 2009/0083070 A1 | 3/2009 | Giftakis et al. |
| 2009/0089084 A1 | 4/2009 | Schoenberg |
| 2009/0105557 A1 | 4/2009 | Najafi et al. |
| 2009/0112623 A1 | 4/2009 | Schoenberg |
| 2009/0118595 A1 | 5/2009 | Greiner et al. |
| 2009/0149778 A1 | 6/2009 | Naujokat et al. |
| 2009/0182667 A1 | 7/2009 | Parkes et al. |
| 2009/0192534 A1* | 7/2009 | Ortiz .................... A61B 5/0028 606/157 |
| 2009/0240527 A1 | 9/2009 | Bluth |
| 2009/0281835 A1 | 11/2009 | Patwardhan et al. |
| 2010/0063830 A1 | 3/2010 | Kenedy et al. |
| 2010/0106518 A1 | 4/2010 | Kuo |
| 2010/0113950 A1 | 5/2010 | Lin et al. |
| 2010/0235295 A1 | 9/2010 | Zides et al. |

OTHER PUBLICATIONS

Medicine Online; printed on Apr. 25, 2011; pp. 1-2; located at http://www.medicineonline.com.

(56) References Cited

OTHER PUBLICATIONS

Rustad, Mitch; "Bid-For-Surgery Web Site to Launch"; Medical Tribune; bearing a date of 1999; printed on Apr. 25, 2011; pp. 1-3; 40(21):3; located at http://www.mol.net/media/medscape-trib-/Bid-For-Surgery_Web_Site_To_Launch.htm.
"Internet Archive Wayback Machine"; bearing a date of Feb. 20, 2008; created on Jul. 9, 2015; 1 pg.; located at www.zocdoc.com.
"Quantitative Aspects of Clinical Decision Making Part 2"; bearing a date of Jun. 10, 2006; printed on Jul. 10, 2015; pp. 1-10; located at: www.what-when-how.com.
"Quantitative Aspects of Clinical Decision Making Part 3"; bearing a date of Jun. 10, 2006; printed on Jul. 10, 2015; pp. 1-5; located at: www.what-when-how.com.
Adams, Damon; "Web sites let patients find like-minded physicians"; amednews.com; Mar. 27, 2006; pp. 1-3; American Medical Association.
"Find a Doctor" located at https://web.archive.org/web/20080913161147/http://www.aesnet.org/go/find-a-dr/epilepsy-com; 2007; bearing a date of Jan. 20, 2016; 1 page; epilepsy.com
"Find an Epilepsy Center" located at https://web.archive.org/web/20081206075409/http://www.naeclocator.org/find.htm: 2007; bearing a date of Jan. 20, 2016; 1 page; NAEC.
"Welcome" located at https://web.archive.org/web/20080219060742/http://www.naeclocator.org/; 2007; bearing a date of Jan. 20, 2016; 1 page; NAEC.
"Insurers Roll Out Hospital Quality Data But Hospital Grades, Cost Info Is Optional", Managed Care Week, Mar. 24, 2003, vol. 13, No. 11, p. 1 (5 total pages).
U.S. Appl. No. 12/658,166, filed Feb. 3, 2010, Firminger et al.
U.S. Appl. No. 12/658,056, filed Feb. 1, 2010, Firminger et al.
U.S. Appl. No. 12/657,980, filed Jan. 29, 2010, Firminger et al.
U.S. Appl. No. 12/657,498, filed Jan. 21, 2010, Firminger et al.
U.S. Appl. No. 12/657,429, filed Jan. 20, 2010, Firminger et al.
U.S. Appl. No. 12/655,580, filed Dec. 31, 2009, Firminger et al.
U.S. Appl. No. 12/655,474, filed Dec. 30, 2009, Firminger et al.
U.S. Appl. No. 12/592,859, filed Dec. 3, 2009, Firminger et al.
U.S. Appl. No. 12/592,768, filed Dec. 2, 2009, Firminger et al.
U.S. Appl. No. 12/592,541, filed Nov. 25, 2009, Firminger et al.
U.S. Appl. No. 12/592,439, filed Nov. 24, 2009, Firminger et al.
U.S. Appl. No. 12/590,335, filed Nov. 5, 2009, Firminger et al.
U.S. Appl. No. 12/590,250, filed Nov. 4, 2009, Firminger et al.
U.S. Appl. No. 12/590,163, filed Nov. 3, 2009, Firminger et al.
U.S. Appl. No. 12/590,104, filed Nov. 2, 2009, Firminger et al.
U.S. Appl. No. 12/589,728, filed Oct. 27, 2009, Firminger et al.
U.S. Appl. No. 12/589,639, filed Oct. 26, 2009, Firminger et al.
U.S. Appl. No. 12/589,171, filed Oct. 19, 2009, Firminger et al.
U.S. Appl. No. 12/589,124, filed Oct. 16, 2009, Firminger et al.
U.S. Appl. No. 12/587,313, filed Oct. 5, 2009, Firminger et al.
U.S. Appl. No. 12/587,239, filed Oct. 2, 2009, Firminger et al.
U.S. Appl. No. 12/381,680, filed Mar. 12, 2009, Firminger et al.
U.S. Appl. No. 12/381,377, filed Mar. 10, 2009, Firminger et al.
Axelrod et al., "Smoke and Mirrors: Gathering User Requirements for Emerging Affective Systems," 26th Int. Conf. Information Technology Interfaces /TI 2004, Jun. 7-10, 2004, Cavtat, Croatia, pp. 323-328.
"Cancer in Scotland: Radiotherapy Activity Planning for Scotland 2011-2015," available at http://www.scotland.gov.uk/Publications/2006/01/24131719/28, (2006).
Clarke, "IMEC has a brain wave: feed EEG emotion back into games," EE Times online, http://www.eetimes.eu/design/202801063 (Nov. 1, 2007).
Cohn, J.N., Introduction to Surrogate Markers, Circulation 109: IV20-21, American Heart Association, (2004).
Frenkel et al., "An approach for integrating complementary-alternative medicine into primary care," Fam. Pratt., 20(3), pp. 324-332 (2003).
Goodman, Clifford S., "Introduction to Health Care Technology Assessment," available at http://www.nlm.nih.gov/nichsr/hta101/ta101_c1.html, (Jan. 2004).
Martinez-Serna et al., "Symptom Priority Ranking in the Care of Gastroesophageal Reflux: A Review of 1,850 Cases," Dig Dis, 17:219-224 (1999).
Nikovski, D., "Constructing Bayesian Networks for Medical Diagnosis from Incomplete and Partially Correct Statistics," IEEE Transactions on Knowledge and Data Engineering, vol. 12:4, pp. 509-516 (2000).
Physorg.com, "New mini-sensor may have biomedical and security applications," Nov. 1, 2007, http://www.physorg.com/news113151078.html.
Sanfey, "Social Decision-Making: Insights from Game Theory and Neuroscience," Science, vol. 318, pp. 598-601 (Oct. 26, 2007).
Tarricone et al., "Economic evaluation of nimesulide versus diclofenac in the treatment of osteoarthritis in France, Italy and Spain," Clin. Drug Invest. 21(7) pp. 453-464 (2001).

* cited by examiner

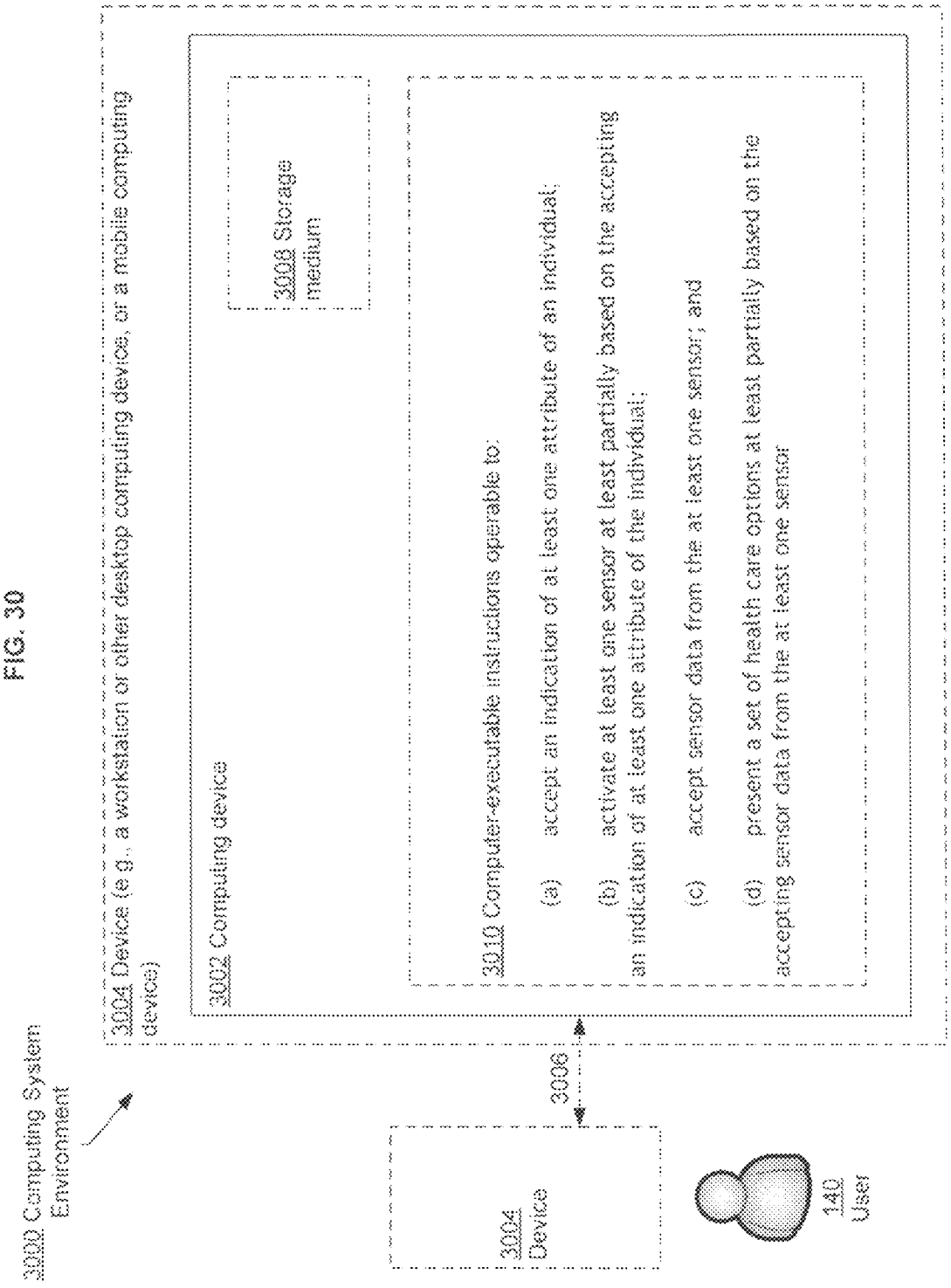

COMPUTATIONAL SYSTEMS AND METHODS FOR HEALTH SERVICES PLANNING AND MATCHING

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC 119(e) for provisional patent applications, for any and all parent, grandparent, great-grandparent, etc. applications of the Related Application(s)).

Related Applications

For purposes of the USPTO extra-statutory requirements, the present application constitutes a continuation-in-part of U.S. patent application Ser. No. 12/381,377, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 10 Mar. 2009 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/381,680, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 12 Mar. 2009 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/587,239, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 2 Oct. 2009 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/587,313, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 5 Oct. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/589,124, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 16 Oct. 2009 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/589,171, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 19 Oct. 2009 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/589,639, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 26 Oct. 2009 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/589,728, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 27 Oct. 2009 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/590,104, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 2 Nov. 2009 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/590,163, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 3 Nov. 2009 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/590,250, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 4 Nov. 2009 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/590,335, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 5 Nov. 2009 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/592,439, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 24 Nov. 2009 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/592,541, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 25 Nov. 2009 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/592,768, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 2 Dec. 2009 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/592,859, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 3 Dec. 2009 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/655,474, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 30 Dec. 2009 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/655,580, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 31 Dec. 2009 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/657,429, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 20 Jan. 2010 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/657,498, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 21 Jan. 2010 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/657,980, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 29 Jan. 2010 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/658,056, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 1 Feb. 2010 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/658,166, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 3 Feb. 2010 now abandoned which is currently co-pending, or is an application of which a currently co-pending application is entitled to the benefit of the filing date.

The U.S. Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

TECHNICAL FIELD

This description relates to data capture and data handling techniques.

SUMMARY

In one aspect, a method includes but is not limited to accepting an indication of at least one attribute of an individual, activating at least one sensor at least partially based on the accepting an indication of at least one attribute of the individual, accepting sensor data from the at least one sensor, and presenting a set of health care options at least partially based on the accepting sensor data from the at least one sensor. In addition to the foregoing, other apparatus aspects are described in the claims, drawings, and text forming a part of the present disclosure.

In one or more various aspects, related systems include but are not limited to circuitry and/or programming for effecting the herein referenced method aspects; the circuitry and/or programming can be virtually any combination of hardware, software, and/or firmware configured to effect the herein referenced method aspects depending upon the design choices of the system designer.

In one aspect, a system includes but is not limited to means for accepting an indication of at least one attribute of an individual, means for activating at least one sensor at least partially based on the accepting an indication of at least one attribute of the individual, means for accepting sensor data from the at least one sensor, and means for presenting a set of health care options at least partially based on the accepting sensor data from the at least one sensor. In addition to the foregoing, other apparatus aspects are described in the claims, drawings, and text forming a part of the present disclosure.

In one aspect, a system includes but is not limited to circuitry for accepting an indication of at least one attribute of an individual, circuitry for activating at least one sensor at least partially based on the accepting an indication of at least one attribute of the individual, circuitry for accepting sensor data from the at least one sensor, and circuitry for presenting a set of health care options at least partially based on the accepting sensor data from the at least one sensor. In addition to the foregoing, other apparatus aspects are described in the claims, drawings, and text forming a part of the present disclosure.

In one aspect, a computer program product includes but is not limited to a signal-bearing medium bearing one or more instructions for accepting an indication of at least one attribute of an individual, one or more instructions for activating at least one sensor at least partially based on the accepting an indication of at least one attribute of the individual, one or more instructions for accepting sensor data from the at least one sensor, and one or more instructions for presenting a set of health care options at least partially based on the accepting sensor data from the at least one sensor. In addition to the foregoing, other method aspects are described in the claims, drawings, and text forming a part of the present disclosure.

In one aspect, a system includes but is not limited to a computing device and instructions that when executed on the computing device cause the computing device to accept an indication of at least one attribute of an individual, activate at least one sensor at least partially based on the accepting an indication of at least one attribute of the individual, accept sensor data from the at least one sensor, and present a set of health care options at least partially based on the accepting sensor data from the at least one sensor. In addition to the foregoing, other method aspects are described in the claims, drawings, and text forming a part of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

BRIEF DESCRIPTION OF THE FIGURES

FIG. 30 illustrates an example device in which embodiments may be implemented related to health services planning and matching, which may serve as a context for introducing one or more processes and/or devices described herein.

DETAILED DESCRIPTION

Figure 1:
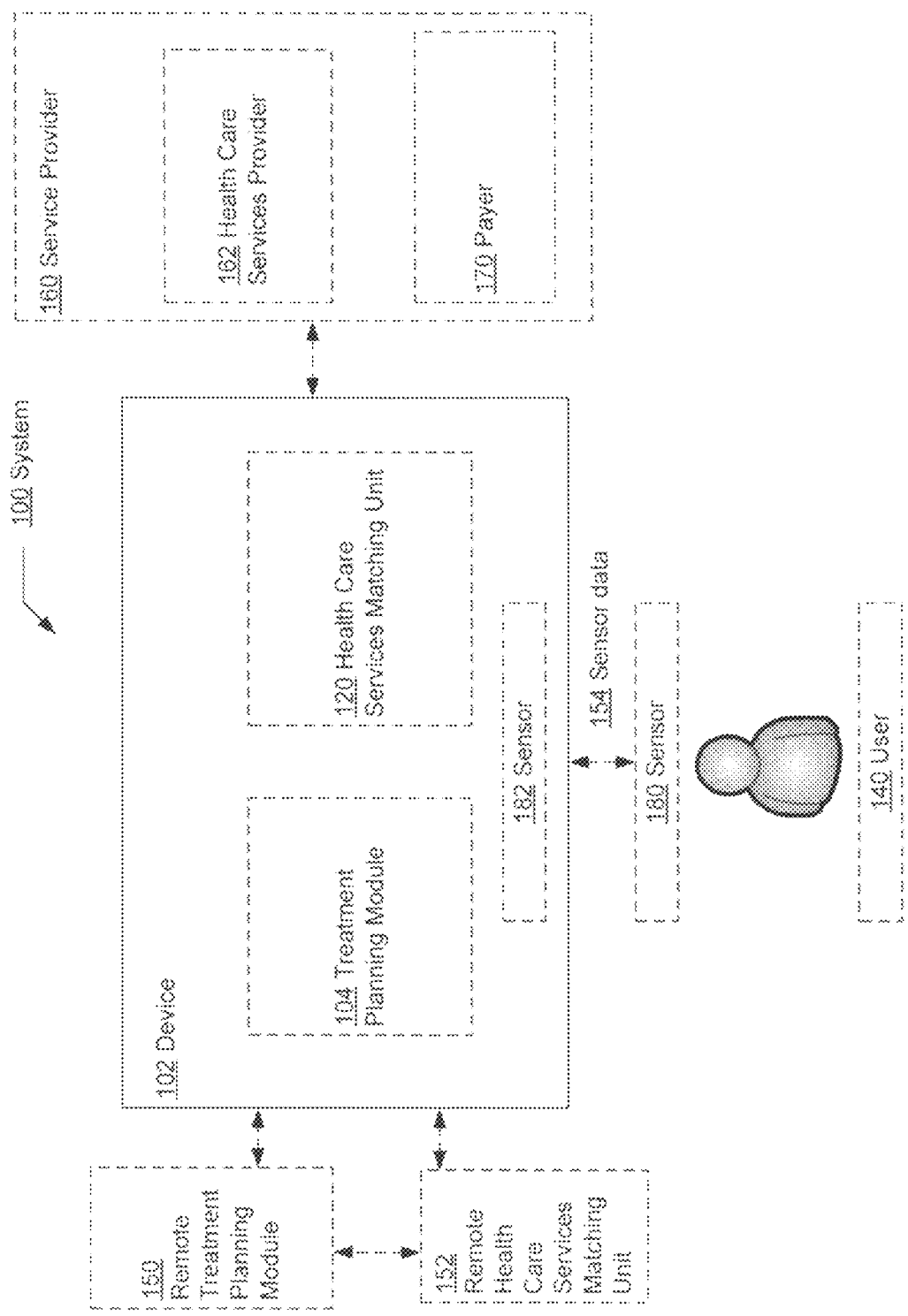
FIG. 1 illustrates an example of a health services planning and matching system in which embodiments may be implemented, perhaps in a device and/or through a network, which may serve as a context for introducing one or more processes and/or devices described herein.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 illustrates an example system 100 in which embodiments may be implemented. The system 100 includes a device 102. The device 102 may contain, for example, sensor 182, and treatment planning module 104. The device 102 may communicate over a network or directly with remote treatment planning module 150 and/or remote health care services matching unit 152. User 140 may interact directly or through a user interface with device 102. Device 102 may communicate with service provider 160, which may include health care services provider 162 and/or payer 170. Device 102 may accept sensor data 154 from sensor 180 proximal to a user 140 or from remote sensor 182 to provide a plurality of health services options, for example via treatment planning module 104. Device 102 may match a selected health service option with an appropriate service provider via, for example health care services matching unit 120. Service provider 160 may include, for example, health care services provider 162 and/or payer 170.

In FIG. 1, health care services matching unit 120 may solicit a health care services option from a service provider 160. Such a solicitation may include an invitation to bid in an auction, a reverse auction, or the like. Results of such a solicitation may include matching a doctor capable of providing a chosen health care services option with the user 140 in need of the chosen health care services option, perhaps according to one or more preferences provided by the user 140. Health care services matching unit 120 may otherwise find a service provider 160 through the use of a directory or other listing of health services providers.

In FIG. 1, the device 102 is illustrated as possibly being included within a system 100. Of course, virtually any kind of computing device may be used to implement the special purpose sensor 180 and/or special purpose sensor 182, special purpose treatment planning module 104 and/or special purpose health care services matching unit 120, such as, for example, a programmed workstation, a programmed desktop computer, a programmed networked computer, a programmed server, a collection of programmed servers and/or databases, a programmed virtual machine running inside a computing device, a programmed mobile computing device, or a programmed tablet PC.

Additionally, not all of the sensor 182, sensor 180, treatment planning module 104 and/or health care services matching unit 120 need be implemented on a single computing device. For example, the sensor 182, treatment planning module 104, and/or health care services matching unit 120 may be implemented and/or operable on a remote computer, while a user interface and/or local instance of the sensor 180, treatment planning module 104, and/or health care services matching unit 120 are implemented and/or occur on a local computer. Further, aspects of the sensors 180 and 182, treatment planning module 104, and/or health care services matching unit 120 may be implemented in different combinations and implementations than that shown in FIG. 1. For example, functionality of a user interface may be incorporated into the sensor 180, treatment planning module 104, and/or health care services matching unit 120. The sensor 180, sensor 182, treatment planning module 104, and/or health care services matching unit 120 may perform simple data relay functions and/or complex data analysis, including, for example, fuzzy logic and/or traditional logic steps. Further, many methods of searching health care and/or service provider databases known in the art may be used, including, for example, unsupervised pattern discovery methods, coincidence detection methods, and/or entity relationship modeling. In some embodiments, the sensor 180, sensor 182, treatment planning module 104, and/or health care services matching unit 120 may process user input data according to health care options and/or service provider information available as updates through a network.

Treatment planning module 104 and/or health care services matching unit 120 may access data stored in virtually any type of memory that is able to store and/or provide access to information in, for example, a one-to-many, many-to-one, and/or many-to-many relationship. Such a memory may include, for example, a relational database and/or an object-oriented database, examples of which are provided in more detail herein.

Figure 2:
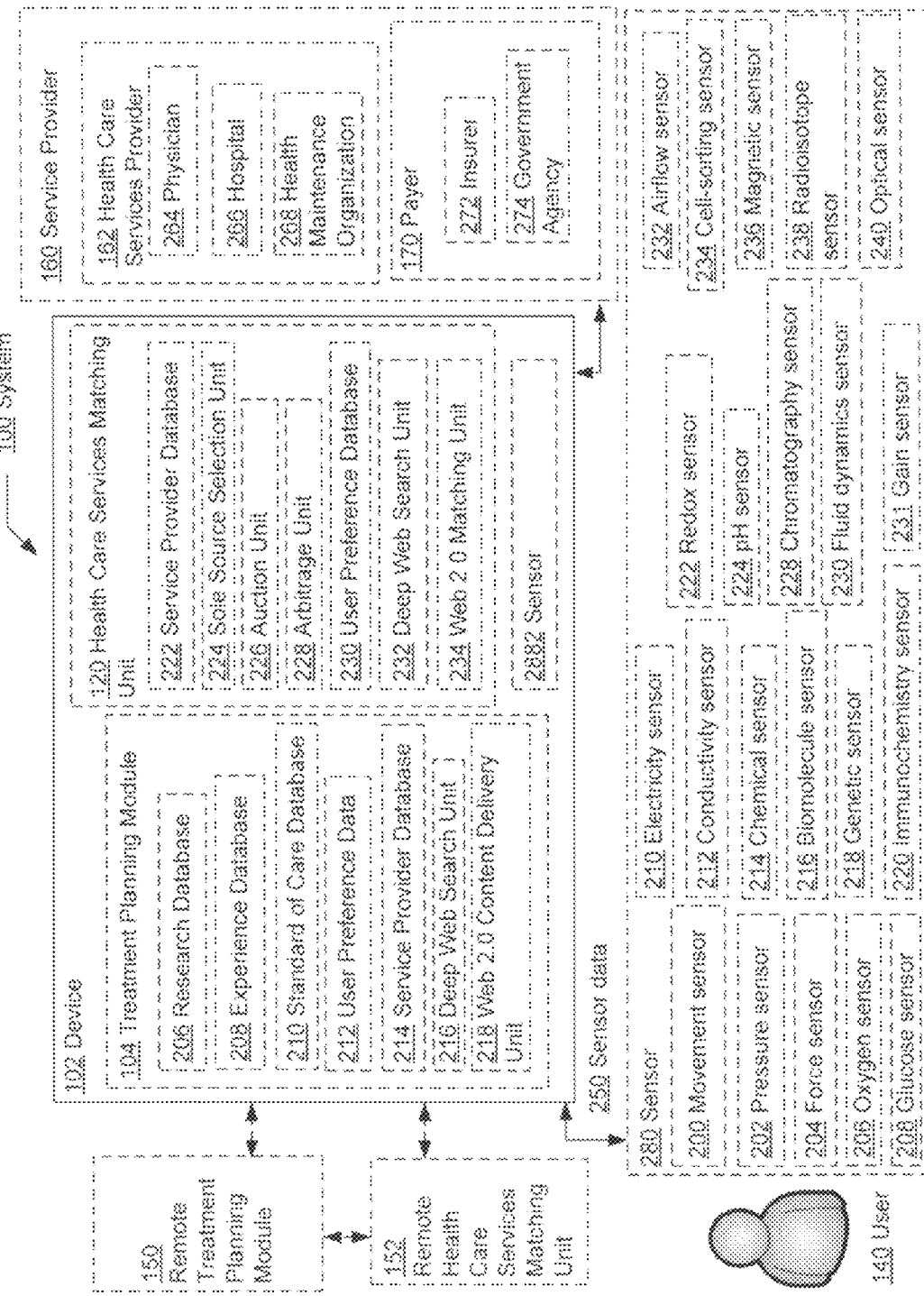
FIG. 2 illustrates certain alternative embodiments of the health services planning and matching system of FIG. 1.

FIG. 2 illustrates certain alternative embodiments of the system 100 of FIG. 1. In FIG. 2, the user 140 may interact with treatment planning module 104 and/or health care services matching unit 120 operable on the device 102. Sensor 280 may acquire sensor data 250 via movement sensor 200, pressure sensor 202, force sensor 204, oxygen sensor 206, glucose sensor 208, electricity sensor 210, conductivity sensor 212, chemical sensor 214, biomolecule sensor 216, genetic sensor 218, immunochemistry sensor 220, redox sensor 222, pH sensor 224, chromoatography sensor 228, fluid dynamics sensor 230, gain sensor 231, airflow sensor 232, cell-sorting sensor 234, magnetic sensor 236, radioisotope sensor 238, and/or optical sensor 240.

Alternatively, remote sensor 282 may generate sensor data from signals received from a distance. Examples of such remote sensing include the use of signal processing algorithms for a wireless sensor that can classify different types of motion and closely monitor a person's breathing and/or heart rate. For example, this type of sensor is useful in monitoring premature babies in a neonatal intensive care unit. Premature infants have very sensitive and fragile skin, which can make it difficult to directly attach sensors to them. A remote sensor can wirelessly monitor an infant's movements, including breathing and heart rate. Similarly, the sensor can be installed in a home for elder care or other outpatient monitoring. See also U.S. Pat. No. 6,315,719; U.S. Pat. No. 7,387,607; and U.S. Pat. No. 7,424,409; each of which is incorporated herein by reference.

Sensor data 250 may be accepted by treatment planning module 104 implemented on the device 102. The device 102 can communicate over a network with remote treatment planning module 150 and/or remote health care services matching unit 152. Treatment planning module 104 may include, for example, research database 206, experience database 208, standard of care database 210, user preference data 212, service provider database 214, Deep Web search unit 216, and/or Web 2.0 content delivery unit 218. The treatment planning module 104 may access and send health-related services options 242 to user 140. User 140 may subsequently choose and send health-related services selection 244 including a desired health service option from among a plurality of health services options to device 102 including health care services matching unit 120. Health care services matching unit 120 may include, for example, service provider database 222, sole source selection unit 224, auction unit 226, 228 arbitrage unit 228, user preference database 230, Deep Web search unit 232, and/or Web 2.0 matching unit 234. Health care services matching unit 120 may communicate directly or over a network with service provider 160 to obtain a suitable health-related service according to health-related services selection 244 and any user preference contained, for example, in user preference database 230. Service provider 160 may include health care services provider 162 and/or payer 170. Health care services provider 162 may include, for example, physician 264, hospital 266, and/or health maintenance organization 268. Payer 170 may include, for example, insurer 272, and/or government agency 274. Health care services matching unit 120 may then present matched health-related service 246 to user 140.

In this way, the user 140, who may be using a mobile device that is connected through a network with the system 100 and/or device 102 (e.g., in an office, outdoors and/or in a public environment), may generate a plurality of health service options as if the user 140 were interacting locally with the device 102 and/or system 100.

As referenced herein, the treatment planning module 104 and/or health care services matching unit 120 may be used to perform various data querying and/or recall techniques with respect to sensor data 250 and/or a plurality of health service options, in order to obtain and/or present a plurality of health service options. For example, where the sensor data 250 is organized, keyed to, and/or otherwise accessible using one or more reference health-related status indicators such as symptom, disease, diagnosis, or the like, treatment planning module 104 and/or health care services matching unit 120 may employ various Boolean, statistical, and/or semi-boolean searching techniques to match sensor data 250 with one or more indications of health status and/or one or more relevant health-related services options. Similarly, for example, where user preference data is organized, keyed to, and/or otherwise accessible using one or more service provider 160 interest profiles, various Boolean, statistical, and/or semi-boolean searching techniques may be performed by health care services matching unit 120 to match a given health-related services selection 244 with a service provider 160 to present, for example, a matched health-related service 246.

Many examples of databases and database structures may be used in connection with the treatment planning module 104 and/or health care services matching unit 120. Such examples include hierarchical models (in which data is organized in a tree and/or parent-child node structure), network models (based on set theory, and in which multi-parent structures per child node are supported), or object/relational models (combining the relational model with the object-oriented model).

Still other examples include various types of eXtensible Mark-up Language (XML) databases. For example, a database may be included that holds data in some format other than XML, but that is associated with an XML interface for accessing the database using XML. As another example, a database may store XML data directly. Additionally, or alternatively, virtually any semi-structured database may be used, so that context may be provided to/associated with stored data elements (either encoded with the data elements, or encoded externally to the data elements), so that data storage and/or access may be facilitated.

Such databases, and/or other memory storage techniques, may be written and/or implemented using various programming or coding languages. For example, object-oriented database management systems may be written in programming languages such as, for example, C++ or Java. Relational and/or object/relational models may make use of database languages, such as, for example, the structured query language (SQL), which may be used, for example, for interactive queries for information and/or for gathering and/or compiling data from the relational database(s).

For example, SQL or SQL-like operations over one or more reference health attribute and/or reference service provider may be performed, or Boolean operations using a reference health attribute and/or reference service provider may be performed. For example, weighted Boolean operations may be performed in which different weights or priorities are assigned to one or more of the reference health-related status attributes and/or reference service providers, including reference health conditions and/or reference service providers associated with various reference health-related status attributes, perhaps relative to one another. For example, a number-weighted, exclusive-OR operation may be performed to request specific weightings of desired (or undesired) health reference data or service providers to be included or excluded. Reference health-related status attributes may include normal physiological values for such health-related things as pain, reaction time, body or eye movement, memory, alertness, blood pressure, or the like. Such normal physiological values may be "normal" relative to the user 140, to a subpopulation to which the user 140 belongs, or to a general population. Similarly, reference service providers may be associated with, for example, the general medical community, a medical specialty, a local geographical area or the like.

Following are a series of flowcharts depicting implementations. For ease of understanding, the flowcharts are organized such that the initial flowcharts present implementations via an example implementation and thereafter the following flowcharts present alternate implementations and/or expansions of the initial flowchart(s) as either sub-component operations or additional component operations building on one or more earlier-presented flowcharts. Those having skill in the art will appreciate that the style of presentation used herein (e.g., beginning with a presentation of a flowchart presenting an example implementation and thereafter providing additions to and/or further details in subsequent flowcharts) generally allows for a rapid and easy understanding of the various process implementations. In addition, those skilled in the art will further appreciate that the style of presentation used herein also lends itself well to modular and/or object-oriented program design paradigms.

Figure 3:
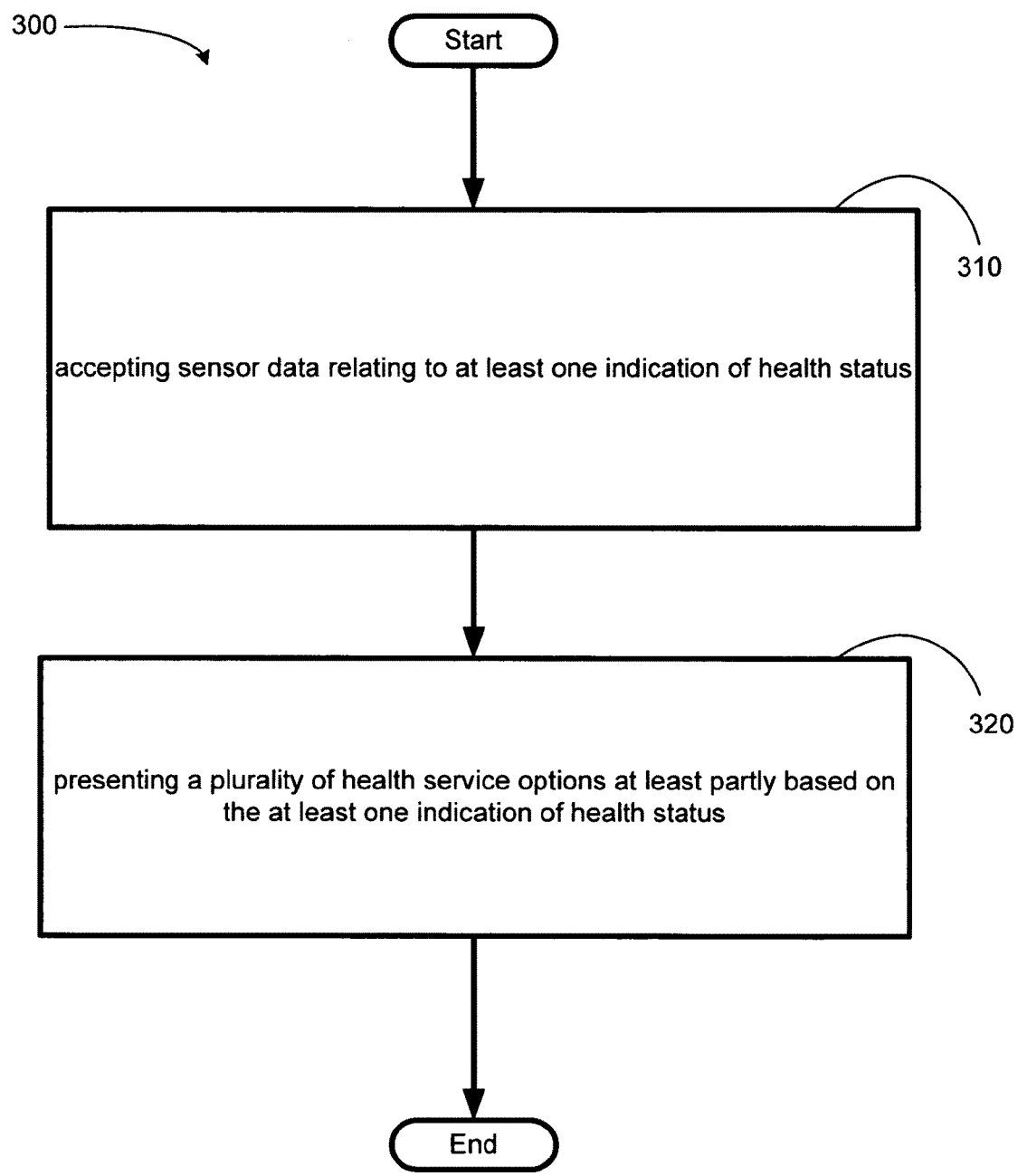
FIG. 3 illustrates an example of an operational flow representing example operations related to health services planning and matching, which may serve as a context for introducing one or more processes and/or devices described herein.

FIG. 3 illustrates an operational flow 300 representing example operations related to health services planning and matching. In FIG. 3 and in following figures that include various examples of operational flows, discussion and explanation may be provided with respect to the above-described system environments of FIGS. 1-2, and/or with respect to other examples and contexts. However, it should be understood that the operational flows may be executed in a number of other environments and contexts including that of FIGS. 17 and 18, and/or in modified versions of FIGS. 1-2. Also, although the various operational flows are presented in the sequences illustrated, it should be understood that the various operations may be performed in other orders than those which are illustrated, or may be performed concurrently.

After a start operation, operation 310 depicts accepting sensor data relating to at least one indication of health status. For example, treatment planning module 104 and/or device 102 may accept sensor data relating to at least one indication of health status. In one embodiment, sensor 280 may transmit sensor data 250 to device 102 relating to a symptom or disease. The user 140 may be a patient having a medical condition, an individual experiencing one or more symptoms, an asymptomatic individual, or the like. Sensor data relating to at least one indication of health status may also include indications for cosmetic enhancement, pregnancy, or improvement in athletic performance. In another embodiment, treatment planning module 104 accepting blood pressure sensor data indicating a sustained rise in blood pressure over time may present a plurality of health service options based on the indication of high blood pressure received from the blood pressure sensor. The user 140 may then analyze the plurality of health service options to determine whether or not to proceed in finding a health service provider for the presented options for addressing the detected high blood pressure. In one embodiment, user 140 may wish to find a health service provider to address one of a plurality of presented health service options. In this case, health care services matching unit 120 may provide, for example, an auction system by which user 140 can procure the desired health care service, for example, in a given geographic area at a competitive price.

Operation 320 depicts presenting a plurality of health service options at least partly based on the at least one indication of health status. For example, treatment planning module 104 and/or device 102 may present a plurality of health service options at least partly based on the at least one indication of health status. In one embodiment, treatment planning module 104 may, based on accepted sensor data, present a set of health service options according to one or more diagnoses or treatment paths corresponding to symptom(s) or conditions.

In one embodiment, a stochastic model can be built to describe an image, for example a medical image. The stochastic model may then be used to compare other images in the same way that it compares other data sequences. Such a system is useful in automatic screening of medical image data to identify features of interest. The system can be used to compare images of the same patient taken at different times, for example to monitor progress of a tumor, or it could be used to compare images taken from various patients with a standard image.

D. Nikovski, "Constructing Bayesian Networks for Medical Diagnosis from Incomplete and Partially Correct Statistics," IEEE Transactions on Knowledge and Data Engineering, Vol. 12:4, pp. 509-516 (2000). The paper discusses several knowledge engineering techniques for the construction of Bayesian networks for medical diagnostics when the available numerical probabilistic information is incomplete or partially correct. This situation occurs often when epidemiological studies publish only indirect statistics and when significant unmodeled conditional dependence exists in the problem domain. While nothing can replace precise and complete probabilistic information, still a useful diagnostic system can be built with imperfect data by introducing domain-dependent constraints. We propose a solution to the problem of determining the combined influences of several diseases on a single test result from specificity and sensitivity data for individual diseases. We also demonstrate two techniques for dealing with unmodeled conditional dependencies in a diagnostic network. These techniques are discussed in the context of an effort to design a portable device for cardiac diagnosis and monitoring from multimodal signals.

Figure 4:
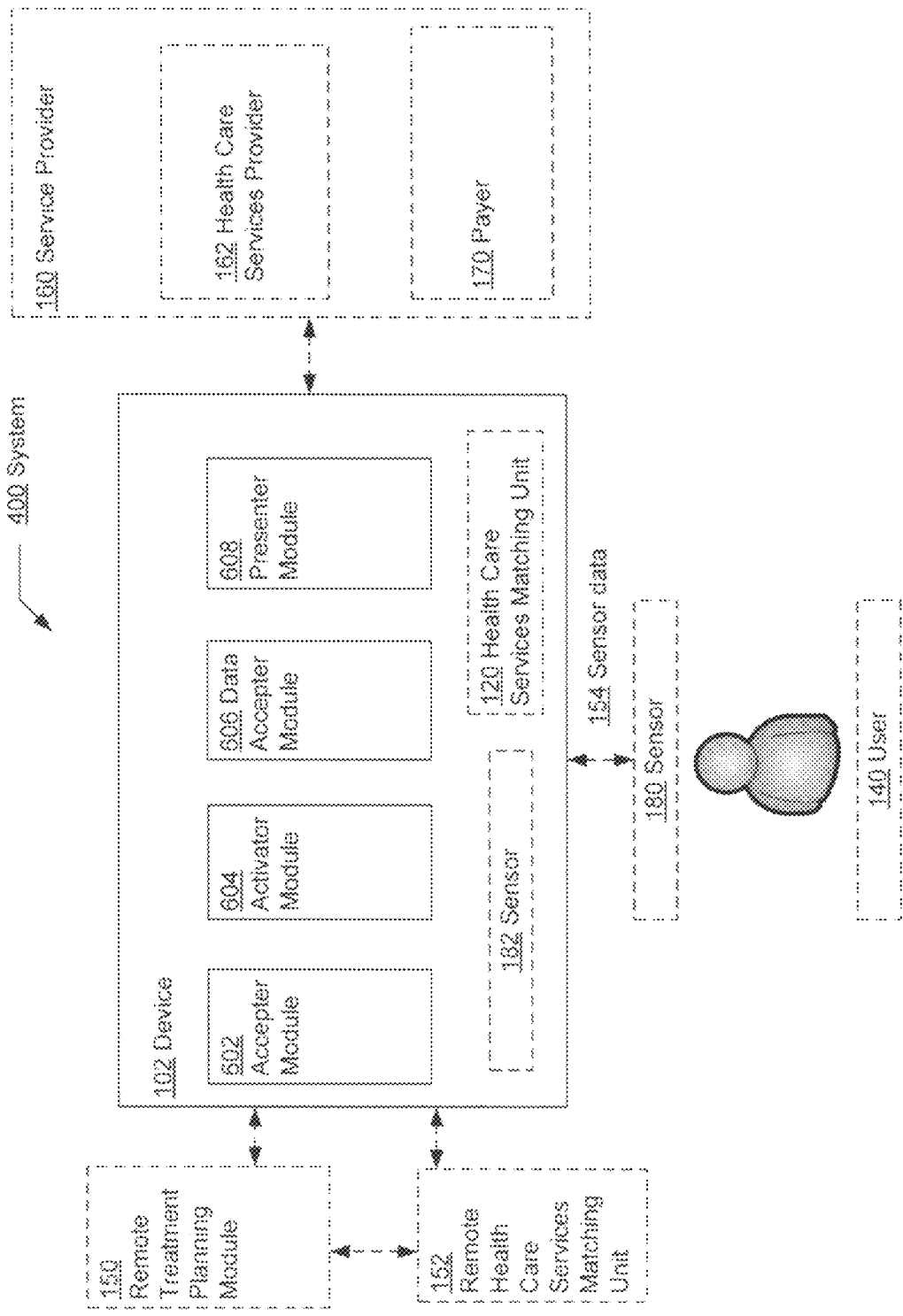
FIG. 4 illustrates an example of a health services planning and matching system in which embodiments may be implemented, perhaps in a device and/or through a network, which may serve as a context for introducing one or more processes and/or devices described herein.

FIG. 4 illustrates an example system 400 in which embodiments may be implemented. The system 400 includes a device 102. The device 102 may contain, for example, accepter module 602, activator module 604, data accepter module 606, and/or presenter module 608. The device 102 may communicate over a network or directly with remote treatment planning module 150 and/or remote health care services matching unit 152. User 140 may interact directly or through a user interface with device 102. Device 102 may communicate with service provider 160, which may include health care services provider 162 and/or payer 170. Device 102 may accept user input to provide one or more health services options, for example via accepter module 602, activator module 604, data accepter module 606, and/or presenter module 608. Device 102 may accept a selected health service option and match it with an appropriate service provider via, for example health care services matching unit 120. Service provider 160 may include, for example, health care services provider 162 and/or payer 170.

In FIG. 4, the device 102 is illustrated as possibly being included within a system 400. Of course, virtually any kind of computing device may be used to implement the special purpose health care services matching unit 120, special purpose accepter module 602, special purpose activator module 604, special purpose data accepter module 606, and/or special purpose presenter module 608, such as, for example, a workstation, a desktop computer, a networked computer, a server, a collection of servers and/or databases, a virtual machine running inside a computing device, a mobile computing device, or a tablet PC.

Additionally, not all of the health care services matching unit 120, accepter module 602, activator module 604, data accepter module 606, and/or presenter module 608 need be implemented on a single computing device. For example, health care services matching unit 120, accepter module 602, activator module 604, data accepter module 606, and/or presenter module 608 may be implemented and/or operable on a remote computer, while a user interface and/or local instance of the health care services matching unit 120, accepter module 602, activator module 604, data accepter module 606, and/or presenter module 608 are implemented and/or occur on a local computer. Further, aspects of health care services matching unit 120, accepter module 602, activator module 604, data accepter module 606, and/or presenter module 608 may be implemented in different combinations and implementations than that shown in FIG. 4. For example, functionality of a user interface may be incorporated into the health care services matching unit 120, accepter module 602, activator module 604, data accepter module 606, and/or presenter module 608. The health care services matching unit 120, accepter module 602, activator module 604, data accepter module 606, and/or presenter module 608 may perform simple data relay functions and/or complex data analysis, including, for example, fuzzy logic and/or traditional logic steps. Further, many methods of searching health care and/or service provider databases known in the art may be used, including, for example, unsupervised pattern discovery methods, coincidence detection methods, and/or entity relationship modeling. In some embodiments, health care services matching unit 120, accepter module 602, activator module 604, data accepter module 606, and/or presenter module 608 may process user input data according to health care options and/or service provider information available as updates through a network.

Health care services matching unit 120, accepter module 602, activator module 604, data accepter module 606, and/or presenter module 608 may access data stored in virtually any type of memory that is able to store and/or provide access to information in, for example, a one-to-many, many-to-one, and/or many-to-many relationship. Such a memory may include, for example, a relational database and/or an object-oriented database, examples of which are provided in more detail herein.

Figure 5:
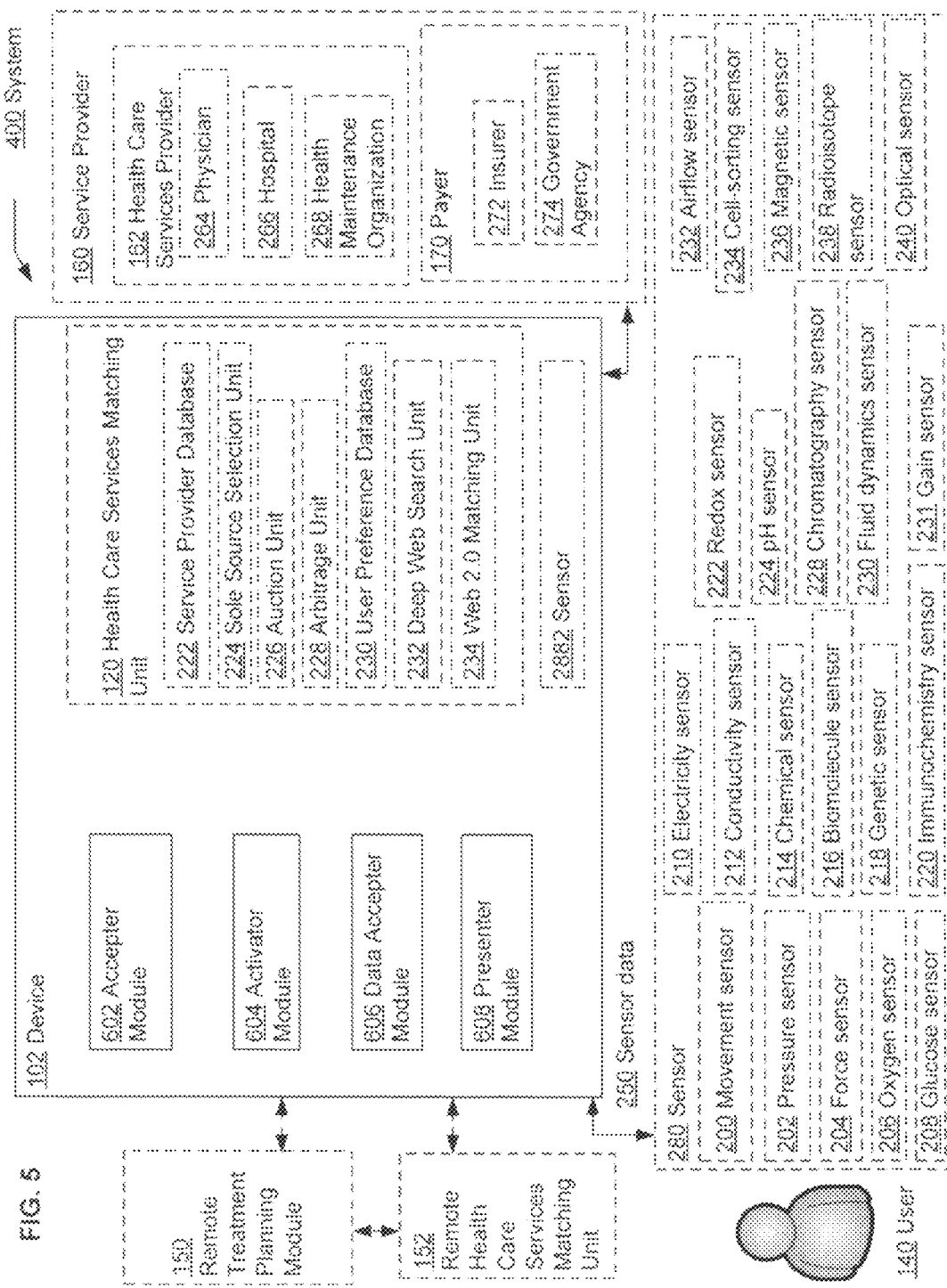
FIG. 5 illustrates certain alternative embodiments of the health services planning and matching system of FIG. 4.

FIG. 5 further illustrates system 400 including device 102, which may further include health care services matching module 120, sensor 2882, accepter module 602, activator module 604, data accepter module 606, and/or presenter module 608. Health care services matching module 120 may include service provider database 222, sole source selection unit 224, auction unit 226, arbitrage unit 228, user preference database 230, deep web search unit 232 and/or Web 2.0 matching unit 234. Device 102 may communicate with remote treatment planning module 150, remote health care services matching unit 152, and/or service provider 160. Service provider 160 may include health care services provider 162 and/or payer 170. Health care services provider 162 may include physician 264, hospital 266, and/or health maintenance organization 268. Payer 170 may include insurer 272 and/or government agency 274. Additionally, device 102 may accept sensor data 250 from and/or communicate with sensor 280. Sensor 280 may include movement sensor 200, pressure sensor 202, force sensor 204, oxygen sensor 206, glucose sensor 208, electricity sensor 210, conductivity sensor 212, chemical sensor 214, biomolecule sensor 216, genetic sensor 218, immunochemistry sensor 220, redox sensor 222, pH sensor 224, chromatography sensor 228, fluid dynamics sensor 230, gain sensor 231, airflow sensor 232, cell-sorting sensor 234, magnetic sensor 236, radioisotope sensor 238, and/or optical sensor 240.

Figure 6:
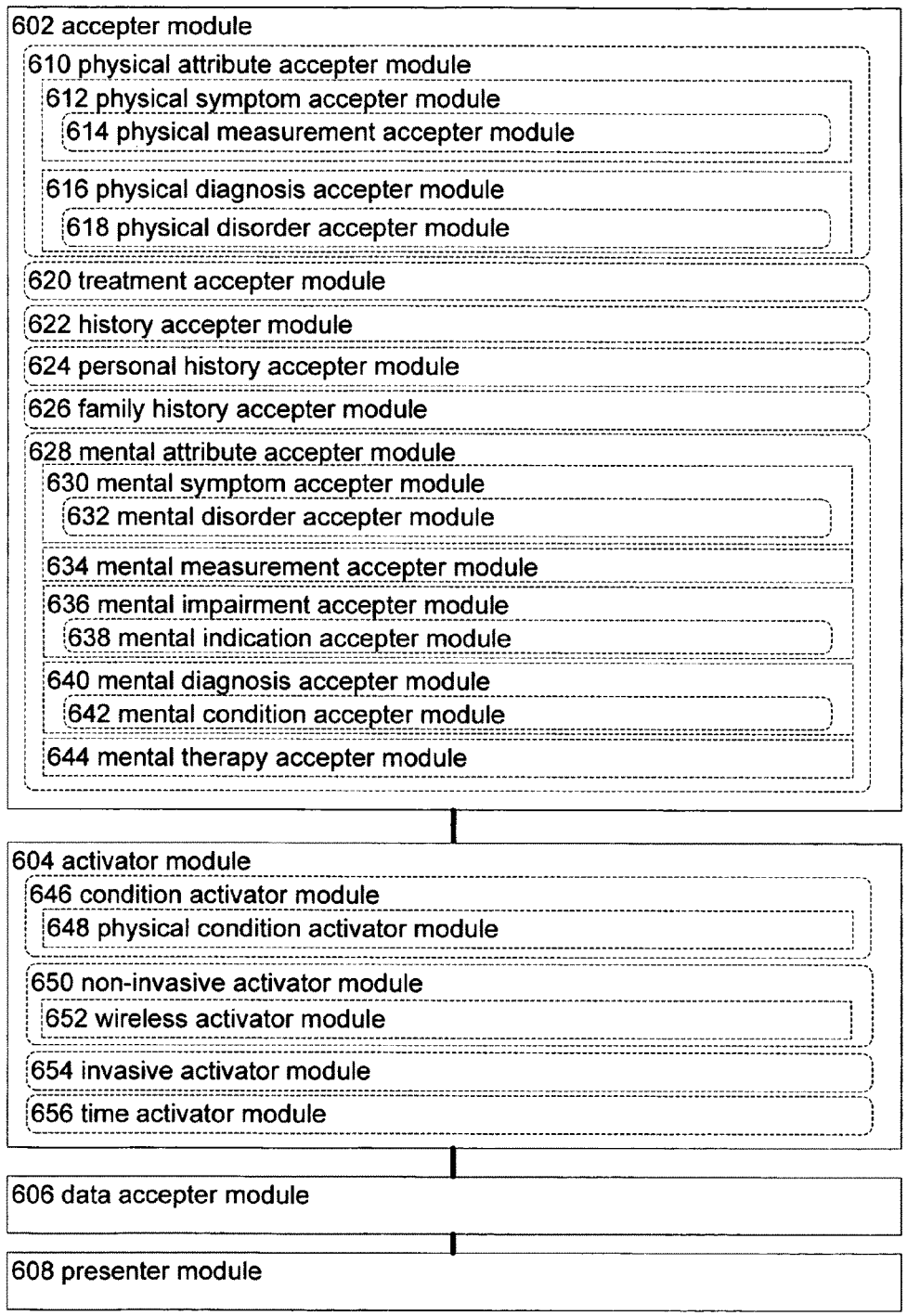
FIG. 6 illustrates certain alternative embodiments of the health services planning and matching system of FIG. 4.

FIG. 6 further illustrates system 400 including accepter module 602, activator module 604, data accepter module 606, and/or presenter module 608. Accepter module 602 may include physical attribute accepter module 610, treatment accepter module 620, history accepter module 622, personal history accepter module 624, family history accepter module 626, and/or mental attribute accepter module 628. Physical attribute accepter module 610 may include physical symptom accepter module 612 and/or physical diagnosis accepter module 616. Physical symptom accepter module 612 may include physical measurement accepter module 614. Physical diagnosis accepter module 616 may include physical disorder accepter module 618. Mental attribute accepter module 628 may include mental symptom accepter module 630, mental measurement accepter module 634, mental impairment accepter module 636, mental diagnosis accepter module 640, and/or mental therapy accepter module 644. Mental symptom accepter module 630 may include mental disorder accepter module 632. Mental impairment accepter module 636 may include mental indication accepter module 638. Mental diagnosis accepter module 640 may include mental condition accepter module 642.

Figure 7:
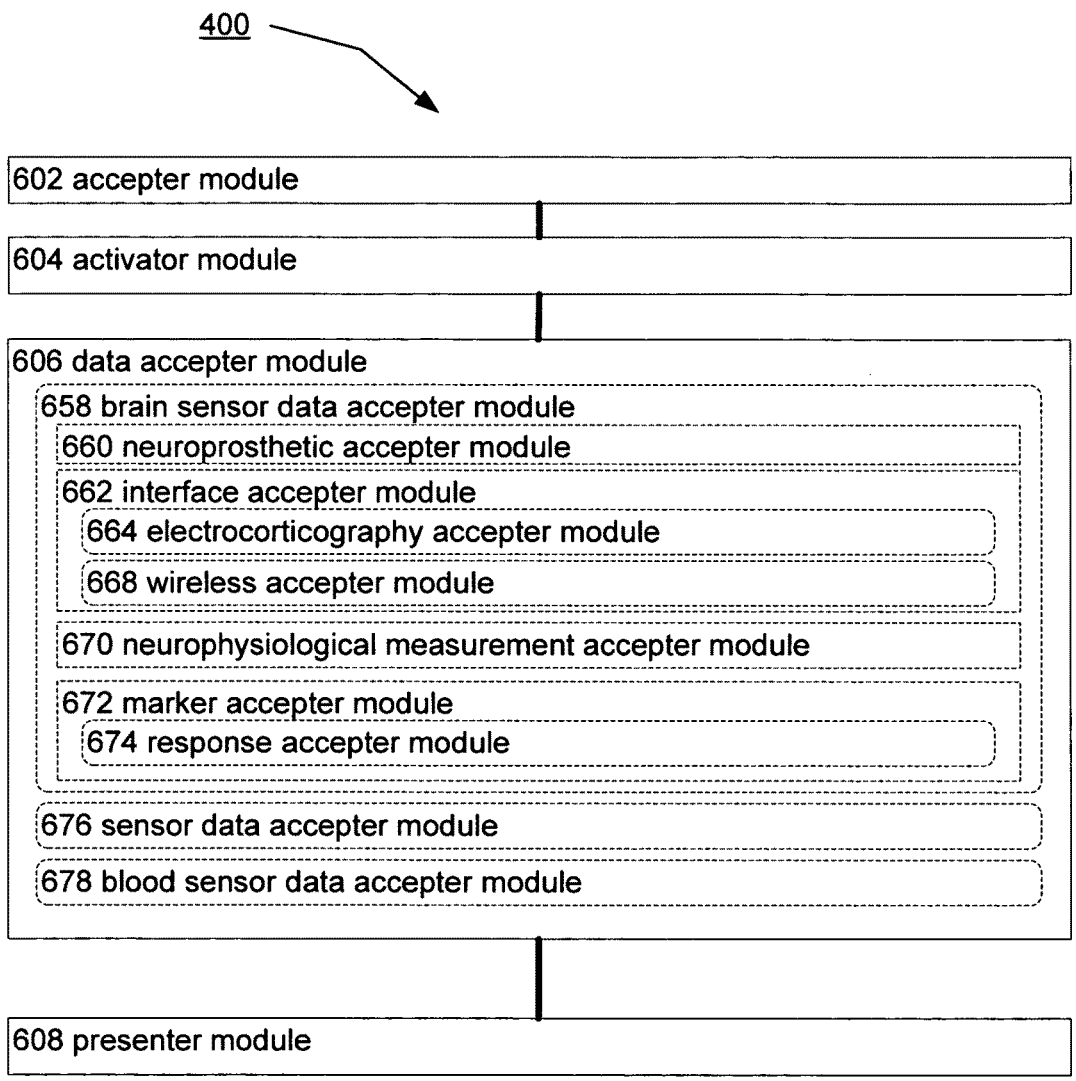
FIG. 7 illustrates certain alternative embodiments of the health services planning and matching system of FIG. 4.

FIG. 7 further illustrates system 400 including accepter module 602, activator module 604, data accepter module 606, and/or presenter module 608. Data accepter module 606 may include brain sensor data accepter module 658, sensor data accepter module 676, and/or blood sensor data accepter module 678. Brain sensor data accepter module 658 may include neuroprosthetic accepter module 660, interface accepter module 662, neurophysiological measurement accepter module 670, and/or marker accepter module 672. Interface accepter module 662 may include electrocorticography accepter module 664 and/or wireless accepter module 668. Marker accepter module 672 may include response accepter module 674.

Figure 8:
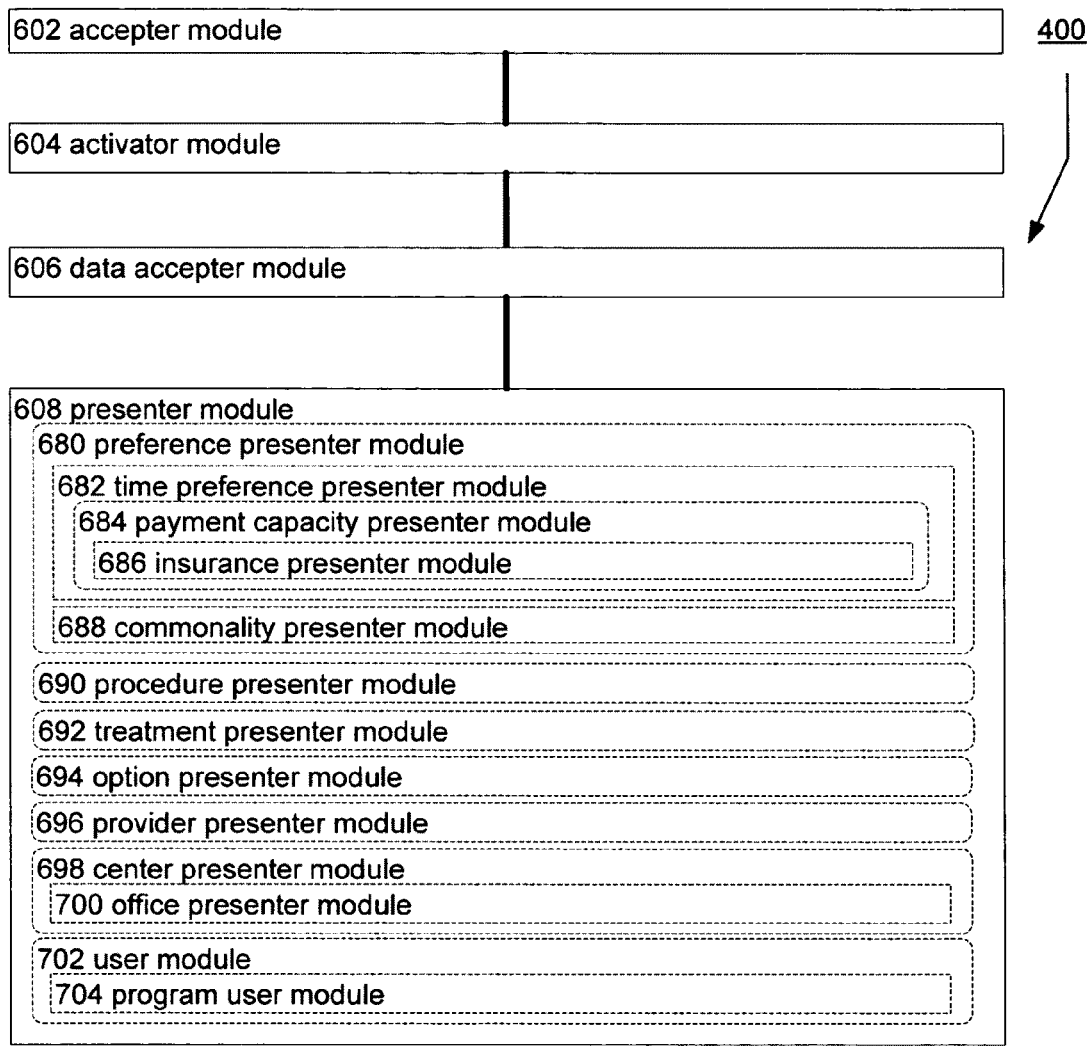
FIG. 8 illustrates certain alternative embodiments of the health services planning and matching system of FIG. 4.

FIG. 8 further illustrates system 400 including accepter module 602, activator module 604, data accepter module 606, and/or presenter module 608. Presenter module 606 may include preference presenter module 680, procedure presenter module 690, treatment presenter module 692, option presenter module 694, provider presenter module 696, center presenter module 698, and/or user module 702. Preference presenter module 680 may include time preference presenter module 682 and/or commonality presenter module 688. Time preference presenter module 682 may include payment capacity presenter module 684. Payment capacity presenter module 684 may include insurance presenter module 686. Center presenter module 698 may include office presenter module 700. User module 702 may include program user module 704.

Figure 9:
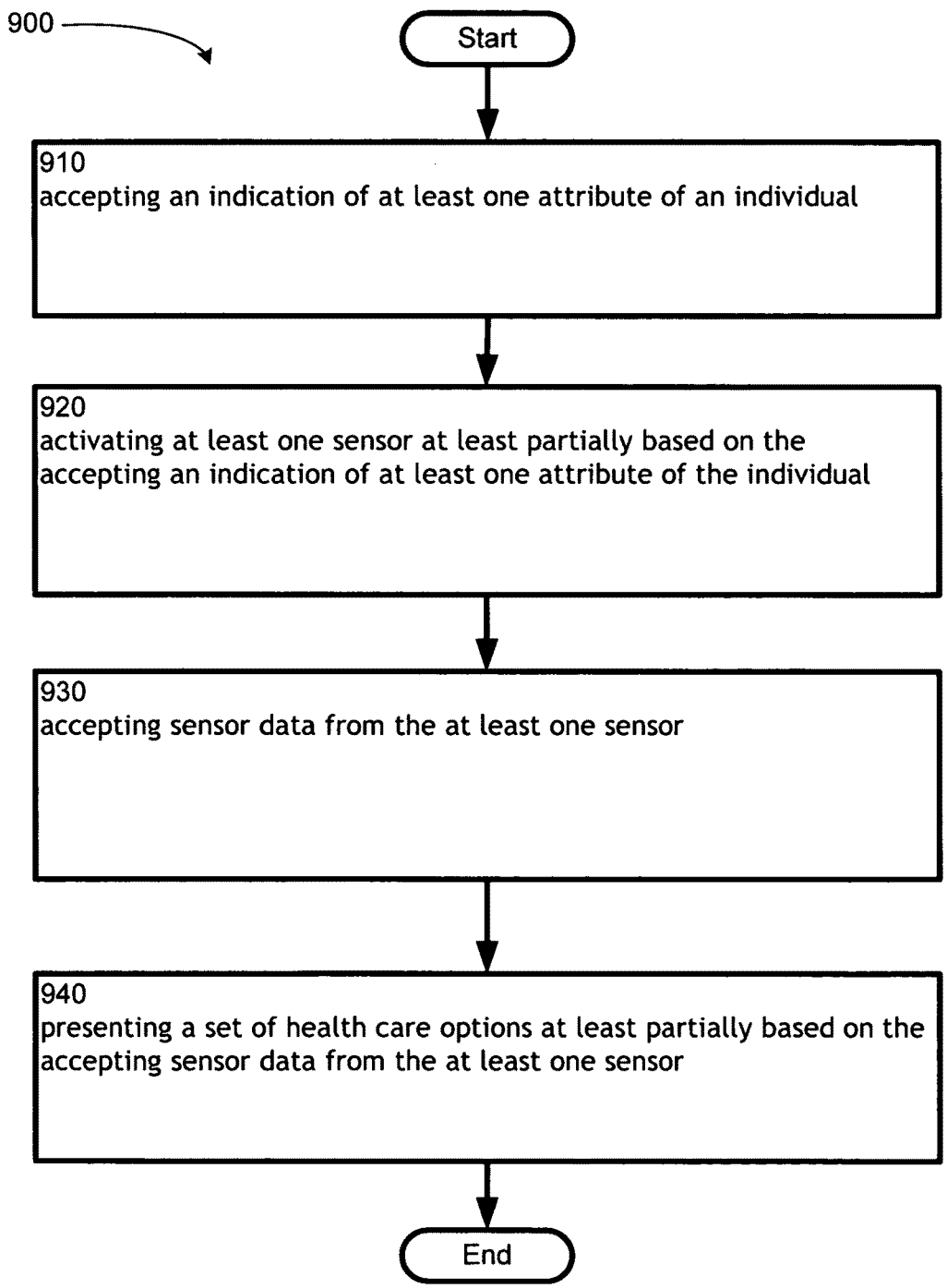
FIG. 9 illustrates an example of an operational flow representing example operations related to health services planning and matching, which may serve as a context for introducing one or more processes and/or devices described herein.

FIG. 9 illustrates an operational flow 900 representing example operations related to accepting an indication of at least one attribute of an individual, activating at least one sensor at least partially based on the accepting an indication of at least one attribute of the individual, accepting sensor data from the at least one sensor, and presenting a set of health care options at least partially based on the accepting sensor data from the at least one sensor. In FIG. 9 and in following figures that include various examples of operational flows, discussion and explanation may be provided with respect to the above-described examples of FIGS. 4 through 8, and/or with respect to other examples and contexts. However, it should be understood that the operational flows may be executed in a number of other environments and contexts, and/or in modified versions of FIGS. 4 through 8. Also, although the various operational flows are presented in the sequence(s) illustrated, it should be understood that the various operations may be performed in other orders than those which are illustrated, or may be performed concurrently.

After a start operation, the operational flow 900 moves to operation 910. Operation 910 depicts accepting an indication of at least one attribute of an individual. For example, as shown in FIGS. 4 through 8, accepter module 602 can accept at least one attribute of an individual. In an embodiment, accepter module 602 may accept a personal medical history, for example, that includes an individual's history of epileptic episodes. Accepting at least one attribute of an individual may serve to better indicate an individual's medical status to a health care provider, for example. Some other examples of an attribute of an individual may include results from a patient interview, results from an individual's input into, for example, a computer station, and/or a medical history. In some instances, accepter module 602 may include a computer processor.

Then, operation 920 depicts activating at least one sensor at least partially based on the accepting an indication of at least one attribute of the individual. For example, as shown in FIGS. 4 through 8, activator module 604 can activate at least one sensor at least partially based on the accepting an indication of at least one attribute of the individual. For example, activator module 604 may activate an array of epilepsy sensors configured to monitor an individual's heart rate and breathing patterns to detect an oncoming epileptic seizure. An example of an epilepsy sensor may include the epilepsy sensor available from Tunstall Group Limited, Whitley Bridge, Yorkshire, United Kingdom. Some additional examples of a sensor may include a movement sensor, a glucose sensor, an oxygen sensor, a chemical sensor, a thermometer, an optical sensor, and/or a biochip. In some instances, activator module 604 may include a computer processor.

Then, operation 930 depicts accepting sensor data from the at least one sensor. For example, as shown in FIGS. 4 through 8, data accepter module 606 can accept sensor data from the at least one sensor. In an embodiment, data accepter module 606 may accept data from the array of epilepsy sensors such as those disclosed above. Accepting sensor data may serve to further validate or invalidate the accepted indication of an individual's attribute. Some examples of a sensor may include a movement sensor, a glucose sensor, an oxygen sensor, a chemical sensor, a thermometer, an optical sensor, and/or a biochip. In some instances, data accepter module 606 may include a computer processor.

Then, operation 940 depicts presenting a set of health care options at least partially based on the accepting sensor data from the at least one sensor. For example, as shown in FIGS. 4 through 8, presenter module 608 can present a set of health care options at least partially based on the accepting sensor data from the at least one sensor. In one embodiment, presenter module 608 may, based on at least one accepted attribute of an individual and accepted sensor data, present a set of health care options according to one or more diagnoses and/or treatment paths corresponding to symptom(s) or conditions indicated by the accepted attribute(s) of an individual and accepted sensor data. Some examples of presenting a plurality of health service options may include presenting at least one physician, medication, exercise, health care facility, and/or medical procedure. In an embodiment, presenter module 608 may present a list of physicians specializing in the treatment of epilepsy and a list of health care facilities that are able to accommodate the individual. In some instances, presenter module 608 may include a computer processor.

Figure 10:
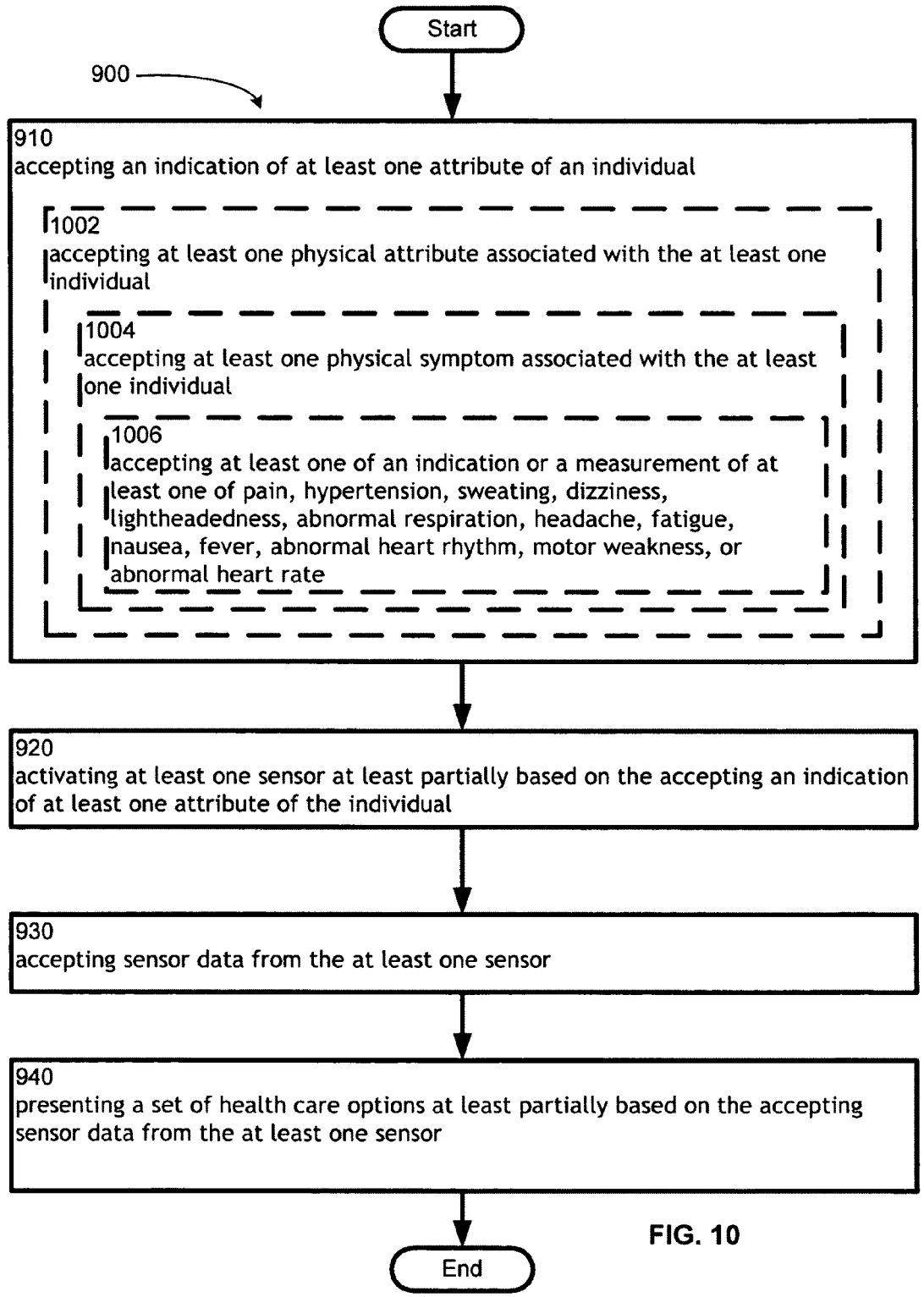
FIG. 10 illustrates an alternative embodiment of the operational flow of FIG. 9.

FIG. 10 illustrates alternative embodiments of the example operational flow 900 of FIG. 9. FIG. 10 illustrates example embodiments where operation 910 may include at least one additional operation. Additional operations may include operation 1002, operation 1004, and/or operation 1006.

Operation 1002 illustrates accepting at least one physical attribute associated with the at least one individual. For example, as shown in FIGS. 4 through 8, physical attribute accepter module 610 can accept at least one physical attribute associated with the at least one individual. In one instance, physical attribute accepter module 610 can accept a physical attribute associated with an individual, for example a weight history. A physical attribute may include an attribute that may be described and/or detected using senses, that has substance and/or a material existence, and/or that may be acted upon by physical force. Some examples of a physical attribute may include a biochemical measurement such as blood sugar level, an appearance, and/or a physiological measurement such as blood pressure, and/or skin conductivity. In some instances, physical attribute accepter module 610 may include a computer processor.

Further, operation 1004 illustrates accepting at least one physical symptom associated with the at least one individual. For example, as shown in FIGS. 4 through 8, physical symptom accepter module 612 can accept at least one physical symptom associated with the at least one individual. In one example, physical symptom accepter module 612 can accept from an individual and/or user interface a physical symptom, for example an indication of influenza (e.g., a fever). A physical symptom may include a manifestation, sign, and/or an indication of the presence of a disease and/or some other bodily disorder and/or abnormality. Some examples of a physical symptom may include pain, swelling, fever, rash, and/or discoloration. In some instances, physical symptom accepter module 612 may include a computer processor.

Further, operation 1006 illustrates accepting at least one of an indication or a measurement of at least one of pain, hypertension, sweating, dizziness, lightheadedness, abnormal respiration, headache, fatigue, nausea, fever, abnormal heart rhythm, motor weakness, or abnormal heart rate. For example, as shown in FIGS. 4 through 8, physical measurement accepter module 614 can accept at least one of an indication or a measurement of at least one of pain, hypertension, sweating, dizziness, lightheadedness, abnormal respiration, headache, fatigue, nausea, fever, abnormal heart rhythm, motor weakness, or abnormal heart rate. In one example, physical measurement accepter module 614 can accept an indication of an individual's pain and a measurement of high blood pressure from a patient interview. Pain may include a sensation of somatic hurt or disorder and may include acute pain and/or chronic pain. Hypertension may include chronically elevated blood pressure and may be considered to be present when a person's systolic blood pressure is consistently about 140 mm Hg or greater and/or their diastolic blood pressure is consistently about 90 mm Hg or greater. Sweating may include the excessive production and/or evaporation of fluid excreted by the sweat glands in the skin. Dizziness may include vertigo, disequilibrium, pre-syncope, and/or other balance disorders. Lightheadedness may include a sensation of dizziness and/or fainting. Abnormal respiration may include atypical and/or pathological breathing patterns. Headache may include pain in the head, neck, and/or upper back and may be a symptom of tension, migraine, dehydration, eye strain, sinus disorders, and/or low blood sugar. Fatigue may include muscle weakness and/or lack of strength. Nausea may include the sensation of unease and/or discomfort in the stomach, often with the urge to vomit. Fever may include an increase in internal body temperature to levels above normal. Abnormal heart rhythm may include inconsistent and/or irregular rhythmic contractions in the heart such as sick sinus syndrome, atrial fibrillation, and/or atrial flutter. Motor weakness may include a lack of strength and/or function in the portion of the central nervous system involved in movement. An abnormal heart rate may include an irregular heart contraction frequency such as bradycardia, tachycardia or the like. In some instances, physical measurement accepter module 614 may include a computer processor.

Figure 11:
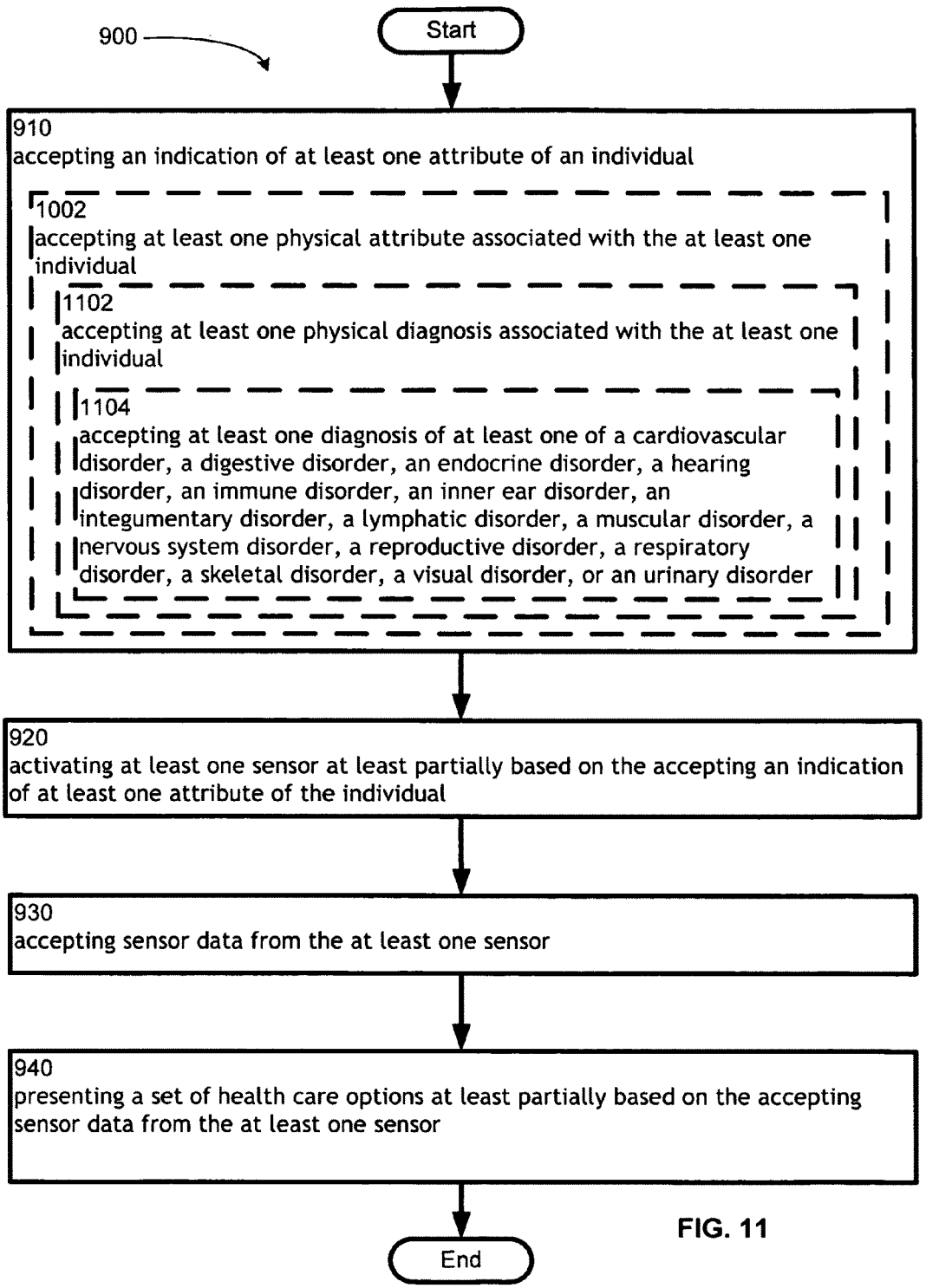
FIG. 11 illustrates an alternative embodiment of the operational flow of FIG. 9.

FIG. 11 illustrates alternative embodiments of the example operational flow 900 of FIG. 9. FIG. 11 illustrates example embodiments where operation 910 may include at least one additional operation. Additional operations may include operation 1102 and/or operation 1104.

Further, operation 1102 illustrates accepting at least one physical diagnosis associated with the at least one individual. For example, as shown in FIGS. 4 through 8, physical diagnosis accepter module 616 can accept at least one physical diagnosis associated with the at least one individual. In a specific example, physical diagnosis accepter module 616 may accept from a memory device a physical diagnosis of epilepsy associated with the individual. A physical diagnosis may include identifying a disease and/or condition by its outward signs and/or symptoms. Some other examples of a physical diagnosis may include identifying influenza and/or identifying Alzheimer's disease. In some instances, physical diagnosis accepter module 616 may include a computer processor.

Further, operation 1104 illustrates accepting at least one diagnosis of at least one of a cardiovascular disorder, a digestive disorder, an endocrine disorder, a hearing disorder, an immune disorder, an inner ear disorder, an integumentary disorder, a lymphatic disorder, a muscular disorder, a nervous system disorder, a reproductive disorder, a respiratory disorder, a skeletal disorder, a visual disorder, or an urinary disorder. For example, as shown in FIGS. 4 through 8, physical disorder accepter module 618 can accept at least one diagnosis of at least one of a cardiovascular disorder, a digestive disorder, an endocrine disorder, a hearing disorder, an immune disorder, an inner ear disorder, an integumentary disorder, a lymphatic disorder, a muscular disorder, a nervous system disorder, a reproductive disorder, a respiratory disorder, a skeletal disorder, a visual disorder, or an urinary disorder. In a specific instance, physical disorder accepter module 618 can accept from a user interface a diagnosis of a respiratory disorder. A cardiovascular disorder may include a disorder associated with the circulatory system including the pumping and channeling of blood to and from the body and lungs with the heart, the blood, and the blood vessels. Examples of a circulatory disorder include high blood pressure, coronary heart disease, atherosclerosis, or the like. A digestive disorder may include a disorder associated with the esophagus, the stomach, the liver, the gallbladder, the pancreas, the intestines, the rectum, the anus, and/or the digestive system including digestion and processing food with salivary glands. Examples of a digestive disorder include GERD, Crohn's disease, IBS, or the like. An endocrine disorder may include a disorder associated with the endocrine system including the pancreas, the pituitary gland, the pineal body and/or the pineal gland, the thyroid, the parathyroids, the adrenal glands, and/or communication within the body using hormones made by the endocrine glands, such as the hypothalamus. Examples of an endocrine disorder include diabetes, acromegaly, or the like. A hearing disorder may include a full or partial decrease in the ability to detect or understand sounds. Some examples of a hearing disorder may include otosclerosis, deafness, and/or unilateral hearing loss. An immune disorder may include a dysfunction of the immune system. Examples of an immune disorder may include an immunodeficiency, such as malfunctioning lymphocytes; autoimmunity, such as Coeliac disease and/or autoimmune hepatitis; and/or hypersensitivity, such as asthma. An inner ear disorder may include a balance disorder, such as vertigo, disequilibrium, and/or pre-syncope. An integumentary disorder may include a disorder associated with the integumentary system including the skin, hair, and/or nails, such as psoriasis, eczema, dermatitis, or the like. A lymphatic disorder may include a disorder associated with the lymphatic system including structures involved in the transfer of lymph between tissues and the blood stream and/or the lymph and the nodes and vessels that transport lymph including the immune system, including defending against disease-causing agents with leukocytes, and/or including the tonsils, the adenoids, the thymus, and/or the spleen. Examples of a lymphatic disorder include lymphedema, lymphadenopathy, or the like. A muscle disorder may include a disorder associated with the muscular system including the structure and/or movement of muscles. Examples of a muscle disorder include muscular dystrophy, myasthenia gravis, an injury, such as a strain, or the like. A nervous system disorder may include a disorder associated with the nervous system including collecting, transferring, and/or processing information with the brain, the spinal cord, the peripheral nerves, and/or the nerves. Examples of a nervous system disorder include multiple sclerosis, fibromyalgia, carpal tunnel syndrome, or the like. A reproductive disorder may include a disorder associated with the reproductive system including the sex organs, such as ovaries, fallopian tubes, the uterus, the vagina, mammary glands, testes, the vas deferens, seminal vesicles, the prostate, and/or the penis. Examples of a reproductive disorder include erectile dysfunction, endometriosis, fibroids, or the like. A respiratory disorder may include a disorder associated with the respiratory system including the organs used for breathing, the pharynx, the larynx, the trachea, the bronchi, the lungs, and/or the diaphragm. Examples of a respiratory disorder include emphysema, asthma, or the like. A skeletal disorder may include a disorder associated with the skeletal system including the structural support and protection with bones, cartilage, ligaments, and/or tendons. Examples of a skeletal disorder include osteoporosis, arthritis, tendonitis, a skeletal injury, such as a bone fracture, or the like. A visual disorder may include a disease, impairment, and/or lack of function in the eye and/or in visual perception. Some examples of a visual disorder may include amblyopia, macular degeneration, glaucoma, and/or blindness. A urinary disorder may include a disorder associated with the urinary system including the kidneys, the ureters, the bladder and/or urethra involved in fluid balance, electrolyte balance and/or the excretion of urine. Examples of a urinary disorder include bladder dysfunction, kidney disease, bladder or urethra infection, or the like. In some instances, physical disorder accepter module 618 may include a computer processor.

Figure 12:
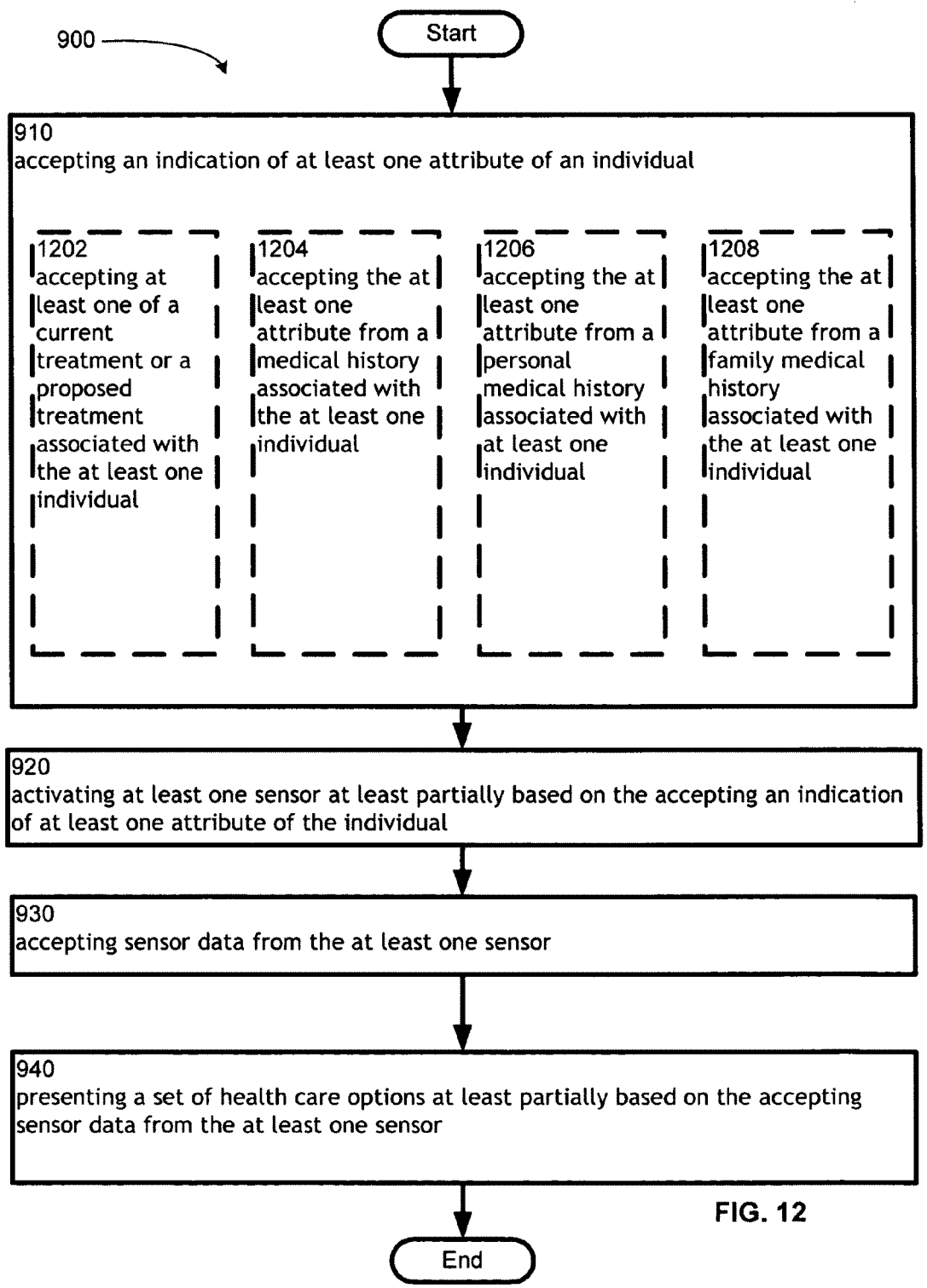
FIG. 12 illustrates an alternative embodiment of the operational flow of FIG. 9.

FIG. 12 illustrates alternative embodiments of the example operational flow 900 of FIG. 9. FIG. 12 illustrates example embodiments where operation 910 may include at least one additional operation. Additional operations may include operation 1202, operation 1204, operation 1206, and/or operation 1208.

Operation 1202 illustrates accepting at least one of a current treatment or a proposed treatment associated with the at least one individual. For example, as shown in FIGS. 4 through 8, treatment accepter module 620 can accept at least one of a current treatment or a proposed treatment associated with the at least one individual. In one instance, treatment accepter module 620 may accept a current treatment regime associated with a certain individual. A current treatment may include one or a series of treatments recommended, administered, and/or prescribed for a certain individual. A proposed treatment may include one or a series of treatments recommended, prescribed, and/or not currently administered to a certain individual. In some instances, treatment accepter module 620 may include a computer processor.

Operation 1204 illustrates accepting the at least one attribute from a medical history associated with the at least one individual. For example, as shown in FIGS. 4 through 8, history accepter module 622 can accept the at least one attribute from a medical history associated with the at least one individual. In one example, history accepter module 622 may accept an attribute from a medical history including a record of diabetes therapy associated with a specific individual. A medical history may include a list of previous illnesses, symptoms, medicines, treatments, health risk factors, operations, and/or doctor visits for an individual and/or a relation of an individual. In some instances, history accepter module 622 may include a computer processor.

Operation 1206 illustrates accepting the at least one attribute from a personal medical history associated with at least one individual. For example, as shown in FIGS. 4 through 8, personal history accepter module 624 can accept the at least one attribute from a personal medical history associated with at least one individual. In an embodiment, personal history accepter module 624 may accept an attribute including, for example, a list of surgeries from a personal medical history associated with a specific individual. A personal medical history may include a list of previous illnesses, symptoms, medicines, treatments, health risk factors, operations, and/or doctor visits associated with at least one individual. A personal and/or a family medical history may include life history and/or social history characteristics such as smoking, drinking, drug use, sexual history, exercise history, eating history, nutraceutical history, or the like. In some instances, personal history accepter module 624 may include a computer processor.

Operation 1208 illustrates accepting the at least one attribute from a family medical history associated with the at least one individual. For example, as shown in FIGS. 4 through 8, family history accepter module 626 can accept the at least one attribute from a family medical history associated with the at least one individual. In an example, family history accepter module 626 may accept an attribute including a list of family members that have had epilepsy from a family medical history associated with a specific individual. A family medical history may include a list of previous illnesses, symptoms, medicines, treatments, health risk factors, operations, and/or doctor visits associated with family members related to the at least one individual. In some instances, family history accepter module 626 may include a computer processor.

Figure 13:
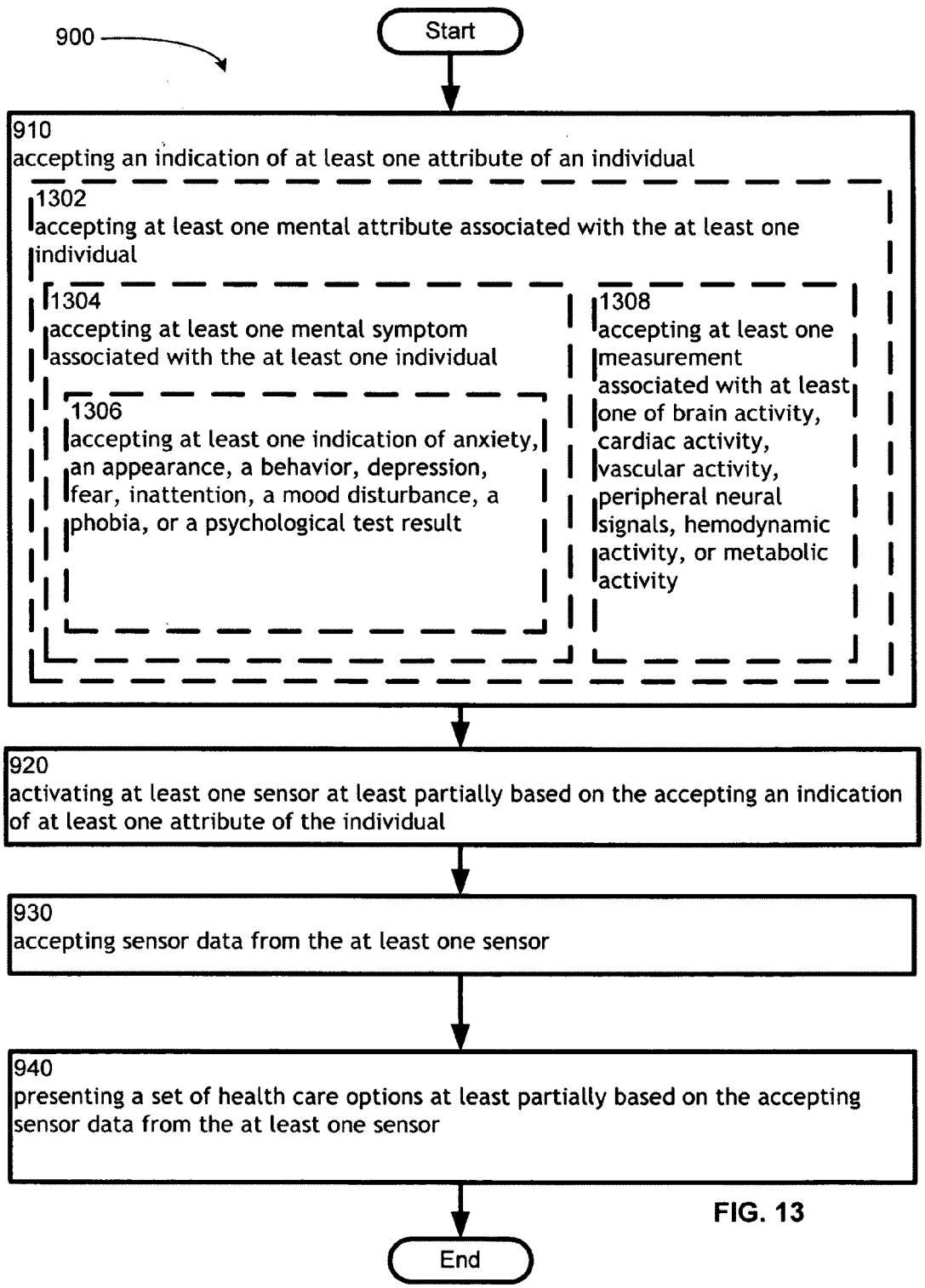
FIG. 13 illustrates an alternative embodiment of the operational flow of FIG. 9.

FIG. 13 illustrates alternative embodiments of the example operational flow 900 of FIG. 9. FIG. 13 illustrates example embodiments where operation 910 may include at least one additional operation. Additional operations may include operation 1302, operation 1304, operation 1306, and/or operation 1308.

Operation 1302 illustrates accepting at least one mental attribute associated with the at least one individual. For example, as shown in FIGS. 1 through 2, mental attribute accepter module 628 can accept at least one mental attribute associated with the at least one individual. In one example, mental attribute accepter module 628 may accept a mental attribute including, for example, an indication of a learning disability associated with a specific individual. A mental attribute may include an attribute that may be related to and/or associated with basic mental function and/or high-level brain function. Some examples of a mental attribute may include an indication of cognitive disability, measurements of brain activity, for example using functional MRI or near infra-red technology, and/or measurements of mental development. In some instances, mental attribute accepter module 628 may include a computer processor.

Further, operation 1304 illustrates accepting at least one mental symptom associated with the at least one individual. For example, as shown in FIGS. 4 through 8, mental symptom accepter module 630 can accept at least one mental symptom associated with the at least one individual. In one example, mental symptom accepter module 630 may accept a mental symptom including a stress level measurement associated with a specific individual. A mental symptom may include a manifestation, sign, and/or an indication of the presence of a disease and/or some other mental disorder and/or abnormality. Some examples of a mental symptom may include lack of attention, indication of stress, hyperactivity, nervousness, and/or lack of responsiveness. In some instances, mental symptom accepter module 630 may include a computer processor.

Further, operation 1306 illustrates accepting at least one indication of anxiety, an appearance, a behavior, depression, fear, inattention, a mood disturbance, a phobia, or a psychological test result. For example, as shown in FIGS. 4 through 8, mental disorder accepter module 632 can accept at least one indication of anxiety, an appearance, a behavior, depression, fear, inattention, a mood disturbance, a phobia, or a psychological test result. In one example, mental disorder accepter module 632 can accept from a user interface an indication of anxiety and depression. Anxiety may include feelings of fear, apprehension, and/or worry and may be accompanied by physical sensations. An appearance may include an outward, audible, and/or visible aspect of a person and/or thing associated with a person. A behavior may include the manner in which a person and/or thing associated with a person acts and/or reacts. Depression may include a mental state characterized by pessimism, a sense of inadequacy, despondence, despair, a low level of energy, and/or a lack of activity. Fear may be caused by impending danger, perceived evil, and/or pain, whether real or imagined. Inattention may include the failure of a person to focus attention. A mood disturbance may include a change in emotional state. A phobia may include an irrational, and/or persistent fear of certain situations, objects, activities, and/or people. A psychological test result may include a sample behavior for inferring a certain generalization about a person. For example, a personality test result may indicate that person has obsessive/compulsive characteristics. In some instances, mental disorder accepter module 632 may include a computer processor.

Further, operation 1308 illustrates accepting at least one measurement associated with at least one of brain activity, cardiac activity, vascular activity, peripheral neural signals, hemodynamic activity, or metabolic activity. For example, as shown in FIGS. 4 through 8, mental measurement accepter module 634 can accept at least one measurement associated with at least one of brain activity, cardiac activity, vascular activity, peripheral neural signals, hemodynamic activity, or metabolic activity. In one instance, mental measurement accepter module 634 can accept a measurement associated with brain activity. Brain activity may include the electrical activity of the brain, such as that measured by EEG, MEG, or the like. Other brain activity measurements may include functional MRI imaging, near infra-red imaging, PET scanning, or the like. Cardiac activity may include electrical activity in the heart, such as that measured by EKG or visual imaging. Vascular activity may include any activity and/or function of the circulatory system. Peripheral neural signals may include neural signals sent through the peripheral nervous system. Hemodynamic activity may include any activity associated with the circulatory system. Metabolic activity may include any activity associated with the biochemical reactions occurring in a living organism. In some instances, mental measurement accepter module 634 may include a computer processor.

Figure 14:
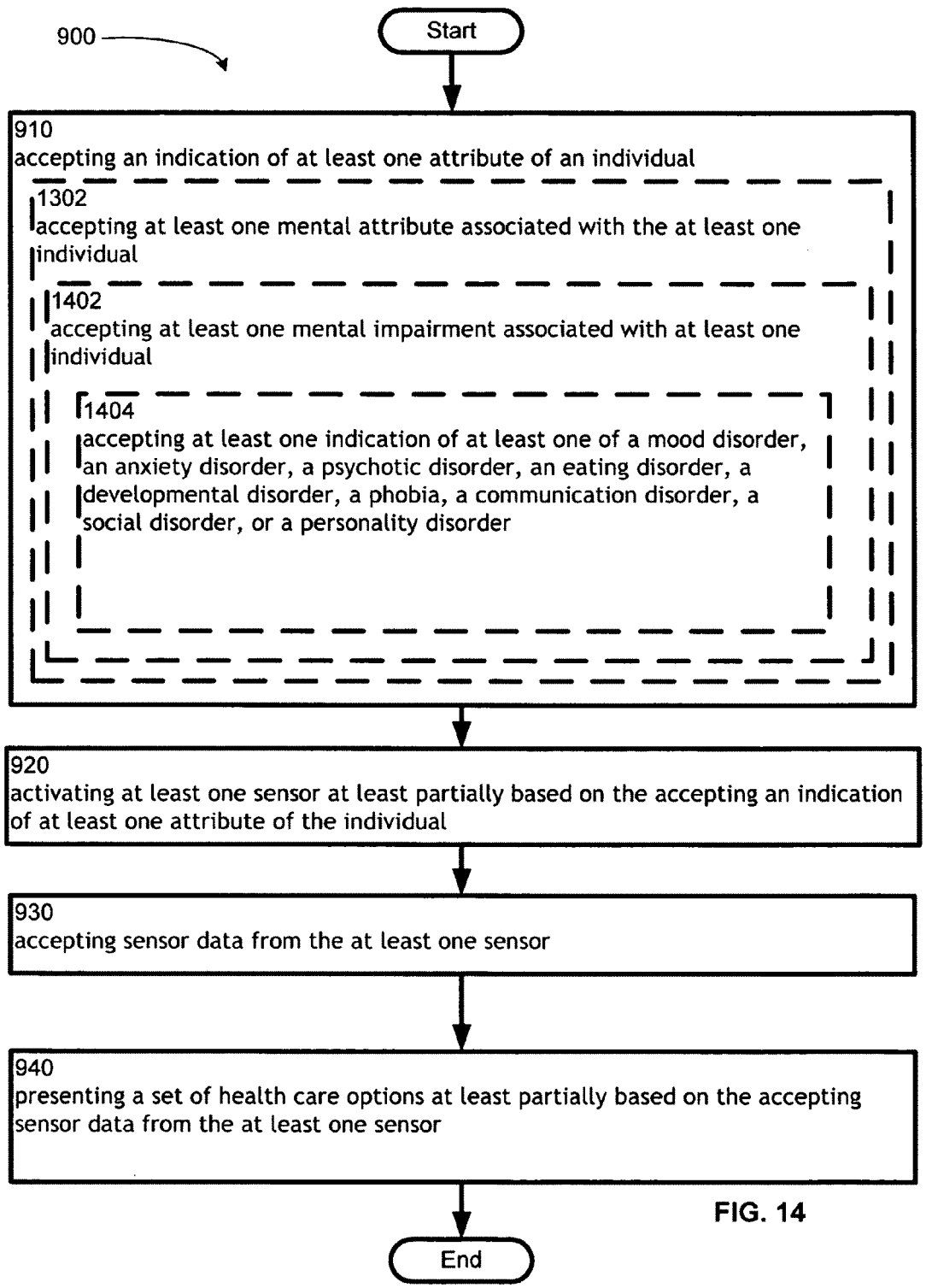
FIG. 14 illustrates an alternative embodiment of the operational flow of FIG. 9.

FIG. 14 illustrates alternative embodiments of the example operational flow 900 of FIG. 9. FIG. 14 illustrates example embodiments where operation 910 may include at least one additional operation. Additional operations may include operation 1402, and/or operation 1404.

Further, operation 1402 illustrates accepting at least one mental impairment associated with at least one individual. For example, as shown in FIGS. 4 through 8, mental impairment accepter module 636 can accept at least one mental impairment associated with at least one individual. In one example, mental impairment accepter module 636 can accept a mental impairment associated with a specific individual, for example depression. A mental impairment may include a condition or function judged by a health care provider to be significantly impaired relative to the usual standard of an individual of their group, and may include mental impairment, sensory impairment, and/or mental disease. In some instances, mental impairment accepter module 636 may include a computer processor.

Further, operation 1404 illustrates accepting at least one indication of at least one of a mood disorder, an anxiety disorder, a psychotic disorder, an eating disorder, a developmental disorder, a phobia, a communication disorder, a social disorder, or a personality disorder. For example, as shown in FIGS. 4 through 8, mental indication accepter module 638 can accept at least one indication of at least one of a mood disorder, an anxiety disorder, a psychotic disorder, an eating disorder, a developmental disorder, a phobia, a communication disorder, a social disorder, or a personality disorder. In one instance, mental indication accepter module 638 can accept from a user interface an indication of a mood disorder in a specific individual. A mood disorder may include a condition whereby the prevailing emotional mood is distorted or inappropriate to the circumstances, and may include examples such as bipolar disorder, an alteration in mood, and/or depression. An anxiety disorder may include nervous system disorders such as irrationality, illogical worry not based on fact, fear, and/or phobia. A psychotic disorder may include a state of mind in which thinking becomes irrational and/or disturbed and may include hallucinations, abnormal perception, mania, dementia, delusions and/or delusional beliefs, delirium, depression, psychosis personality disorder, personality changes, and/or disorganized thinking. An eating disorder may include a compulsion to eat and/or avoid eating that negatively affects physical and/or mental health. Some examples of an eating disorder may include anorexia nervosa and bulimia nervosa. A developmental disorder may include a disorder occurring in a child's development, which may retard development. Some examples of a developmental disorder may include an emotional disorder, a cognitive disorder, and/or a mental disorder accompanied by physical traits, such as Down syndrome. A phobia may include an irrational, intense, and/or persistent fear of certain situations, objects, activities, and/or persons. Examples of phobias include social phobias, arachnophobia, xenophobia, and/or claustrophobia. A communication disorder may include a disease and/or a condition partially or totally preventing human communication. Some examples of a communication disorder may include autism, stuttering, and/or aphasia. A social disorder may include a condition characterized by a difficulty in human interaction and/or emotional discomfort in social situations. Some examples of a social disorder may include stage fright, social anxiety disorder, and/or shyness. A personality disorder may include a disorder characterized by pathological trends in personality structure. Some examples of a personality disorder may include a paranoid personality disorder, a narcissistic personality disorder, and/or an obsessive-compulsive personality disorder. In some instances, mental indication accepter module 638 may include a computer processor.

Figure 15:
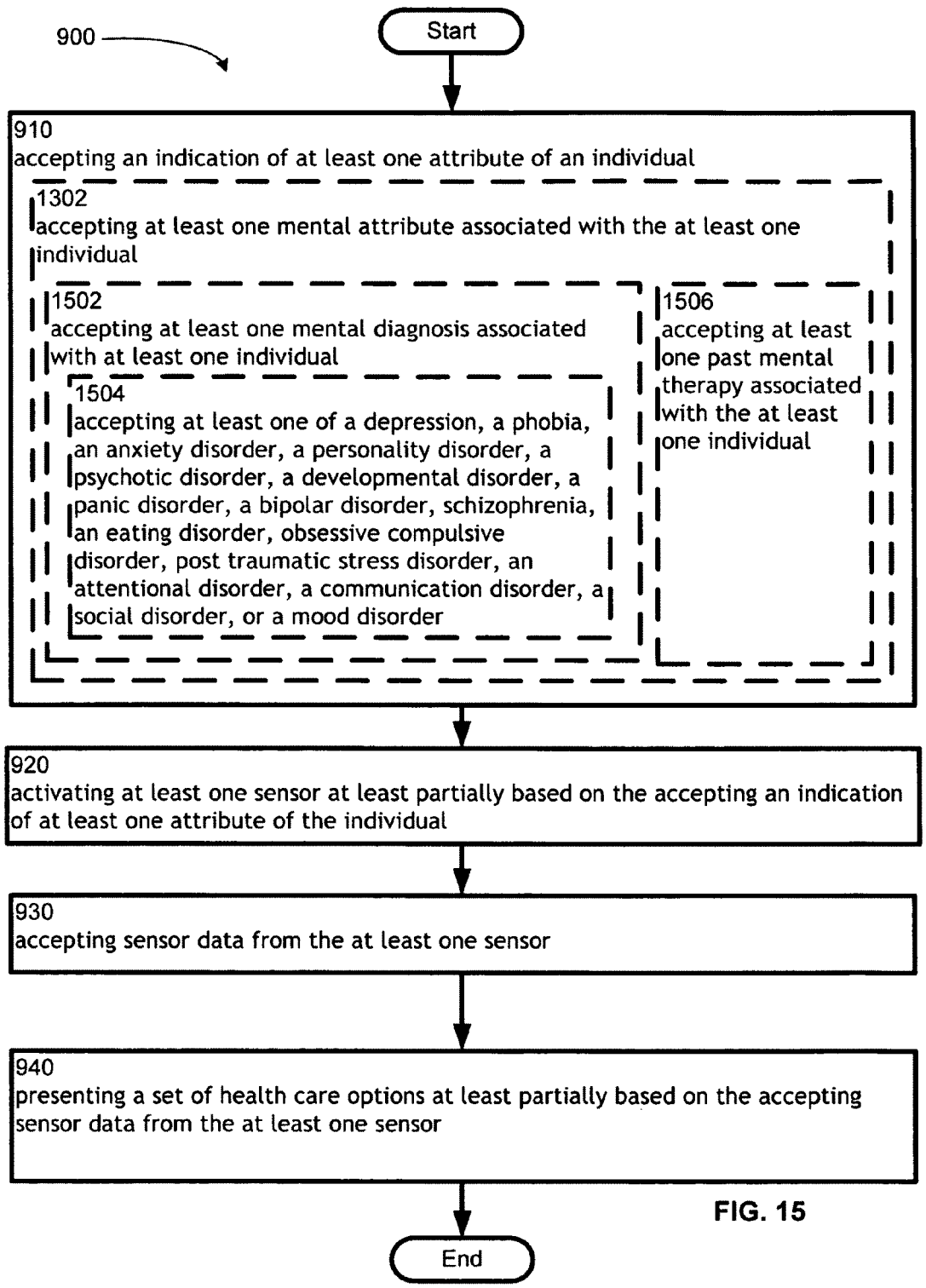
FIG. 15 illustrates an alternative embodiment of the operational flow of FIG. 9.

FIG. 15 illustrates alternative embodiments of the example operational flow 900 of FIG. 9. FIG. 15 illustrates example embodiments where operation 910 may include at least one additional operation. Additional operations may include operation 1502, operation 1504, and/or operation 1506.

Further, operation 1502 illustrates accepting at least one mental diagnosis associated with at least one individual. For example, as shown in FIGS. 4 through 8, mental diagnosis accepter module 640 can accept at least one mental diagnosis associated with at least one individual. In a specific instance, mental diagnosis accepter module 640 may accept a mental diagnosis including a phobia associated with a specific individual. A mental diagnosis may include identifying a mental disorder and/or condition by its symptoms. Some examples of a mental diagnosis may include a mood disorder such as depression, an anxiety disorder such as PTSD, a behavioral disorder such as ADHD, a personality disorder such as borderline personality disorder, and/or a phobia. Mental disorders may include those listed in the Diagnostic and Statistical Manual of Mental Disorders (DSM). In some instances, mental diagnosis accepter module 640 may include a computer processor.

Further, operation 1504 illustrates accepting at least one of a depression, a phobia, an anxiety disorder, a personality disorder, a psychotic disorder, a developmental disorder, a panic disorder, a bipolar disorder, schizophrenia, an eating disorder, obsessive compulsive disorder, post traumatic stress disorder, an attentional disorder, a communication disorder, a social disorder, or a mood disorder. For example, as shown in FIGS. 4 through 8, mental condition accepter module 642 can accept at least one of a depression, a phobia, an anxiety disorder, a personality disorder, a psychotic disorder, a developmental disorder, a panic disorder, a bipolar disorder, schizophrenia, an eating disorder, obsessive compulsive disorder, post traumatic stress disorder, an attentional disorder, a communication disorder, a social disorder, or a mood disorder. In one example, mental condition accepter module 642 may accept a diagnosis of depression. Depression may include a mental state characterized by a pessimistic sense of inadequacy and/or a despondent lack of activity. A phobia may include an irrational, intense, and/or persistent fear of certain situations, objects, activities, and/or persons. Some phobias may include social phobias, arachnophobia, xenophobia, and/or claustrophobia. An anxiety disorder may include nervous system disorders such as irrationality, illogical worry not based on fact, fears, and/or phobias. A personality disorder may include a disorder characterized by pathological trends in personality structure. Some examples of a personality disorder may include a paranoid personality disorder, a narcissistic personality disorder, and/or an obsessive-compulsive personality disorder. A psychotic disorder may include a state of mind in which thinking becomes irrational and/or disturbed and may include hallucinations, delusional beliefs, personality changes, and/or disorganized thinking. A developmental disorder may include a disorder occurring in a child's development, which may often retard development.

Some examples of a developmental disorder may include psychological or physical disorders. A panic disorder may include a condition characterized by recurring panic attacks in combination with significant behavioral change. A bipolar disorder may include a mood disorder characterized by the presence of one or more episodes of abnormally elevated mood, such as Bipolar I disorder, Bipolar II disorder, cyclothymia, and/or Bipolar-NOS. Schizophrenia may include a mental illness characterized by impairments in the perception or expression of reality, most commonly manifesting as auditory hallucinations, paranoid or bizarre delusions or disorganized speech and thinking in the context of significant social or occupational dysfunction. An eating disorder may include a compulsion to eat or avoid eating, such as anorexia nervosa and/or bulimia nervosa. Obsessive compulsive disorder may include a psychiatric anxiety disorder characterized by obsessive, distressing, intrusive thoughts and related compulsions which attempt to neutralize the obsessions. Post traumatic stress disorder may include an anxiety disorder that can develop after exposure to one or more terrifying events in which grave physical harm occurred or was threatened. An attentional disorder may include a persistent pattern of inattention and/or hyperactivity, as well as forgetfulness, poor impulse control or impulsivity, and distractibility, such as attention-deficit hyperactivity disorder (ADHD). A communication disorder may include a disease and/or a condition partially or totally preventing human communication. Some examples of a communication disorder may include autism, stuttering, and/or aphasia. A social disorder may include a condition characterized by a difficulty in human interaction and/or emotional discomfort in social situations. Some examples of a social disorder may include stage fright, social anxiety disorder, and/or shyness. A mood disorder may include a condition whereby the prevailing emotional mood is distorted or inappropriate to the circumstances and may include examples such as bipolar disorder and/or depression. In some instances, mental condition accepter module 642 may include a computer processor.

Further, operation 1506 illustrates accepting at least one past mental therapy associated with the at least one individual. For example, as shown in FIGS. 4 through 8, mental therapy accepter module 644 can accept at least one past mental therapy associated with the at least one individual. In one instance, mental therapy accepter module 644 can accept an indication of a past mental therapy associated with a specific individual. A past mental therapy may include a list and/or a record of at least one mental therapy, such as an anti-depressant medication, administered to at least one individual. In some instances, mental therapy accepter module 644 may include a computer processor.

Figure 16:
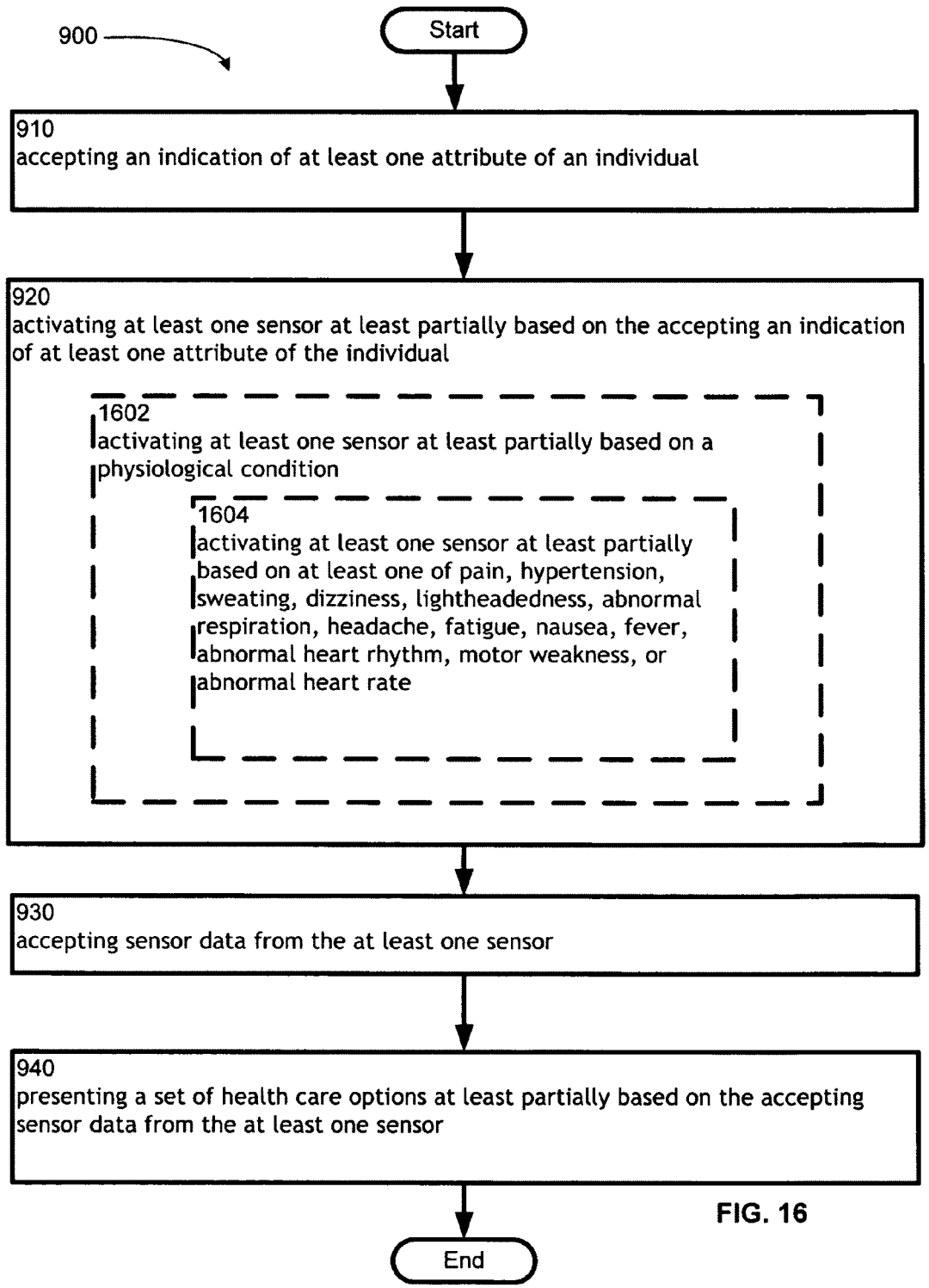
FIG. 16 illustrates an alternative embodiment of the operational flow of FIG. 9.

FIG. 16 illustrates alternative embodiments of the example operational flow 900 of FIG. 9. FIG. 16 illustrates example embodiments where operation 920 may include at least one additional operation. Additional operations may include operation 1602, and/or operation 1604.

Operation 1602 illustrates activating at least one sensor at least partially based on a physiological condition. For example, as shown in FIGS. 4 through 8, condition activator module 646 can activate at least one sensor at least partially based on a physiological condition. In an embodiment, condition activator module 646 may activate an epilepsy sensor based on an individual's breathing rate, blood pressure, and/or heart rate. Activation of a sensor based on a physiological condition may serve to anticipate a disease and/or condition, such as an oncoming epileptic seizure. Additionally, activating a sensor may serve to collect complete information, for example regarding an epileptic seizure. An additional example of activating a sensor based on a physiological condition may be found in Greiner et al., U.S. Patent Publication No. 2009/0118595, which is incorporated herein by reference. In some instances, condition activator module 646 may include a computer processor.

Further, operation 1604 illustrates activating at least one sensor at least partially based on at least one of pain, hypertension, sweating, dizziness, lightheadedness, abnormal respiration, headache, fatigue, nausea, fever, abnormal heart rhythm, motor weakness, or abnormal heart rate. For example, as shown in FIGS. 4 through 8, physical condition activator module 648 can activate at least one sensor at least partially based on at least one of pain, hypertension, sweating, dizziness, lightheadedness, abnormal respiration, headache, fatigue, nausea, fever, abnormal heart rhythm, motor weakness, or abnormal heart rate. In an embodiment, physical condition activator module 648 may activate an array of sensors based on an indication of abnormal heart rate and headache. Pain may include a sensation of somatic hurt or disorder and may include acute pain and/or chronic pain. Hypertension may include chronically elevated blood pressure and may be considered to be present when a person's systolic blood pressure is consistently about 140 mm Hg or greater and/or their diastolic blood pressure is consistently about 90 mm Hg or greater. Sweating may include the excessive production and/or evaporation of fluid excreted by the sweat glands in the skin. Dizziness may include vertigo, disequilibrium, pre-syncope, and/or other balance disorders. Lightheadedness may include a sensation of dizziness and/or fainting. Abnormal respiration may include atypical and/or pathological breathing patterns. Headache may include pain in the head, neck, and/or upper back and may be a symptom of tension, migraine, dehydration, eye strain, sinus disorders, and/or low blood sugar. Fatigue may include muscle weakness and/or lack of strength. Nausea may include the sensation of unease and/or discomfort in the stomach, often with the urge to vomit. Fever may include an increase in internal body temperature to levels above normal. Abnormal heart rhythm may include inconsistent and/or irregular rhythmic contractions in the heart such as sick sinus syndrome, atrial fibrillation, and/or atrial flutter. Motor weakness may include a lack of strength and/or function in the portion of the central nervous system involved in movement. An abnormal heart rate may include an irregular heart contraction frequency such as bradycardia, tachycardia or the like. In some instances, physical condition activator module 648 may include a computer processor.

Figure 17:
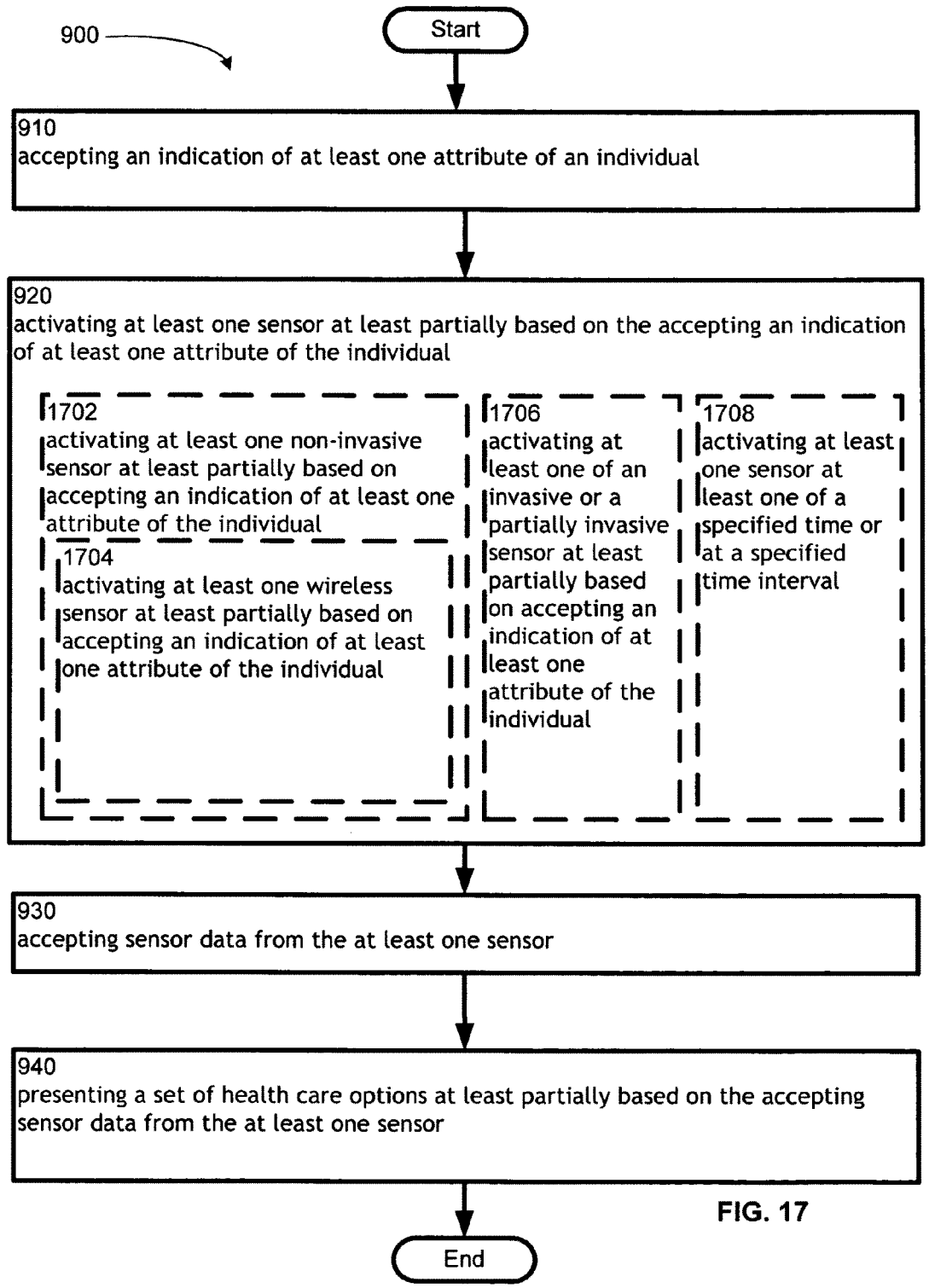
FIG. 17 illustrates an alternative embodiment of the operational flow of FIG. 9.

FIG. 17 illustrates alternative embodiments of the example operational flow 900 of FIG. 9. FIG. 17 illustrates example embodiments where operation 920 may include at least one additional operation. Additional operations may include operation 1702, operation 1704, operation 1706, and/or operation 1708.

Operation 1702 illustrates activating at least one non-invasive sensor at least partially based on accepting an indication of at least one attribute of the individual. For example, as shown in FIGS. 4 through 8, non-invasive activator module 650 can activate at least one non-invasive sensor at least partially based on accepting an indication of at least one attribute of the individual. In an embodiment, non-invasive activator module 650 may activate an array of sensors located on an individual's body configured to sense, for example, an ECG. Another example of activating a non-invasive sensor may be found in Falck, U.S. Patent Publication No. 2009/0023391, which is incorporated herein by reference. In some instances, non-invasive activator module 650 may include a computer processor.

Further, operation 1704 illustrates activating at least one wireless sensor at least partially based on accepting an indication of at least one attribute of the individual. For example, as shown in FIGS. 4 through 8, wireless activator module 652 can activate at least one wireless sensor at least partially based on accepting an indication of at least one attribute of the individual. In an embodiment, wireless activator module 652 may activate an array of sensors that wirelessly communicate with wireless activator module 652. Some wireless communication networks may include the use of Wi-Fi and/or Bluetooth systems, for example. Other wireless communication networks may use radio frequencies, microwave frequencies, and/or infrared (IR) shortrange communication. In some instances, wireless activator module 652 may include a computer processor.

Operation 1706 illustrates activating at least one of an invasive or a partially invasive sensor at least partially based on accepting an indication of at least one attribute of the individual. For example, as shown in FIGS. 4 through 8, invasive activator module 654 can activate at least one of an invasive or a partially invasive sensor at least partially based on accepting an indication of at least one attribute of the individual. In an embodiment, invasive activator module 654 may activate a baroreceptor based on an indication of lightheadedness indicated by an individual. A further example of activating a baroreceptor may be found in Kieval, U.S. Pat. No. 7,502,650, which is incorporated herein by reference. In some instances, invasive activator module 654 may include a computer processor.

Operation 1708 illustrates activating at least one sensor at least one of a specified time or at a specified time interval. For example, as shown in FIGS. 4 through 8, time activator module 656 can activate at least one sensor at at least one of a specified time or at a specified time interval. In an embodiment, time activator module 656 may activate at least one sensor 15 minutes after an individual indicates a specified painful sensation. In other embodiments, time activator module 656 may activate at least one sensor at a specified time, at specified time intervals (e.g., every 30 seconds), a certain time of the day, and/or a certain time after an individual's attribute is accepted. In some instances, time activator module 656 may include a computer processor.

Figure 18:
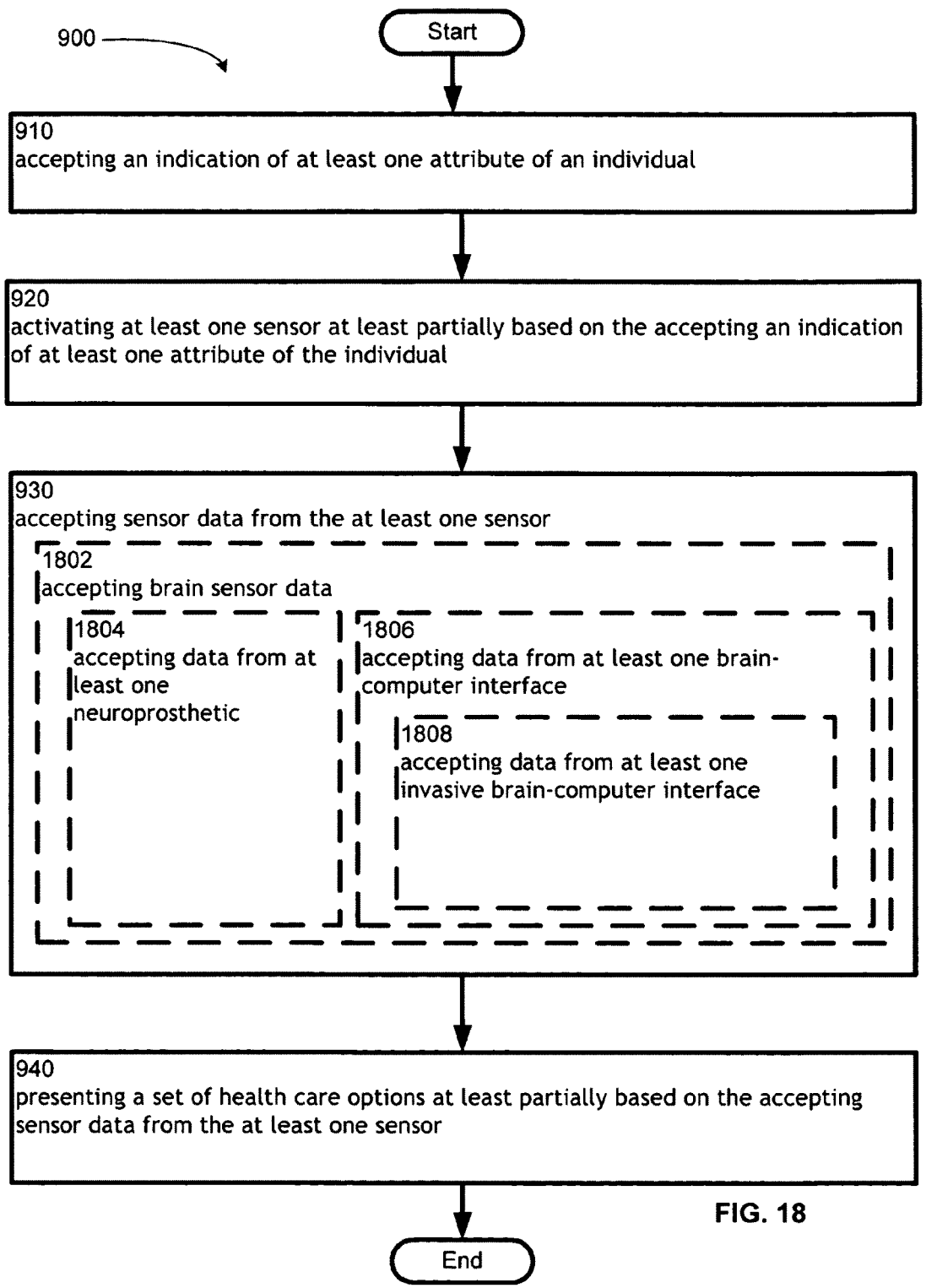
FIG. 18 illustrates an alternative embodiment of the operational flow of FIG. 9.

FIG. 18 illustrates alternative embodiments of the example operational flow 900 of FIG. 9. FIG. 18 illustrates example embodiments where operation 930 may include at least one additional operation. Additional operations may include operation 1802, operation 1804, operation 1806, and/or operation 1808.

Operation 1802 illustrates accepting brain sensor data. For example, as shown in FIGS. 4 through 8, brain sensor data accepter module 658 can accept brain sensor data. In an embodiment, brain sensor data accepter module 658 may accept from a brain sensor electrode array. One example of an electrode array may be found in Flaherty, U.S. Patent Publication No. 2007/0106143, which is incorporated herein by reference. In an embodiment, brain sensor data accepter module 658 may accept data detected by an electrode sensor that senses electrical signals generated by, for example, a patient while imagining movement. In this embodiment, the sensor may generate electrical signals that may be processed and/or accepted by, for example, brain sensor data accepter module 658. Some examples of a brain sensor may include non-invasive sensors, such as electroencephalogram (EEG) sensors, partially invasive sensors, such as electrocorticography sensors, and/or invasive sensors, such as implanted electrodes. A brain sensor data accepter module 658 of a brain sensor may include a patient having a medical condition, an individual experiencing one or more symptoms, an asymptomatic individual, or the like. Brain sensor data may include an indication of physiological impairment, for example for cosmetic enhancement, pregnancy, or improvement in athletic performance. In an embodiment, brain sensor data accepter module 658 may accept brain sensor data from an array of wireless sensors attached to the outside of a user's 140 head. In this embodiment, the array of wireless sensors may wirelessly detect electrical signals in the user's 140 brain and wirelessly relay the information to brain sensor data accepter module 658. The electrical signals produced by the brain may indicate a certain condition of the brain and/or body, such as physical damage, disability, and/or cognitive dysfunction, and may additionally indicate the success of and/or the degree of success of a previously prescribed therapy. In some instances, brain sensor data accepter module 658 may include a computer processor.

Further, operation 1804 illustrates accepting data from at least one neuroprosthetic. For example, as shown in FIGS. 4 through 8, neuroprosthetic accepter module 660 can accept data from at least one neuroprosthetic. A neuroprosthetic may include a device or a series of devices that may function as a substitute for a motor, sensory, and/or cognitive modality that may have been damaged and/or may otherwise not function properly. For example, a neuroprosthetic may include a cochlear implant. A cochlear implant may serve to substitute the functions performed by an ear drum. In an embodiment, neuroprosthetic accepter module 660 may accept data from a cochlear implant. In this embodiment, the data accepted from the cochlear implant may serve to indicate, for example, that the cochlear implant is malfunctioning and a surgery for replacement is needed. In some instances, neuroprosthetic accepter module 660 may include a computer processor.

Further, operation 1806 illustrates accepting data from at least one brain-computer interface. For example, as shown in FIGS. 4 through 8, interface accepter module 662 can accept data from at least one brain-computer interface. A brain-computer interface may include a direct communication pathway between a brain and an external device, such as a neuroprosthetic and/or an array of electrodes. In an embodiment, interface accepter module 662 may accept data from an electrocorticography device. Some brain-computer interface devices may be intrusive, partially intrusive, and/or non-intrusive. In some instances, interface accepter module 662 may include a computer processor.

Further, operation 1808 illustrates accepting data from at least one invasive brain-computer interface. For example, as shown in FIGS. 4 through 8, interface accepter module 662 can accept data from at least one invasive brain-computer interface. An invasive brain-computer interface device may include a device implanted directly into the grey matter of the brain during a neurosurgery. In an embodiment, interface accepter module 662 may accept data from an array of electrodes implanted into a user's 140 visual cortex designed to detect electrical signals and/or the absence of electrical signals and analyzing a user's 140 visual perception. This may serve to assist in diagnosis of, for example, a visual disability. Another example of an invasive brain-computer interface may be found in Boling, U.S. Pat. No. 7,283,856, which is incorporated herein by reference. In some instances, interface accepter module 662 may include a computer processor.

Figure 19:
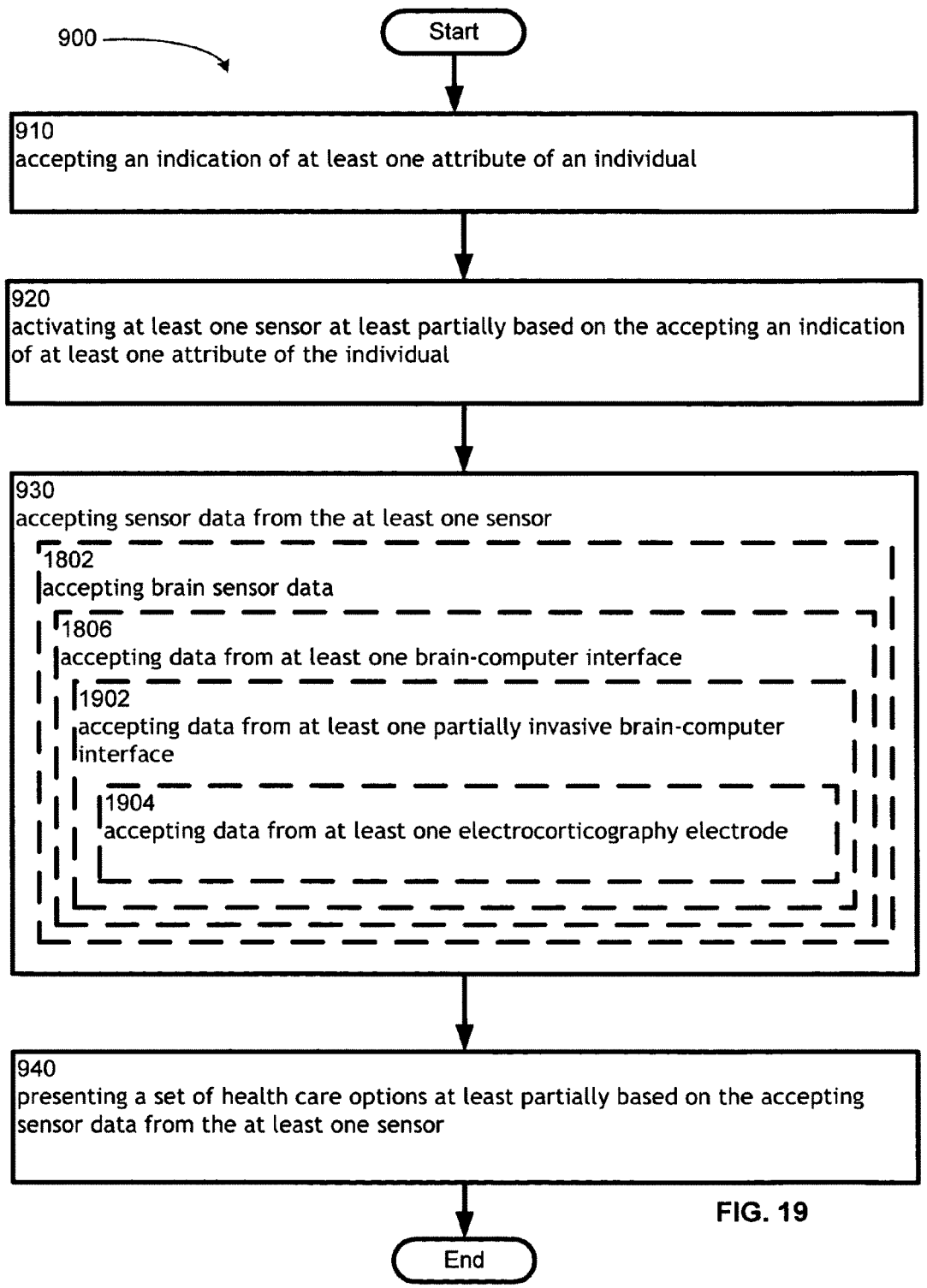
FIG. 19 illustrates an alternative embodiment of the operational flow of FIG. 9.

FIG. 19 illustrates alternative embodiments of the example operational flow 900 of FIG. 9. FIG. 19 illustrates example embodiments where operation 930 may include at least one additional operation. Additional operations may include operation 1902 and/or operation 1904.

Further, operation 1902 illustrates accepting data from at least one partially invasive brain-computer interface. For example, as shown in FIGS. 4 through 8, interface accepter module 662 can accept data from at least one partially invasive brain-computer interface. A partially invasive brain-computer interface may include a device implanted inside a person's skull but outside the brain. Some examples of a partially invasive brain-computer interface may include an electrocorticography device and/or a light reactive imaging device. In an embodiment, interface accepter module 662 may accept data from at least one partially invasive brain-computer interface, such as an electrode implanted between an individual's brain and skull. In some instances, interface accepter module 662 may include a computer processor.

Further, operation 1904 illustrates accepting data from at least one electrocorticography electrode. For example, as shown in FIGS. 4 through 8, electrocorticography accepter module 664 can accept data from at least one electrocorticography electrode. An electrocorticography device may include at least one electrode configured to measure electrical activity of the brain where, for example, the electrodes are embedded in a thin plastic pad that is placed above the cortex and beneath the dura matter. In an embodiment, electrocorticography accepter module 664 may accept data from at least one electrocorticography electrode configured to measure electrical signals in the brain of a patient that suffers from epilepsy. In this example, measuring the electrical signals may assist in determining the timing and/or intensity of an epileptic seizure and may help determine a suitable therapy for the patient. Another example of an electrocorticography device may be found in Leuthardt, U.S. Pat. No. 7,120,486, which is incorporated herein by reference. In some instances, electrocorticography accepter module 664 may include a computer processor and/or accepting circuitry, such as a modem.

Figure 20:
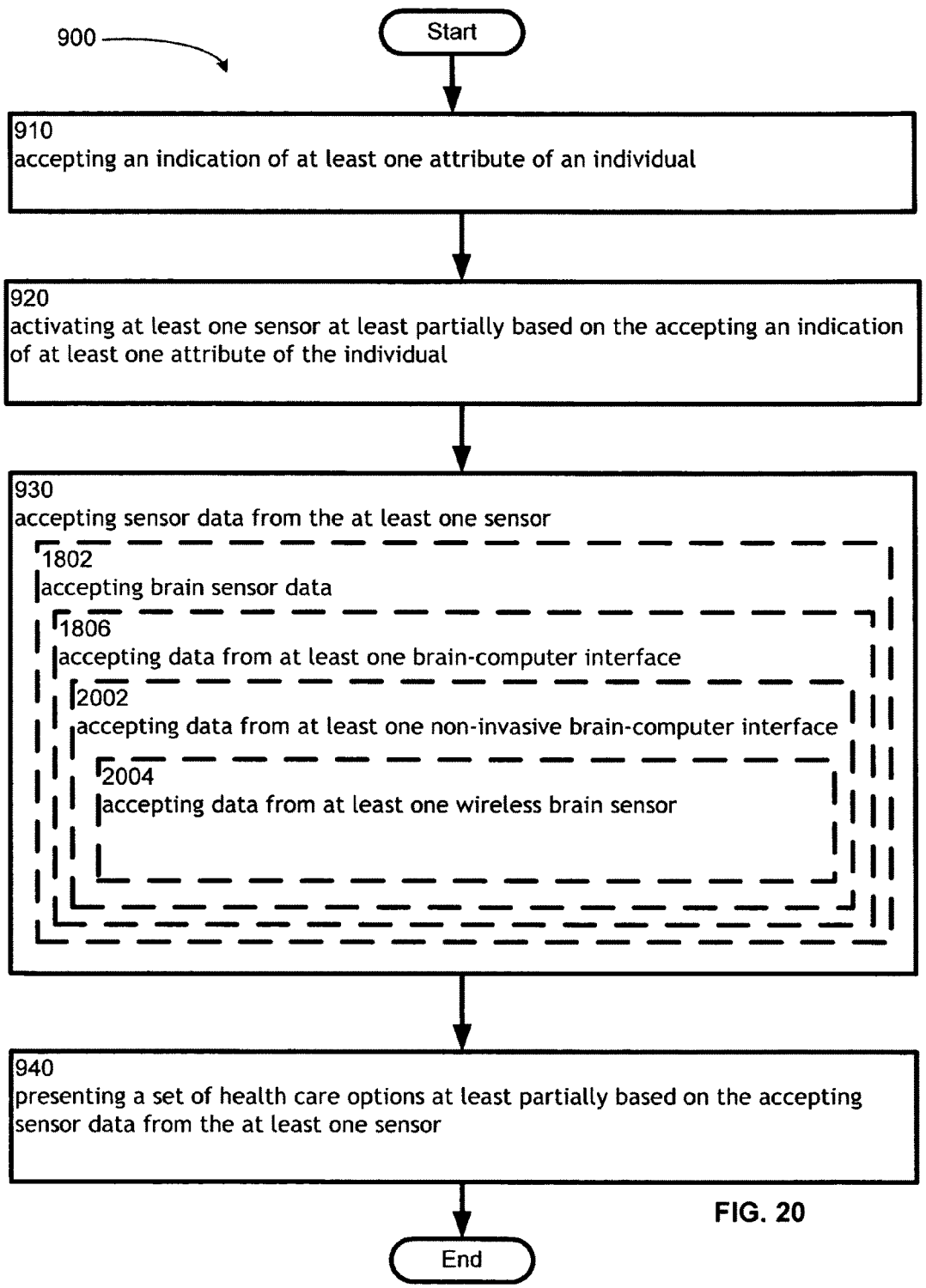
FIG. 20 illustrates an alternative embodiment of the operational flow of FIG. 9.

FIG. 20 illustrates alternative embodiments of the example operational flow 900 of FIG. 9. FIG. 20 illustrates example embodiments where operation 930 may include at least one additional operation. Additional operations may include operation 2002 and/or operation 2004.

Further, operation 2002 illustrates accepting data from at least one non-invasive brain-computer interface. For example, as shown in FIGS. 4 through 8, interface accepter module 662 can accept data from at least one non-invasive brain-computer interface. A non-invasive brain-computer interface may include a device that is able to measure signals from the brain without substantially interfering with and/or disturbing body tissue. In one embodiment, interface accepter module 662 may accept information from wireless brain sensors that are placed on an individual's head. Another example of a non-invasive brain-computer interface may include an electroencephalography sensor. In some instances, interface accepter module 662 may include a computer processor.

Further, operation 2004 illustrates accepting data from at least one wireless brain sensor. For example, as shown in FIGS. 4 through 8, wireless accepter module 668 can accept data from at least one wireless brain sensor. In an embodiment, wireless accepter module 668 may accept data from an array of brain sensors placed on the outside of an individual's head. In this embodiment, the array of brain sensors may detect electromagnetic waves created by neurons. The wireless brain sensor may be wirelessly connected to the wireless accepter module 668. Additional examples of a wireless brain sensor may include Fish, U.S. Pat. No. 6,155,974, and Najafi, et al., U.S. Patent Publication No. 2009/0105557, both of which are incorporated herein by reference. In some instances, wireless accepter module 668 may include a computer processor.

Figure 21:
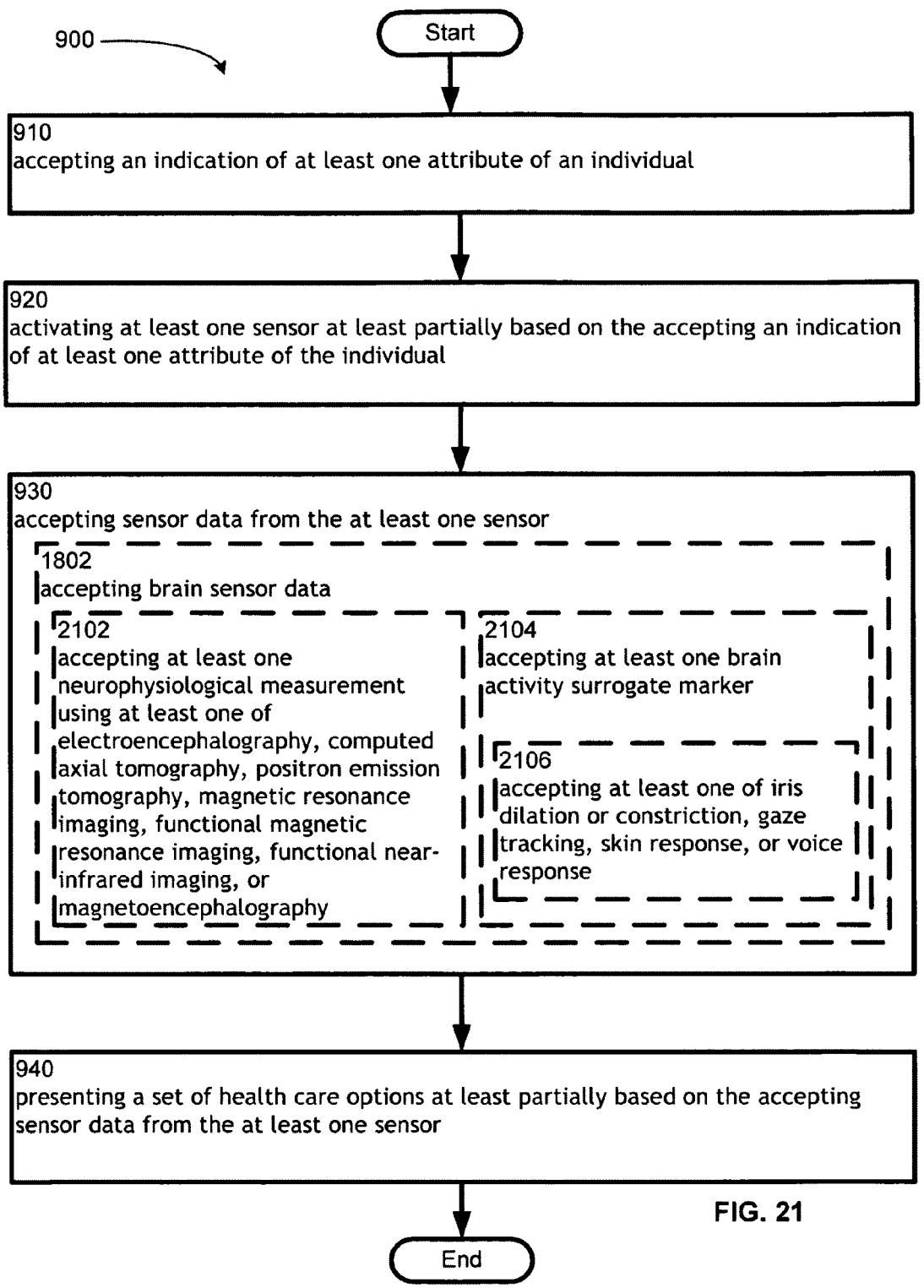
FIG. 21 illustrates an alternative embodiment of the operational flow of FIG. 9.

FIG. 21 illustrates alternative embodiments of the example operational flow 900 of FIG. 9. FIG. 21 illustrates example embodiments where operation 930 may include at least one additional operation. Additional operations may include operation 2102, operation 2104, and/or operation 2106.

Further, operation 2102 illustrates accepting at least one neurophysiological measurement using at least one of electroencephalography, computed axial tomography, positron emission tomography, magnetic resonance imaging, functional magnetic resonance imaging, functional near-infrared imaging, or magnetoencephalography. For example, as shown in FIGS. 4 through 8, neurophysiological measurement accepter module 670 can accept at least one neurophysiological measurement using at least one of electroencephalography, computed axial tomography, positron emission tomography, magnetic resonance imaging, functional magnetic resonance imaging, functional near-infrared imaging, or magnetoencephalography. In some instances, neurophysiological measurement accepter module 670 may include a computer processor, and/or a medical device, such as an apparatus configured to perform a computed axial tomography scan.

Electroencephalography may include measuring the electrical activity of the brain by recording from electrodes placed on the scalp or, in special cases, subdurally, or in the cerebral cortex, or from remote sensors. The resulting traces are known as an electroencephalogram (EEG) and represent a summation of post-synaptic potentials from a large number of neurons. EEG is most sensitive to a particular set of post-synaptic potentials: those which are generated in superficial layers of the cortex, on the crests of gyri directly abutting the skull and radial to the skull. Dendrites that are deeper in the cortex, inside sulci, are in midline or deep structures (such as the cingulate gyrus or hippocampus) or that produce currents that are tangential to the skull make a smaller contribution to the EEG signal.

One application of EEG is event-related potential (ERP) analysis. An ERP is any measured brain response that is directly the result of a thought or perception. ERPs can be reliably measured using electroencephalography (EEG), a procedure that measures electrical activity of the brain, typically through the skull and scalp. As the EEG reflects thousands of simultaneously ongoing brain processes, the brain response to a certain stimulus or event of interest is usually not visible in the EEG. One of the most robust features of the ERP response is a response to unpredictable stimuli. This response is known as the P300 (P3) and manifests as a positive deflection in voltage approximately 300 milliseconds after the stimulus is presented.

A two-channel wireless brain wave monitoring system powered by a thermo-electric generator has been developed by IMEC (Interuniversity Microelectronics Centre, Leuven, Belgium). This device uses the body heat dissipated naturally from the forehead as a means to generate its electrical power. The wearable EEG system operates autonomously with no need to change or recharge batteries. The EEG monitor prototype is wearable and integrated into a headband where it consumes 0.8 milliwatts. A digital signal processing block encodes extracted EEG data, which is sent to a PC via a 2.4-GHz wireless radio link. The thermoelectric generator is mounted on the forehead and converts the heat flow between the skin and air into electrical power. The generator is composed of 10 thermoelectric units interconnected in a flexible way. At room temperature, the generated power is about 2 to 2.5-mW or 0.03-mW per square centimeter, which is the theoretical limit of power generation from the human skin. Such a device is proposed to associate emotion with EEG signals. See Clarke, "IMEC has a brain wave: feed EEG emotion back into games," EE Times online, http://www.eetimes.eu/design/202801063 (Nov. 1, 2007).

Computed axial tomography may include medical imaging employing tomography and digital geometry processing for generating a three-dimensional image of the inside of an object from a large series of two-dimensional X-ray images taken around a single axis of rotation. Positron emission tomography may include a nuclear medicine imaging technique, which produces a three-dimensional image and/or map of at least one functional process in the body. The system detects pairs of gamma rays emitted indirectly by a positron-emitting radionuclide (a tracer), which is introduced into the body on a biologically active molecule. Images of tracer concentration in 3-dimensional space within the body may then be reconstructed by computer analysis. Magnetic resonance imaging may include a medical imaging technique using a magnetic field to align the nuclear magnetization of hydrogen atoms in water in the body, resulting in an image of the body. Functional magnetic resonance imaging may include and imaging method for measuring haemodynamic response related to neural activity in the brain or spinal cord. Functional near-infrared imaging (fNIR) may include a spectroscopic neuro-imaging method for measuring the level of neuronal activity in the brain. Functional near-infrared imaging (fNIR) is based on neurovascular coupling, or the relationship between metabolic activity and oxygen level (oxygenated hemoglobin) in feeding blood vessels.

Magnetoencephalography includes measuring the magnetic fields produced by electrical activity in the brain using magnetometers such as superconducting quantum interference devices (SQUIDs) or other devices. Smaller magnetometers are in development, including a mini-magnetometer that uses a single milliwatt infrared laser to excite rubidium in the context of an applied perpendicular magnetic field. The amount of laser light absorbed by the rubidium atoms varies predictably with the magnetic field, providing a reference scale for measuring the field. The stronger the magnetic field, the more light is absorbed. Such a system is currently sensitive to the 70 fT range, and is expected to increase in sensitivity to the 10 fT range. See Physorg.com, "New mini-sensor may have biomedical and security applications," Nov. 1, 2007, http://www.physorg.com/news113151078.html, which is incorporated herein by reference.

Further, operation 2104 illustrates accepting at least one brain activity surrogate marker. For example, as shown in FIGS. 4 through 8, marker accepter module 672 can accept at least one brain activity surrogate marker. In some instances, marker accepter module 672 may include a computer processor and/or medical instrumentality configured to measure a surrogate marker, such as a stethoscope, a face recognition system, and/or a sphygmomanometer. Brain activity surrogate markers may include indicators of attention, approval, disapproval, recognition, cognition, memory, trust, or the like in response to a stimulus, other than measurement of brain activity associated with the stimulus. Some examples of surrogate markers may include a skin response to a stimulus; a face pattern indicative of approval, disapproval, or emotional state; eye movements or pupil movements indicating visual attention to an object; voice stress patterns indicative of a mental state, or the like. Surrogate markers may be used in conjunction with brain activity measurements for higher confidence in a predictive or interpretational outcome. For example, brain activation of the caudate nucleus in combination with calm voice patterns may increase confidence in a predictor of trust between a subject and a stimulus. Additional discussion regarding surrogate markers may be found in Cohn, J. N., *Introduction to Surrogate Markers*, CIRCULATION 109: IV20-21, American Heart Association, (2004), which is incorporated herein by reference.

For example, emotion links to cognition, motivation, memory, consciousness, and learning and developmental systems. Affective communication depends on complex, rule-based systems with multiple channels and redundancy built into the exchange system, in order to compensate if one channel fails. Channels can include all five senses: for example, increased heart-rate or sweating may show tension or agitation and can be heard, seen, touched, smelt or tasted. Emotional exchanges may be visible displays of body tension or movement, gestures, posture, facial expressions or use of personal space; or audible displays such as tone of voice, choice of pitch contour, choice of words, speech rate, etc. Humans also use touch, smell, adornment, fashion, architecture, mass media, and consumer products to communicate our emotional state. Universals of emotion that cross cultural boundaries have been identified, and cultural differences have also been identified. For example 'love' is generally categorized as a positive emotion in Western societies, but in certain Eastern cultures there is also a concept for 'sad love.' Accordingly, universal emotional triggers may be used to transcend cultural barriers.

When communicating with computers, people often treat new media as if they were dealing with real people. They often follow complex social rules for interaction and modify their communication to suit their perceived conversation partner. Much research has focused on the use of facial actions and ways of coding them. Speech recognition systems have also attracted attention as they grow in capability and reliability, and can recognize both verbal messages conveyed by spoken words, and non verbal messages, such as those conveyed by pitch contours.

System responses and means of expressing emotions also vary. Innovative prototypes are emerging designed to respond indirectly, so the user is relatively unaware of the response: for example by adaptation of material, such as changing pace or simplifying or expanding content. Other systems use text, voice technology, visual agents, or avatars to communicate. See Axelrod et al., "Smoke and Mirrors: Gathering User Requirements for Emerging Affective Systems," 26th Int. Conf. Information Technology Interfaces/TI 2004, Jun. 7-10, 2004, Cavtat, Croatia, pp. 323-328, which is incorporated herein by reference.

Further, operation 2106 illustrates accepting at least one of iris dilation or constriction, gaze tracking, skin response, or voice response. For example, as shown in FIGS. 4 through 8, response accepter module 674 can accept at least one of iris dilation or constriction, gaze tracking, skin response, or voice response. In some instances, response accepter module 674 may include a computer processor and/or medical instrumentality, such as a stethoscope and/or a sphygmomanometer. In one embodiment, response accepter module 674 may record changes in the movement of an individual's iris (with corresponding changes in the size of the pupil) before, during, and/or after administration of a bioactive agent and/or an artificial sensory experience. Such measurements of physiologic activity that indicate brain activity and/or mental state may be carried out at a time that is proximate to administration of a bioactive agent and/or an artificial sensory experience.

In one embodiment, response accepter module 674 may measure and/or record gaze tracking. In some instances, response accepter module 674 may include a camera that can monitor a subject's eye movements in order to determine whether the subject looks at a presented characteristic, for example, during a certain time period. For example, a camera may include a smart camera that can capture images, process them and issue control commands within a millisecond time frame. Such smart cameras are commercially available (e.g., Hamamatsu's Intelligent Vision System; http://jp.hamamatsu.com/en/product_info/index.html). Such image capture systems may include dedicated processing elements for each pixel image sensor. Other camera systems may include, for example, a pair of infrared charge coupled device cameras to continuously monitor pupil size and position as a user watches a visual target moving forward and backward. This can provide real-time data relating to pupil accommodation relative to objects on, for example, a user interface, such as a display. (e.g., http://jp.hamamatsu-.com/en/rd/publication/scientific_american/common/pdf/scientific_0608.pdf).

Eye movement and/or iris movement may also be measured by video-based eye trackers. In these systems, a camera focuses on one or both eyes and records eye movement as the viewer looks at a stimulus. Contrast may be used to locate the center of the pupil, and infrared and near-infrared non-collumnated light may be used to create a corneal reflection. The vector between these two features can be used to compute gaze intersection with a surface after a calibration for an individual.

In one embodiment, response accepter module 674 may measure and/or record skin response. Brain activity may be determined by detection of a skin response associated with a stimulus. One skin response that may correlate with mental state and/or brain activity is galvanic skin response (GSR), also known as electrodermal response (EDR), psychogalvanic reflex (PGR), or skin conductance response (SCR). This is a change in the electrical resistance of the skin. There is a relationship between sympathetic nerve activity and emotional arousal, although one may not be able to identify the specific emotion being elicited. The GSR is highly sensitive to emotions in some people. Fear, anger, startle response, orienting response, and sexual feelings are all among the emotions which may produce similar GSR responses. GSR is typically measured using electrodes to measure skin electrical signals.

For example, an Ultimate Game study measured skin-conductance responses as a surrogate marker or autonomic index for affective state, and found higher skin conductance activity for unfair offers, and as with insular activation in the brain, this measure discriminated between acceptances and rejections of these offers. See Sanfey, "Social Decision-Making: Insights from Game Theory and Neuroscience," Science, vol. 318, pp. 598-601 (26 Oct. 2007), which is incorporated herein by reference. Other skin responses may include flushing, blushing, goose bumps, sweating, or the like.

In one embodiment, response accepter module 674 may measure and/or record voice response. Voice response may include speech captured by a microphone during presentation of a characteristic. Speech or voice can be measured, for example, by examining voice, song, and/or other vocal utterances of a subject before, during, and/or after administration of a bioactive agent and/or an artificial sensory experience to an individual. Such measurements may include, for example, as discussed above, layered voice analysis, voice stress analysis, or the like.

The reaction of an individual to an administered bioactive agent and/or an artificial sensory experience, such as an event in a virtual world may be a recognizable vocal exclamation such as "Wow, that's nice!" that may be detectable by a response accepter module 674, such as a microphone monitoring the subject while being administered an artificial sensory experience. A response accepter module 674 may include a voice response module and/or a speech recognition function, such as a software program or computational device that can identify and/or record an utterance of a subject as speech or voice data.

Figure 22:
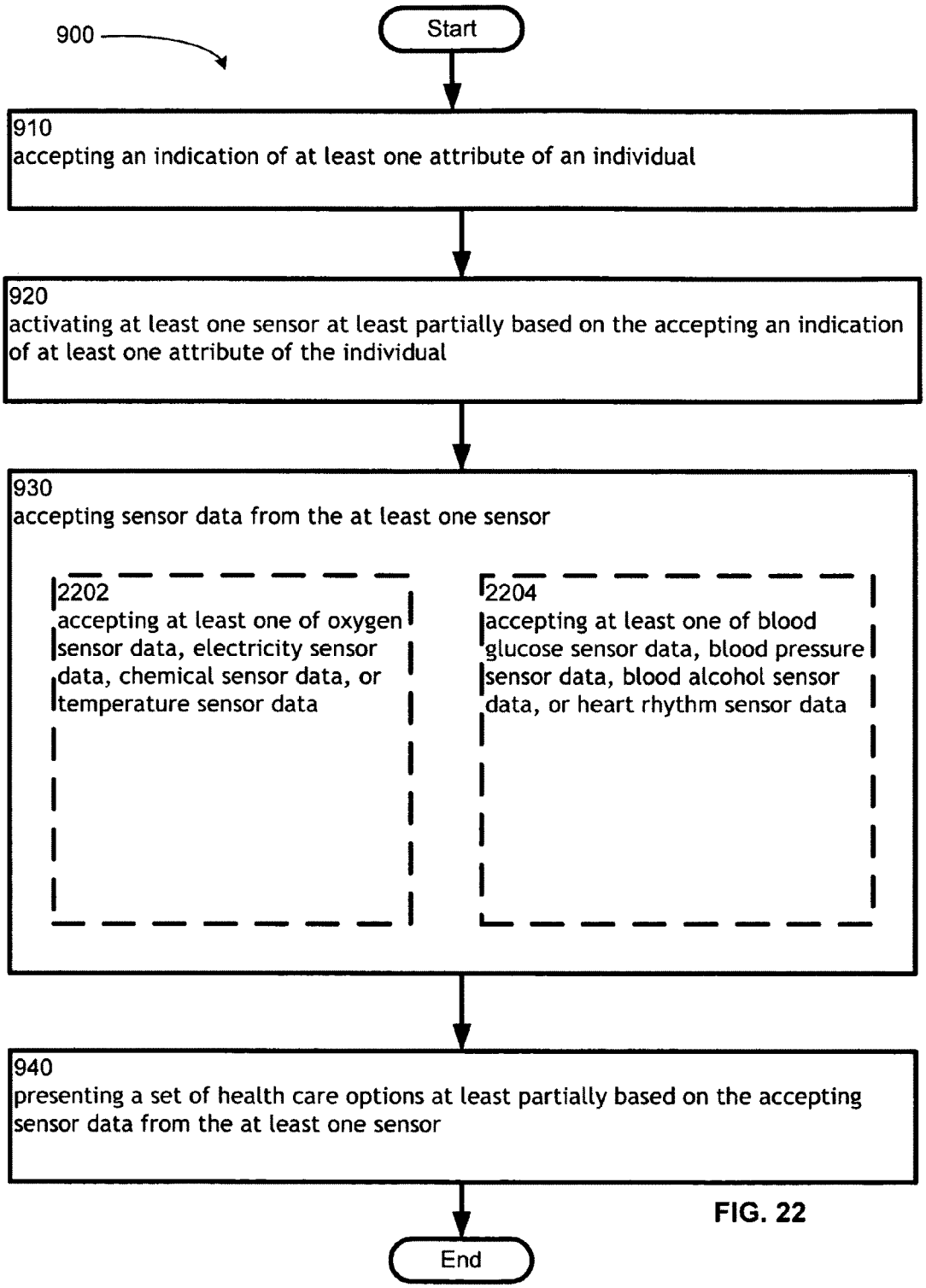
FIG. 22 illustrates an alternative embodiment of the operational flow of FIG. 9.

FIG. 22 illustrates alternative embodiments of the example operational flow 900 of FIG. 9. FIG. 22 illustrates example embodiments where operation 930 may include at least one additional operation. Additional operations may include operation 2202, and/or operation 2204.

Operation 2202 illustrates accepting at least one of oxygen sensor data, electricity sensor data, chemical sensor data, or temperature sensor data. For example, as shown in FIGS. 4 through 8, sensor data accepter module 676 can accept at least one of oxygen sensor data, electricity sensor data, chemical sensor data, or temperature sensor data. In an embodiment, sensor data accepter module 676 may accept temperature sensor data from an infrared thermometer. One example of an oxygen sensor may include a pulse oximeter. Another example of an oxygen sensor may be found in Milstein et al., U.S. Pat. No. 5,106,482. Some examples of an electricity sensor may include an electroencephalography sensor and/or a piezoelectric ultrasound transducer. An additional example of an electricity sensor may include the bio-electric sensor found in Shahinpoor et al., U.S. Pat. No. 6,829,499, which is incorporated herein by reference. A chemical sensor may include, for example, a pH meter and/or a blood glucose sensor. An additional chemical sensor system may be found in Darrow et al., U.S. Pat. No. 6,480,730, which is incorporated herein by reference. Some examples of a temperature sensor may include a thermocouple and/or a thermometer. An additional example of a temperature system may be found in Takaki, U.S. Pat. No. 6,019,507, which is incorporated herein by reference. In some instances, sensor data accepter module 676 may include a computer processor and/or connecting circuitry, such as wired connections or a keyboard.

Operation 2204 illustrates accepting at least one of blood glucose sensor data, blood pressure sensor data, blood alcohol sensor data, or heart rhythm sensor data. For example, as shown in FIGS. 4 through 8, blood sensor data accepter module 678 can accept at least one of blood glucose sensor data, blood pressure sensor data, blood alcohol sensor data, or heart rhythm sensor data. In an embodiment, blood sensor data accepter module 678 may accept blood glucose sensor data. One example of a blood glucose meter may include the ACCU-CHEK Aviva Blood Glucose Meter available from Roche, Basel, Switzerland. An example of a blood pressure sensor may include a blood pressure cuff and/or a sphygmomanometer. An example of a blood alcohol sensor may include a breathalyzer such as the BACtrack S50 Breathalyzer, available from KHN Solutions LLC, San Francisco, Calif. An example of a heart rhythm sensor may include an EKG based heart rate monitor, such as the monitor found in Lo et al., U.S. Pat. No. 5,738,104, or the heart sound sensor found in Anderson et al., U.S. Patent Publication No. 2009/0030334, both of which are incorporated herein by reference. In some instances, blood sensor data accepter module 678 may include a computer processor.

Figure 23:
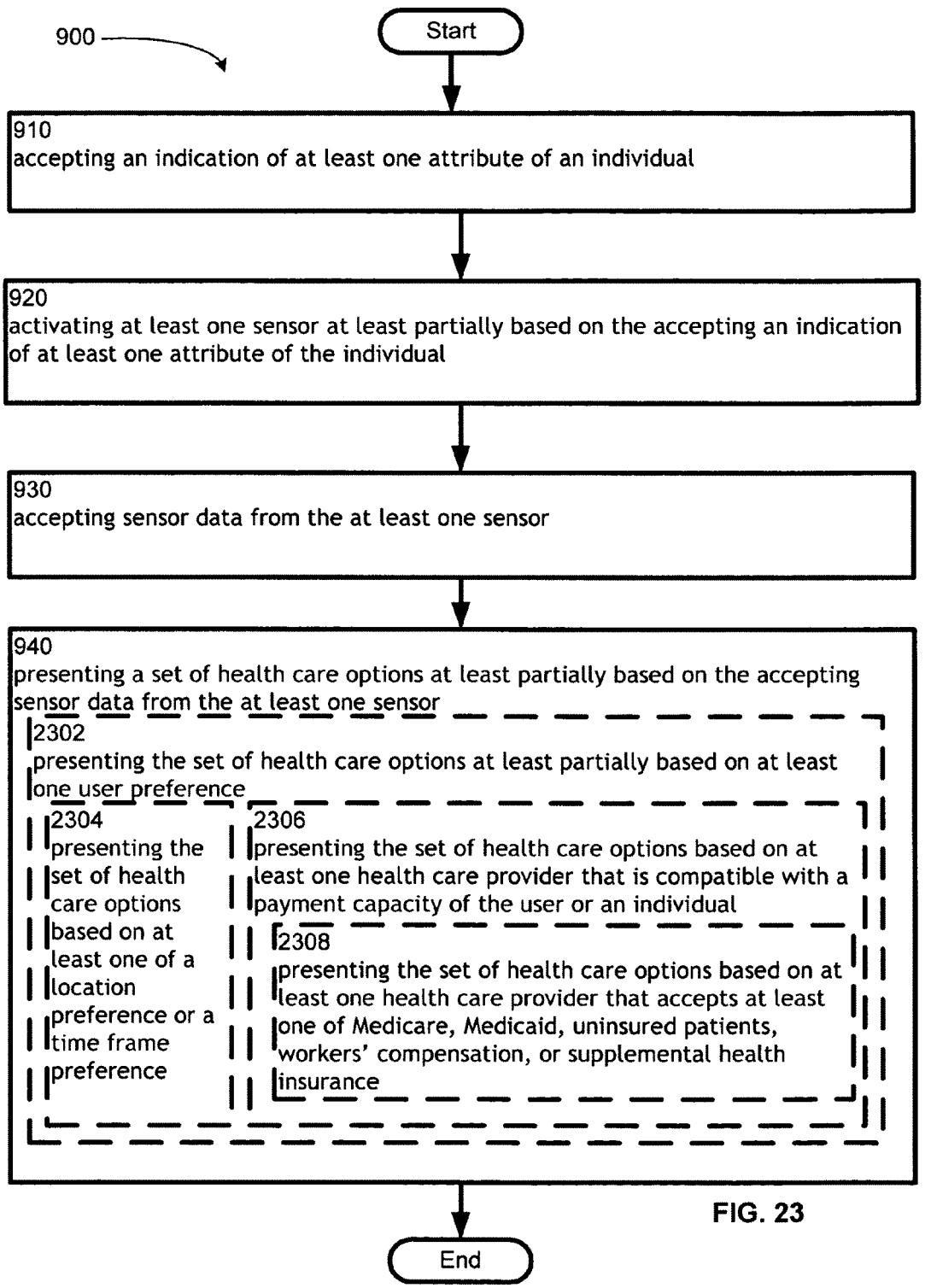
FIG. 23 illustrates an alternative embodiment of the operational flow of FIG. 9.

FIG. 23 illustrates alternative embodiments of the example operational flow 900 of FIG. 9. FIG. 23 illustrates example embodiments where operation 940 may include at least one additional operation. Additional operations may include operation 2302, operation 2304, operation 2306, and/or operation 2308.

Operation 2302 illustrates presenting the set of health care options at least partially based on at least one user preference. For example, as shown in FIGS. 4 through 8, preference presenter module 680 can present the set of health care options at least partially based on at least one user preference. In one embodiment, preference presenter module 680 may present, for example, a course of testing and/or treatment that takes into account one or more preferences or sensitivities of the individual, such as "treatments other than surgery," "local treatment options," "non-narcotic treatment options," or the like. In some instances, preference presenter module 680 may include a computer processor.

Further, operation 2304 illustrates presenting the set of health care options based on at least one of a location preference or a time frame preference. For example, as shown in FIGS. 4 through 8, time preference presenter module 682 can present the set of health care options based on at least one of a location preference or a time frame preference. In one embodiment, time preference presenter module 682 may present at least one health service option based on brain sensor data indicating a likelihood of epileptic seizure and a location such as "Miami-Dade County, Florida." A database of relevant service providers may contain, inter alia, location information allowing time preference presenter module 682 to present or determine, in this example, only relevant surgeons located in Miami-Dade County, Florida. Additionally, time preference presenter module 682 may filter out database results that include surgeons with, for example, less than five years of experience in practice and/or located outside of a specified geographic area, in some cases resulting in zero options being listed for a given therapy. In a case where no options are returned, other treatment options may be selected and a new search carried out. In some instances, time preference presenter module 682 may include a computer processor.

Further, operation 2306 illustrates presenting the set of health care options based on at least one health care provider that is compatible with a payment capacity of the user or an individual. For example, as shown in FIGS. 4 through 8, payment capacity presenter module 684 can present the set of health care options based on at least one health care provider that is compatible with a payment capacity of the user or an individual. In one embodiment, payment capacity presenter module 684 may present treatment options based on the key phrase "Alzheimer's" (determined by utilizing brain sensor data) and "Medicaid" as the payment capacity of the individual. In this example, treatment options available for payment with Medicaid may be determined and presented to the user. These treatment options will be limited to those approved by the United States Food and Drug Administration, while others, such as Aricept®, may be omitted as incompatible with Medicaid coverage. Conversely, if the payment capacity for the individual is high, off-label treatments and those with experimental status may be included as treatment options. Examples of other payment capacities include specific private insurance plans such as Premera, Blue Cross/Blue Shield, or the like. Other examples include Medicare, fee-for-service, point-of-service, preferred provider organizations, or health maintenance organizations. In some instances, payment capacity presenter module 684 may include a computer processor.

Further, operation 2308 illustrates presenting the set of health care options based on at least one health care provider that accepts at least one of Medicare, Medicaid, uninsured patients, workers' compensation, or supplemental health insurance. For example, as shown in FIGS. 4 through 8, insurance presenter module 686 can present the set of health care options based on at least one health care provider that accepts at least one of Medicare, Medicaid, uninsured patients, workers' compensation, or supplemental health insurance. In one embodiment, insurance presenter module 686 may present at least one health service option based on an accepted key phrase such as "Cerebral palsy" and "no insurance" as indications of at least one health-related status of an individual. In this example, insurance presenter module 686 may determine care options that are available to an uninsured individual, such as services provided by Denver Health, Denver's public health system, or the Seton System in Central Texas. In some instances, insurance presenter module 686 may include a computer processor.

Figure 24:
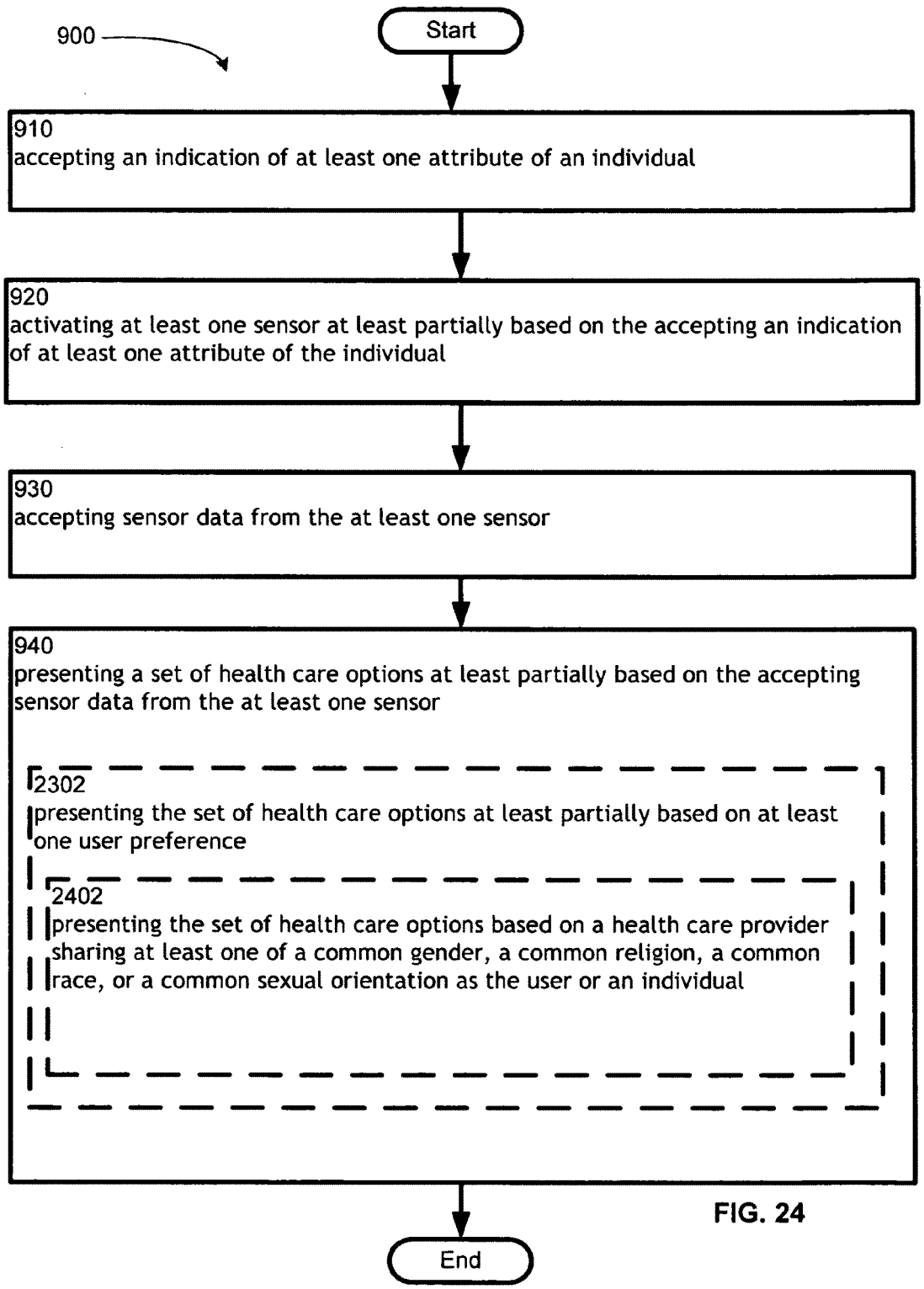
FIG. 24 illustrates an alternative embodiment of the operational flow of FIG. 9.

FIG. 24 illustrates alternative embodiments of the example operational flow 900 of FIG. 9. FIG. 24 illustrates example embodiments where operation 940 may include at least one additional operation. Additional operations may include operation 2402.

Further, operation 2402 illustrates presenting the set of health care options based on a health care provider sharing at least one of a common gender, a common religion, a common race, or a common sexual orientation as the user or an individual. For example, as shown in FIGS. 4 through 8, commonality presenter module 688 can present the set of health care options based on a health care provider sharing at least one of a common gender, a common religion, a common race, or a common sexual orientation as the user or an individual. In an embodiment, commonality presenter module 688 can present a set of physicians based on a user's preference for a Jewish doctor based at least in part on the user's religious beliefs as a Jew. In some instances, commonality presenter module 688 may include a computer processor.

Figure 25:
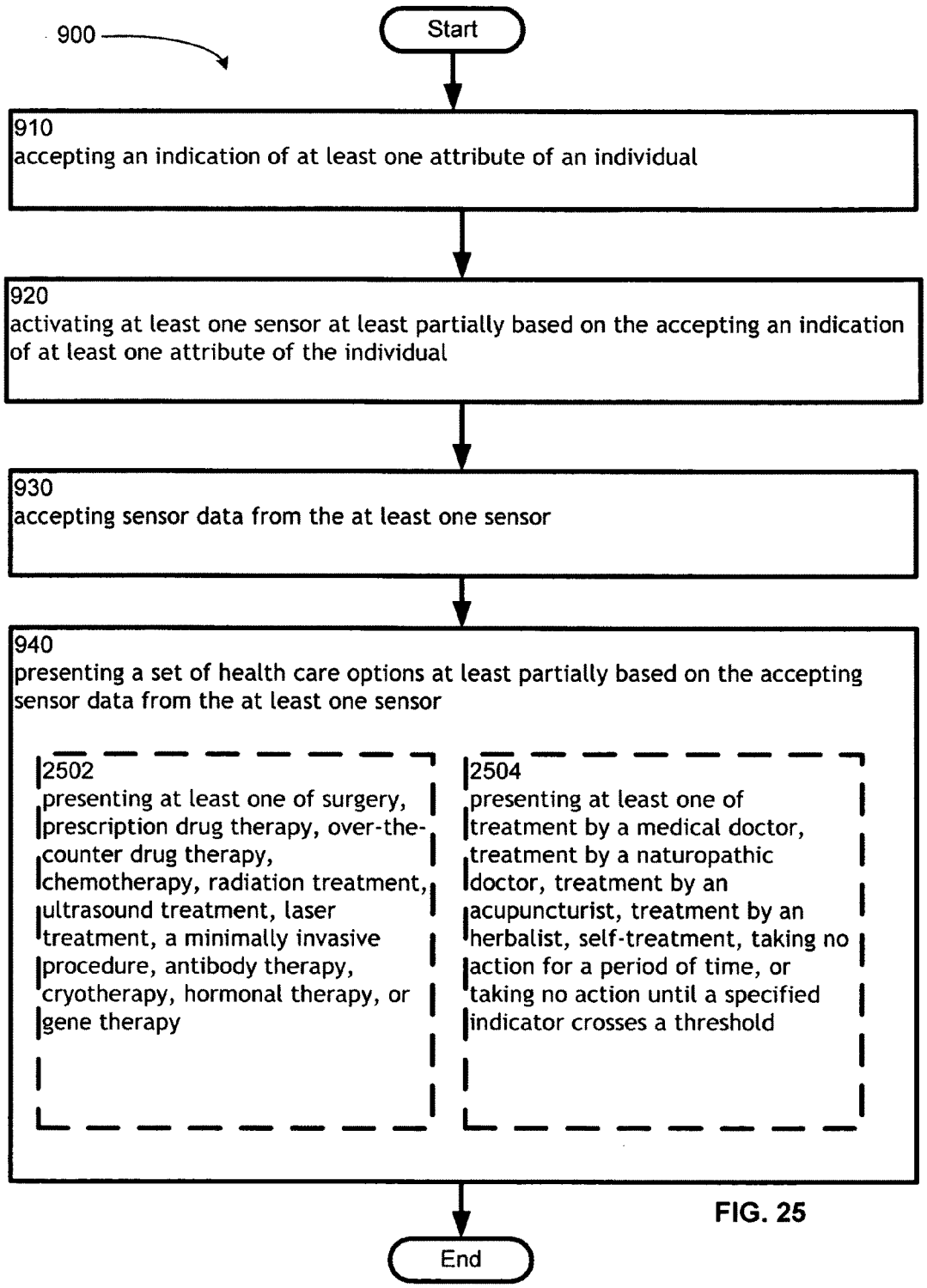
FIG. 25 illustrates an alternative embodiment of the operational flow of FIG. 9.

FIG. 25 illustrates alternative embodiments of the example operational flow 900 of FIG. 9. FIG. 25 illustrates example embodiments where operation 940 may include at least one additional operation. Additional operations may include operation 2502 and/or operation 2504.

Operation 2502 illustrates presenting at least one of surgery, prescription drug therapy, over-the-counter drug therapy, chemotherapy, radiation treatment, ultrasound treatment, laser treatment, a minimally invasive procedure, antibody therapy, cryotherapy, hormonal therapy, or gene therapy. For example, as shown in FIGS. 4 through 8, procedure presenter module 690 can present at least one of surgery, prescription drug therapy, over-the-counter drug therapy, chemotherapy, radiation treatment, ultrasound treatment, laser treatment, a minimally invasive procedure, antibody therapy, cryotherapy, hormonal therapy, or gene therapy. In one embodiment, procedure presenter module 690 may present health services options including, for example, options including prescription drug therapy and surgery based on data received from an array of non-invasive brain sensors that indicate motor neurone disease in an individual. In some instances, procedure presenter module 690 may include a computer processor.

Operation 2504 illustrates presenting at least one of treatment by a medical doctor, treatment by a naturopathic doctor, treatment by an acupuncturist, treatment by an herbalist, self-treatment, taking no action for a period of time, or taking no action until a specified indicator crosses a threshold. For example, as shown in FIGS. 4 through 8, treatment presenter module 692 can present at least one of treatment by a medical doctor, treatment by a naturopathic doctor, treatment by an acupuncturist, treatment by an herbalist, self-treatment, taking no action for a period of time, or taking no action until a specified indicator crosses a threshold. In one embodiment, treatment presenter module 692 may accept "narcolepsy" as an indication of health-related status and determine various health service options, such as treatment by an acupuncturist. In this embodiment, treatment presenter module 692 may present a list of acupuncturists with experience in treating narcolepsy. Virtually any combination of available testing/treatment options may be presented. Additionally, testing/treatment options may be narrowed by user preference. In some instances, treatment presenter module 692 may include a computer processor.

Figure 26:
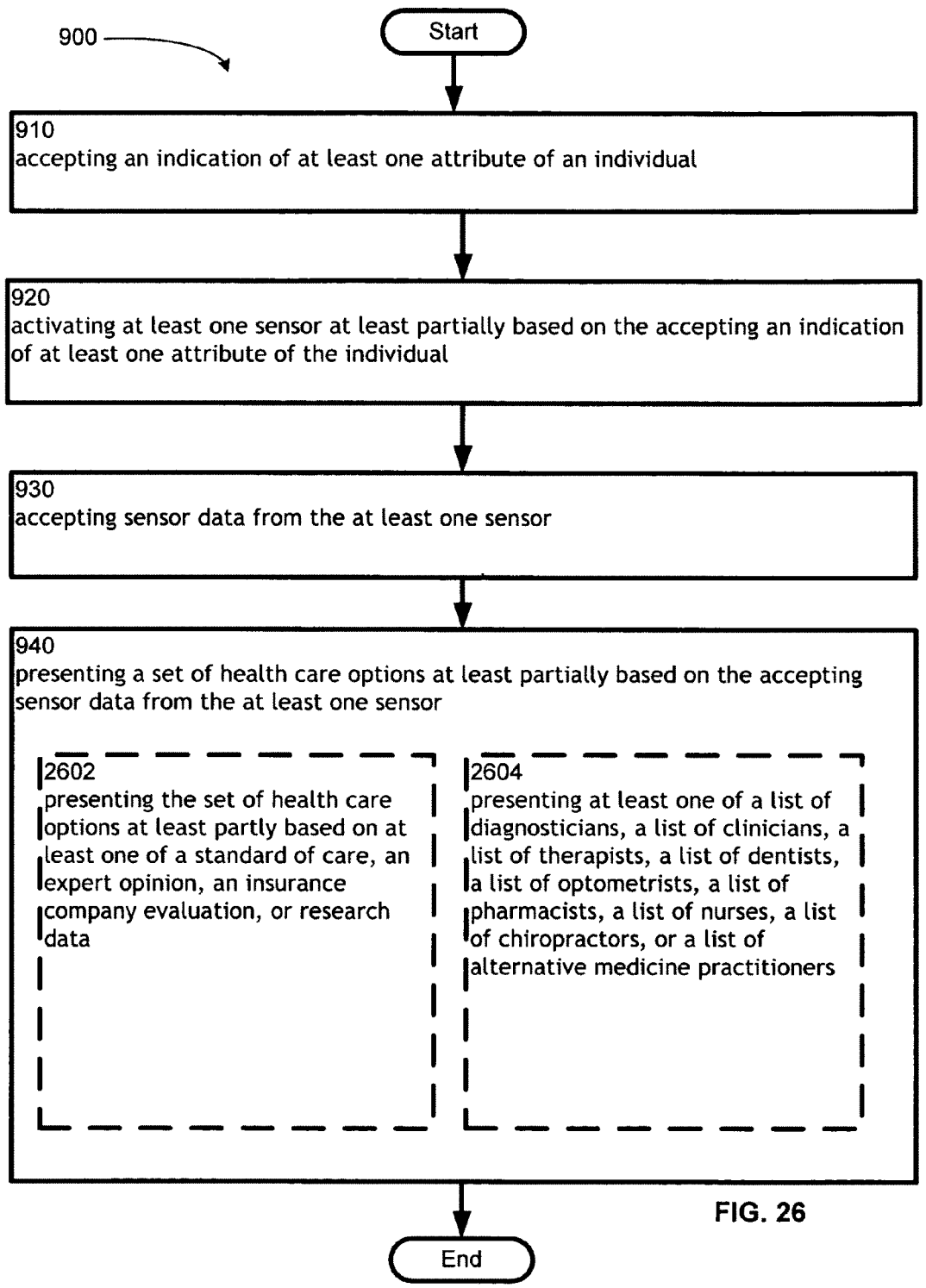
FIG. 26 illustrates an alternative embodiment of the operational flow of FIG. 9.

FIG. 26 illustrates alternative embodiments of the example operational flow 900 of FIG. 9. FIG. 26 illustrates example embodiments where operation 940 may include at least one additional operation. Additional operations may include operation 2602 and/or operation 2604.

Operation 2602 illustrates presenting the set of health care options at least partly based on at least one of a standard of care, an expert opinion, an insurance company evaluation, or research data. For example, as shown in FIGS. 4 through 8, option presenter module 694 can present the set of health care options at least partly based on at least one of a standard of care, an expert opinion, an insurance company evaluation, or research data. In one embodiment, option presenter module 694 may present a set of health service options based on a standard of care database. The standard of care database may include information, such as treatment options that are currently recommended by the medical community and/or approved by one or more insurance companies. In some instances, option presenter module 694 may include a computer processor.

Operation 2604 illustrates presenting at least one of a list of diagnosticians, a list of clinicians, a list of therapists, a list of dentists, a list of optometrists, a list of pharmacists, a list of nurses, a list of chiropractors, or a list of alternative medicine practitioners. For example, as shown in FIGS. 4 through 8, provider presenter module 696 can present at least one of a list of diagnosticians, a list of clinicians, a list of therapists, a list of dentists, a list of optometrists, a list of pharmacists, a list of nurses, a list of chiropractors, or a list of alternative medicine practitioners. In one embodiment, provider presenter module 696 can, based on accepted brain sensor data, access a service provider database to determine a list of clinicians (e.g., surgeons). In this embodiment, provider presenter module 696 can present a list of clinicians experienced in treating neurological disorders indicated by the accepted brain sensor data. In another example, provider presenter module 696 can access a service provider database to provide a list of physicians who are pain specialists and a list of acupuncturists in response to receiving "head pain" as an indication of health-related status. In some instances, provider presenter module 696 may include a computer processor.

Figure 27:
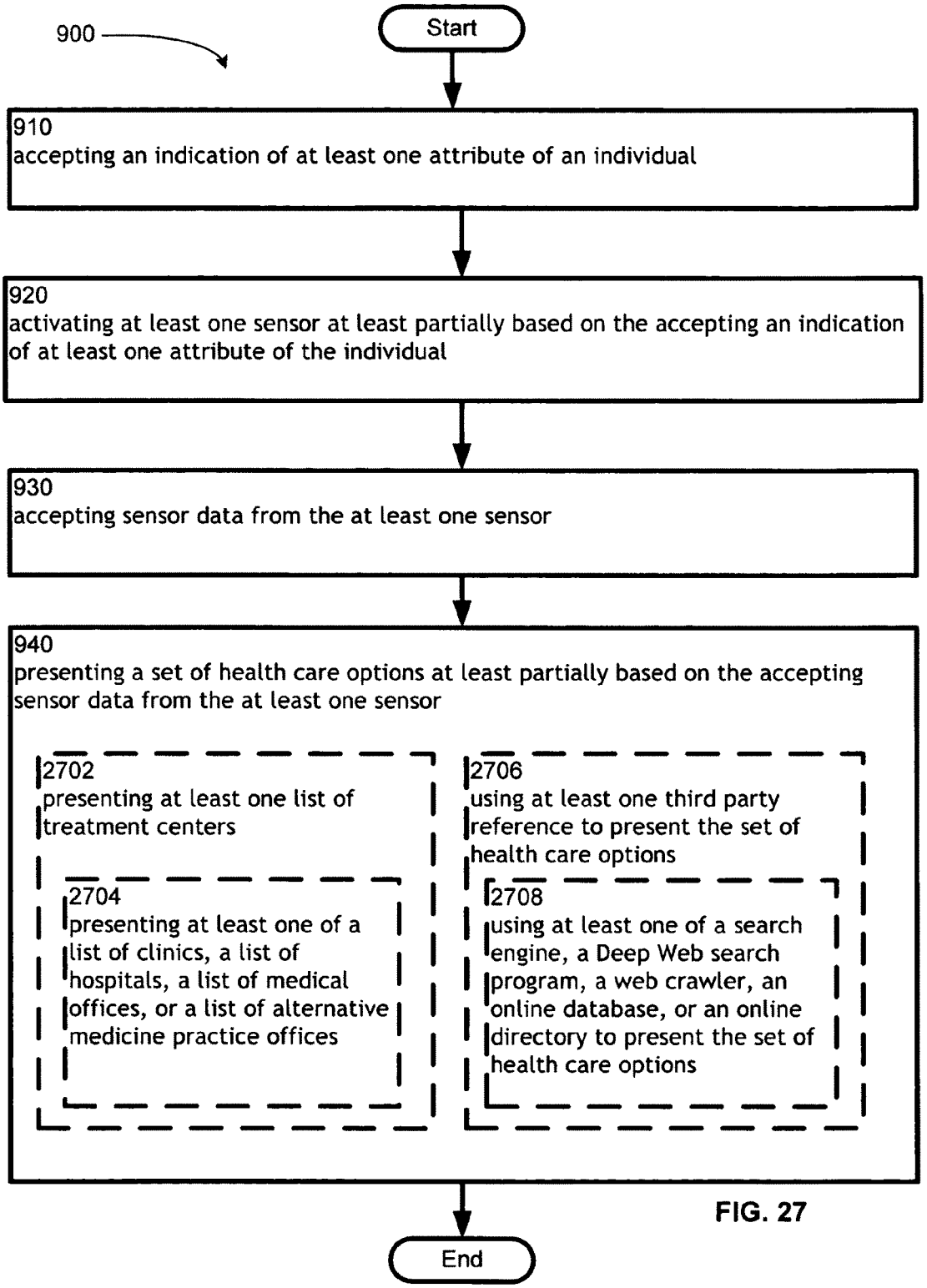
FIG. 27 illustrates an alternative embodiment of the operational flow of FIG. 9.

FIG. 27 illustrates alternative embodiments of the example operational flow 900 of FIG. 9. FIG. 27 illustrates example embodiments where operation 940 may include at least one additional operation. Additional operations may include operation 2702, operation 2704, operation 2706, and/or operation 2708.

Operation 2702 illustrates presenting at least one list of treatment centers. For example, as shown in FIGS. 4 through 8, center presenter module 698 can present at least one list of treatment centers. In one embodiment, center presenter module 698 may present a list of hospitals that perform a given medical procedure to a user at least partially based on data accepted from an array of brain sensors. In some instances, center presenter module 698 may include a computer processor.

Further, operation 2704 illustrates presenting at least one of a list of clinics, a list of hospitals, a list of medical offices, or a list of alternative medicine practice offices. For example, as shown in FIGS. 4 through 8, office presenter module 700 can present at least one of a list of clinics, a list of hospitals, a list of medical offices, or a list of alternative medicine practice offices. In one embodiment, office presenter module 700 may present a list of dementia treatment clinics for an individual in need of dementia-related health service options. In another example, office presenter module 700 may determine a list of epilepsy clinics. In some instances, office presenter module 700 may include a computer processor.

Operation 2706 illustrates using at least one third party reference to present the set of health care options. For example, as shown in FIGS. 4 through 8, user module 702 can use at least one third party reference to present the set of health care options. In one embodiment, user module 702 may use a Physicians' Desk Reference (PDR) database to determine and then present, for example, a set of health-related services options for an individual with traumatic brain injury. In this example, user module 702 may use a PDR neurology database to retrieve health-related services options for a patient with traumatic brain injury. In some instances, user module 702 may include a computer processor.

Further, operation 2708 illustrates using at least one of a search engine, a Deep Web search program, a web crawler, an online database, or an online directory to present the set of health care options. For example, as shown in FIGS. 4 through 8, program user module 704 can use at least one of a search engine, a Deep Web search program, a web crawler, an online database, or an online directory to present the set of health care options. In one embodiment, program user module 704 may use a web crawler to identify a suitable online database, and then a subsequent search function to extract specific data from the online database. For example, if program user module 704 accepts "Tourette syndrome" as an indication of at least one health-related status of an individual, it may initiate a search of the web for medical research databases containing Tourette syndrome treatment information. A possible result of this search is the medical research database "PubMed." Program user module 704 next may search the PubMed database for "Tourette syndrome" in order to determine specific treatment information as the at least one health service option. In some instances, program user module 704 may include a computer processor.

Figure 28:
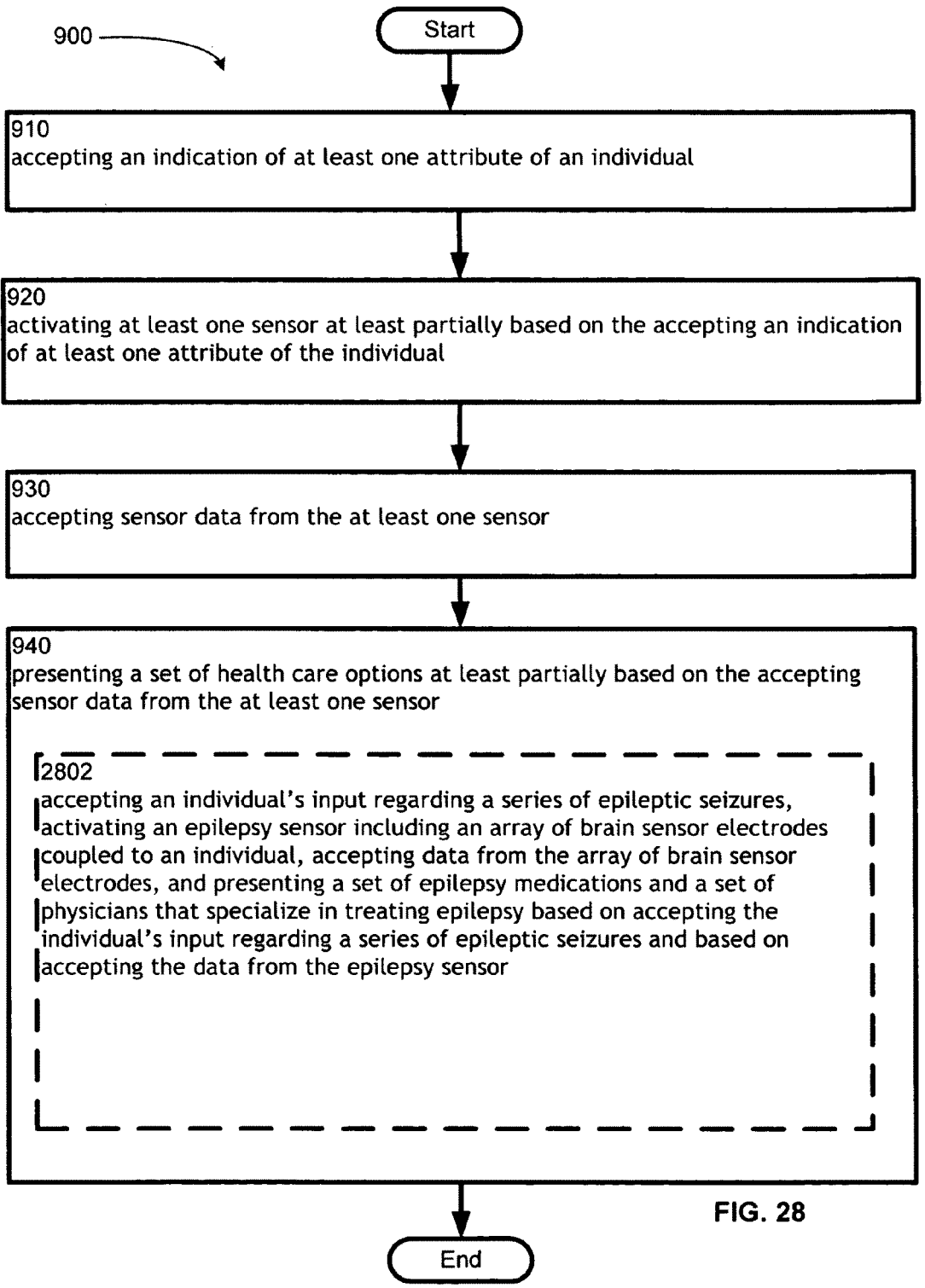
FIG. 28 illustrates an alternative embodiment of the operational flow of FIG. 9.

FIG. 28 illustrates alternative embodiments of the example operational flow 900 of FIG. 9. FIG. 28 illustrates example embodiments where operation 940 may include at least one additional operation. Additional operations may include operation 2802.

Operation 2802 illustrates accepting an individual's input regarding a series of epileptic seizures, activating an epilepsy sensor including an array of brain sensor electrodes coupled to an individual, accepting data from the array of brain sensor electrodes, and presenting a set of epilepsy medications and a set of physicians that specialize in treating epilepsy based on accepting the individual's input regarding a series of epileptic seizures and based on accepting the data from the epilepsy sensor. For example, as shown in FIGS. 4 through 8, accepter module 602, activator module 604, data accepter module 606, and presenter module 608 can accept an individual's input regarding a series of epileptic seizures, activate an epilepsy sensor including an array of brain sensor electrodes coupled to an individual, accept data from the array of brain sensor electrodes, and present a set of epilepsy medications and a set of physicians that specialize in treating epilepsy based on accepting the individual's input regarding a series of epileptic seizures and based on accepting the data from the epilepsy sensor. In some instances accepter module 602 may include a computer processor. In some instances activator module 604 may include a computer processor. In some instances data accepter module 606 may include a computer processor. In some instances presenter module 608 may include a computer processor.

Figure 29:
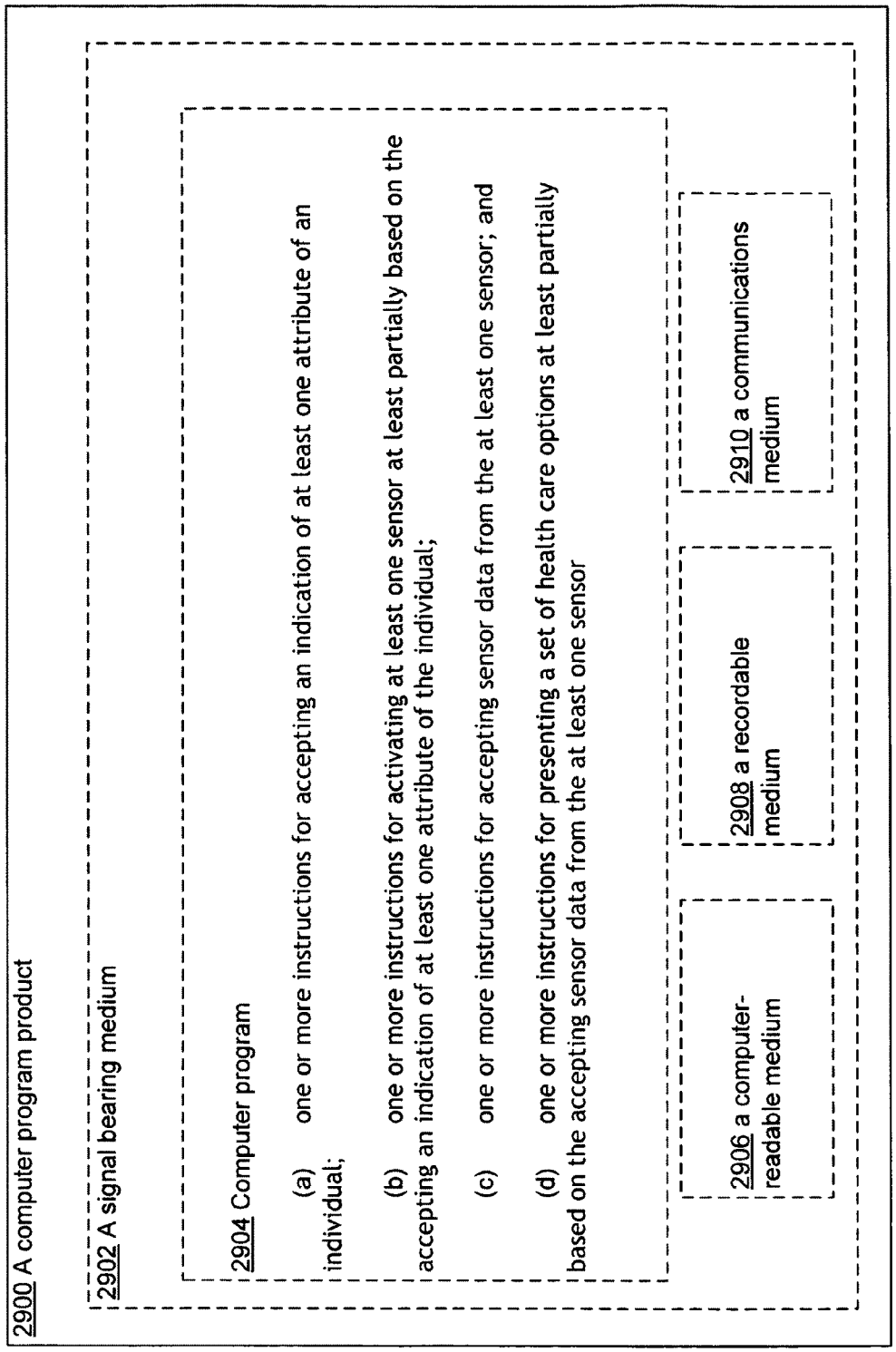
FIG. 29 illustrates a partial view of an example article of manufacture including a computer program product that includes a computer program for executing a computer process on a computing device related to health services planning and matching, which may serve as a context for introducing one or more processes and/or devices described herein.

FIG. 29 illustrates a partial view of an example computer program product 2900 that includes a computer program 2904 for executing a computer process on a computing device. An embodiment of the example computer program product 2900 is provided using a signal-bearing medium 2902, and may include one or more instructions for accepting an indication of at least one attribute of an individual, one or more instructions for activating at least one sensor at least partially based on the accepting an indication of at least one attribute of the individual, one or more instructions for accepting sensor data from the at least one sensor, and one or more instructions for presenting a set of health care options at least partially based on the accepting sensor data from the at least one sensor. The one or more instructions may be, for example, computer executable and/or logic-implemented instructions. In one implementation, the signal-bearing medium 2902 may include a computer-readable medium 2906. In one implementation, the signal bearing medium 2902 may include a recordable medium 2908. In one implementation, the signal bearing medium 2902 may include a communications medium 2910.

FIG. 30 illustrates an example system 3000 in which embodiments may be implemented. The system 3000 includes a computing system environment. The system 3000 also illustrates the user 118 using a device 3004, which is optionally shown as being in communication with a computing device 3002 by way of an optional coupling 3006. The optional coupling 3006 may represent a local, wide-area, or peer-to-peer network, or may represent a bus that is internal to a computing device (e.g., in example embodiments in which the computing device 3002 is contained in whole or in part within the device 3004). A storage medium 3008 may be any computer storage media.

The computing device 3002 includes computer-executable instructions 3010 that when executed on the computing device 3002 cause the computing device 3002 to accept an indication of at least one attribute of an individual, activate at least one sensor at least partially based on the accepting an indication of at least one attribute of the individual, accept sensor data from the at least one sensor, and present a set of health care options at least partially based on the accepting sensor data from the at least one sensor. As referenced above and as shown in FIG. 30, in some examples, the computing device 3002 may optionally be contained in whole or in part within the device 3004.

In FIG. 30, then, the system 3000 includes at least one computing device (e.g., 3002 and/or 3004). The computer-executable instructions 3010 may be executed on one or more of the at least one computing device. For example, the computing device 3002 may implement the computer-executable instructions 3010 and output a result to (and/or receive data from) the computing device 3004. Since the computing device 3002 may be wholly or partially contained within the computing device 3004, the device 3004 also may be said to execute some or all of the computer-executable instructions 3010, in order to be caused to perform or implement, for example, various ones of the techniques described herein, or other techniques.

The device 3004 may include, for example, a portable computing device, workstation, or desktop computing device. In another example embodiment, the computing device 3002 is operable to communicate with the device 3004 associated with the user 118 to receive information about the input from the user 118 for performing data access and data processing and presenting an output of the user-health test function at least partly based on the user data.

Although a user 140 is shown/described herein as a single illustrated figure, those skilled in the art will appreciate that a user 140 may be representative of a human user, a robotic user (e.g., computational entity), and/or substantially any combination thereof (e.g., a user may be assisted by one or more robotic agents). In addition, a user 140, as set forth herein, although shown as a single entity may in fact be composed of two or more entities. Those skilled in the art will appreciate that, in general, the same may be said of "sender" and/or other entity-oriented terms as such terms are used herein.

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures suitable to operation. Electronic circuitry, for example, may manifest one or more paths of electrical current constructed and arranged to implement various logic functions as described herein. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory.

Further, implementation of at least part of a system for performing a method in one territory does not preclude use of the system in another territory.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A atone, B atone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A mobile computing device, comprising:
   circuitry configured for accepting at least one indication of at least one attribute of at least one individual via at least one user interface of the mobile computing device;
   circuitry configured for activating at least one image sensor of the mobile computing device at least partially based on the accepting at least one indication of at least one attribute of at least one individual;
   circuitry configured for accepting at least some sensor data from the at least one image sensor of the mobile computing device, the at least some sensor data including at least one or more images of at least a portion of a face of the user;
   circuitry configured for matching, at least partially via at least one search conducted at least partially using at least one wireless transmission by the mobile computing device via at least one communications network, the at least some sensor data from the at least one image sensor with one or more health-related services options to obtain a set of health care options for presentation to the at least one individual, including at least transmitting an indication of one or more conditions of the at least one individual ascertained by the mobile computing device at least partially based on the one or more images of the at least a portion of the face of the user as a search term to obtain the set of health care options for presentation to the at least one individual; and
   circuitry configured for presenting the set of health care options to the at least one individual via the mobile computing device at least partially based on the matching the at least some sensor data from the at least one image sensor.

2. The mobile computing device of claim 1, wherein circuitry configured for accepting at least one indication of at least one attribute of at least one individual via at least one user interface of the mobile computing device comprises:
   circuitry configured for accepting at least one physical attribute associated with the at least one individual.

3. The mobile computing device of claim 2, wherein circuitry configured for accepting at least one physical attribute associated with the at least one individual comprises:
   circuitry configured for accepting at least one physical symptom associated with the at least one individual.

4. The mobile computing device of claim 3, wherein circuitry configured for accepting at least one physical symptom associated with the at least one individual comprises:
   circuitry configured for accepting one or more of at least one indication or at least one measurement of one or more of pain, hypertension, sweating, dizziness, lightheadedness, abnormal respiration, headache, fatigue, nausea, fever, abnormal heart rhythm, motor weakness, or abnormal heart rate.

5. The mobile computing device of claim 2, wherein circuitry configured for accepting at least one indication of at least one physical attribute associated with the at least one individual comprises:
    circuitry configured for accepting at least one indication of at least one physical diagnosis associated with the at least one individual.

6. The mobile computing device of claim 5, wherein circuitry configured for accepting at least one indication of at least one physical diagnosis associated with at least one individual comprises:
    circuitry configured for accepting at least one diagnosis of one or more of at least one cardiovascular disorder, at least one digestive disorder, at least one endocrine disorder, at least one hearing disorder, at least one immune disorder, at least one inner ear disorder, at least one integumentary disorder, at least one lymphatic disorder, at least one muscular disorder, at least one nervous system disorder, at least one reproductive disorder, at least one respiratory disorder, at least one skeletal disorder, at least one visual disorder, or at least one urinary disorder.

7. The mobile computing device of claim 1, wherein circuitry configured for accepting at least one indication of at least one attribute of at least one individual via at least one user interface of the mobile computing device comprises:
    circuitry configured for accepting one or more of at least one current treatment or at least one proposed treatment associated with the at least one individual.

8. The mobile computing device of claim 1, wherein circuitry configured for accepting at least one indication of at least one attribute of at least one individual via at least one user interface of the mobile computing device comprises:
    circuitry configured for accepting the at least one indication of the at least one attribute from at least one medical history associated with the at least one individual, a location of the at least one medical history associated with the at least one individual provided via the at least one user interface of the mobile computing device.

9. The mobile computing device of claim 1, wherein circuitry configured for accepting at least one indication of at least one attribute of at least one individual via at least one user interface of the mobile computing device comprises:
    circuitry configured for accepting the at least one indication of the at least one attribute from at least one personal medical history associated with the at least one individual, a location of the at least one personal medical history associated with the at least one individual provided via the at least one user interface of the mobile computing device.

10. The mobile computing device of claim 1, wherein circuitry configured for accepting at least one indication of at least one attribute of at least one individual via at least one user interface of the mobile computing device comprises:
    circuitry configured for accepting the at least one indication of the at least one attribute from at least one family medical history associated with the at least one individual, a location of the at least one family medical history associated with the at least one individual provided via the at least one user interface of the mobile computing device; and
    circuitry configured for signaling to evaluate the at least one individual for at least one condition indicated by the at least one attribute from the at least one family medical history via activating the at least one sensor.

11. The mobile computing device of claim 1, wherein circuitry configured for accepting at least one indication of at least one attribute of at least one individual via at least one user interface of the mobile computing device comprises:
    circuitry configured for accepting at least one indication of at least one mental attribute associated with the at least one individual.

12. The mobile computing device of claim 11, wherein circuitry configured for accepting at least one indication of at least one mental attribute associated with the at least one individual comprises:
    circuitry configured for accepting at least one indication of at least one mental symptom associated with the at least one individual.

13. The mobile computing device of claim 12, wherein circuitry configured for accepting at least one indication of at least one mental symptom associated with the at least one individual comprises:
    circuitry configured for accepting at least one indication of at least one of at least one anxiety attribute, at least one appearance, at least one behavior, at least one depression attribute, at least one fear, at least one inattention attribute, at least one mood disturbance, at least one phobia, or at least one psychological test result.

14. The mobile computing device of claim 11, wherein circuitry configured for accepting at least one indication of at least one mental attribute associated with the at least one individual comprises:
    circuitry configured for accepting at least one measurement associated with at least one of brain activity, cardiac activity, vascular activity, peripheral neural signals, hemodynamic activity, or metabolic activity.

15. The mobile computing device of claim 11, wherein circuitry configured for accepting at least one indication of at least one mental attribute associated with the at least one individual comprises:
    circuitry configured for accepting at least one indication of at least one mental impairment associated with the at least one individual.

16. The mobile computing device of claim 15, wherein circuitry configured for accepting at least one indication of at least one mental impairment associated with the at least one individual comprises:
    circuitry configured for accepting at least one indication of one or more of at least one mood disorder, at least one anxiety disorder, at least one psychotic disorder, at least one eating disorder, at least one developmental disorder, at least one phobia, at least one communication disorder, at least one social disorder, or at least one personality disorder.

17. The mobile computing device of claim 11, wherein circuitry configured for accepting at least one indication of at least one mental attribute associated with the at least one individual comprises:
    circuitry configured for accepting at least one indication of at least one mental diagnosis associated with the at least one individual.

18. The mobile computing device of claim 17, wherein circuitry configured for accepting at least one indication of at least one mental diagnosis associated with the at least one individual comprises:
    circuitry configured for accepting at least one indication of one or more of at least one depression condition, at least one phobia, at least one anxiety disorder, at least one personality disorder, at least one psychotic disorder, at least one developmental disorder, at least one panic disorder, at least one bipolar disorder, at least one schizophrenia condition, at least one eating disorder, at least one obsessive compulsive disorder, at least one post traumatic stress disorder, at least one attentional disorder, at least one communication disorder, at least one social disorder, or at least one mood disorder.

19. The mobile computing device of claim 1, wherein circuitry configured for accepting at least one indication of at least one attribute of at least one individual via at least one user interface of the mobile computing device comprises:
 circuitry configured for accepting at least one indication of at least one past mental therapy associated with the at least one individual.

20. The mobile computing device of claim 1, wherein circuitry configured for activating at least one image sensor of the mobile computing device at least partially based on the accepting at least one indication of at least one attribute of at least one individual comprises:
 circuitry configured for activating at least one sensor at least partially based on a physiological condition.

21. The mobile computing device of claim 1, wherein circuitry configured for activating at least one image sensor of the mobile computing device at least partially based on the accepting at least one indication of at least one attribute of at least one individual comprises:
 circuitry configured for activating at least one sensor at least partially based on at least one of pain, hypertension, sweating, dizziness, lightheadedness, abnormal respiration, headache, fatigue, nausea, fever, abnormal heart rhythm, motor weakness, or abnormal heart rate.

22. The mobile computing device of claim 1, wherein circuitry configured for activating at least one image sensor of the mobile computing device at least partially based on the accepting at least one indication of at least one attribute of at least one individual comprises:
 circuitry configured for activating at least one image sensor of the mobile computing device and activating at least one non-invasive sensor at least partially based on the accepting at least one indication of at least one attribute of the at least one individual.

23. The mobile computing device of claim 22, wherein circuitry configured for activating at least one image sensor of the mobile computing device and activating at least one non-invasive sensor at least partially based on the accepting at least one indication of at least one attribute of the at least one individual comprises:
 circuitry configured for activating at least one wireless sensor at least partially based on the accepting at least one indication of at least one attribute of the at least one individual.

24. The mobile computing device of claim 1, wherein circuitry configured for activating at least one image sensor of the mobile computing device at least partially based on the accepting at least one indication of at least one attribute of at least one individual comprises:
 circuitry configured for activating at least one image sensor of the mobile computing device and activating one or more of at least one invasive sensor or at least one partially invasive sensor at least partially based on the accepting at least one indication of at least one attribute of the at least one individual.

25. The mobile computing device of claim 1, wherein circuitry configured for activating at least one image sensor of the mobile computing device at least partially based on the accepting at least one indication of at least one attribute of at least one individual comprises:
 circuitry configured for activating at least one image sensor of the mobile computing device and activating at least one time sensor in association with one or more of at least one specified time or at least one specified time interval.

26. The mobile computing device of claim 1, wherein circuitry configured for accepting at least some sensor data from the at least one image sensor of the mobile computing device, the at least some sensor data including at least one or more images of at least a portion of a face of the user comprises:
 circuitry configured for accepting at least some sensor data from the at least one image sensor of the mobile computing device and accepting at least some brain sensor data from at least one brain sensor.

27. The mobile computing device of claim 26, wherein circuitry configured for accepting at least some sensor data from the at least one image sensor of the mobile computing device and accepting at least some brain sensor data from at least one brain sensor comprises:
 circuitry configured for accepting at least some sensor data from the at least one image sensor of the mobile computing device and accepting at least some data from at least one neuroprosthetic.

28. The mobile computing device of claim 26, wherein circuitry configured for accepting at least some sensor data from the at least one image sensor of the mobile computing device and accepting at least some brain sensor data from at least one brain sensor comprises:
 circuitry configured for accepting at least some sensor data from the at least one image sensor of the mobile computing device and accepting at least some data from at least one brain-computer interface.

29. The mobile computing device of claim 28, wherein circuitry configured for accepting at least some sensor data from the at least one image sensor of the mobile computing device and accepting at least some data from at least one brain-computer interface comprises:
 circuitry configured for accepting at least some sensor data from the at least one image sensor of the mobile computing device and accepting at least some data from at least one electrocorticography electrode.

30. The mobile computing device of claim 1, wherein circuitry configured for accepting at least some sensor data from the at least one image sensor of the mobile computing device, the at least some sensor data including at least one or more images of at least a portion of a face of the user comprises:
 circuitry configured for accepting at least some sensor data including at least one or more images that include at least one skin portion of the face of the user for detecting at least one skin response to at least one stimulus.

31. The mobile computing device of claim 26, wherein circuitry configured for accepting at least some sensor data from the at least one image sensor of the mobile computing device and accepting at least some brain sensor data from at least one brain sensor comprises:
 circuitry configured for accepting at least some sensor data from the at least one image sensor of the mobile computing device and accepting at least one neurophysiological measurement using at least one of electroencephalography, computed axial tomography, positron emission tomography, magnetic resonance imaging, functional magnetic resonance imaging, functional near-infrared imaging, or magnetoencephalography.

32. The mobile computing device of claim 1, wherein circuitry configured for accepting at least some brain sensor data from the at least one image sensor of the mobile computing device, the at least some sensor data including at least one or more images of at least a portion of a face of the user comprises:

circuitry configured for accepting at least one brain activity surrogate marker identifiable via the at least one or more images of at least a portion of a face of the user.

33. The mobile computing device of claim 32, wherein circuitry configured for accepting at least one brain activity surrogate marker identifiable via the at least one or more images of at least a portion of a face of the user comprises:

circuitry configured for accepting one or more of iris dilation, iris constriction, or gaze tracking.

34. The mobile computing device of claim 1, wherein circuitry configured for accepting at least some sensor data from the at least one image sensor of the mobile computing device, the at least some sensor data including at least one or more images of at least a portion of a face of the user comprises:

circuitry configured for accepting at least some sensor data including at least one or more images that include at least one portion of at least one eye of the user.

35. The mobile computing device of claim 1, wherein circuitry configured for accepting at least some sensor data from the at least one image sensor of the mobile computing device, the at least some sensor data including at least one or more images of at least a portion of a face of the user comprises:

circuitry configured for accepting at least some sensor data from the at least one image sensor of the mobile computing device including at least one or more images depicting a face pattern of the user.

36. The mobile computing device of claim 1, wherein circuitry configured for presenting the set of health care options to the at least one individual via the mobile computing device at least partially based on the matching the at least some sensor data from the at least one image sensor comprises:

circuitry configured for presenting the set of health care options at least partially based on at least one user preference.

37. The mobile computing device of claim 36, wherein circuitry configured for presenting the set of health care options at least partially based on at least one user preference comprises:

circuitry configured for presenting the set of health care options at least partially based on one or more of at least one location preference or at least one time frame preference.

38. The mobile computing device of claim 36, wherein circuitry configured for presenting the set of health care options at least partially based on at least one user preference comprises:

circuitry configured for presenting the set of health care options at least partially based on at least one health care provider compatible with one or more of at least one payment capacity of the at least one individual or at least one payment capacity of at least one user.

39. The mobile computing device of claim 1, wherein circuitry configured for presenting the set of health care options to the at least one individual via the mobile computing device at least partially based on the matching the at least some sensor data from the at least one image sensor comprises:

circuitry configured for presenting the set of health care options at least partially based on one or more of at least one standard of care, at least one expert opinion, at least one insurance company evaluation, or at least some research data.

40. The mobile computing device of claim 1, wherein circuitry configured for matching, at least partially via at least one search conducted at least partially using at least one wireless transmission by the mobile computing device via at least one communications network, the at least some sensor data from the at least one image sensor with one or more health-related services options to obtain a set of health care options for presentation to the at least one individual, including at least transmitting an indication of one or more conditions of the at least one individual ascertained by the mobile computing device at least partially based on the one or more images of the at least a portion of the face of the user as a search term to obtain the set of health care options for presentation to the at least one individual comprises:

circuitry configured for using at least one third party reference accessible via the at least one communications network to obtain the set of health care options.

41. The mobile computing device of claim 40, wherein circuitry configured for using at least one third party reference accessible via the communications network to obtain the set of health care options comprises:

circuitry configured for using one or more of at least one search engine, at least one Deep Web search program, at least one web crawler, at least one online database, or at least one online directory to obtain the set of health care options.

42. The mobile computing device of claim 1, wherein circuitry configured for accepting at least one indication of at least one attribute of at least one individual via at least one user interface of the mobile computing device comprises:

circuitry configured for accepting at least one indication of at least one attribute related to mood of at least one individual, the at least one attribute related to mood including one or more of at least one attribute related to anxiety or at least one attribute related to depression.

43. The mobile computing device of claim 1, further comprising:

circuitry configured for accepting at least one indication of at least one selection of at least one health care option by the at least one individual; and circuitry configured for transmitting, at least partially via the at least one communications network, at least one electronic solicitation for one or more bids from one or more potential service providers for provision of the at least one health care option selected by the at least one individual.

44. A method for a mobile computing device, comprising:

accepting at least one indication of at least one attribute of at least one individual via at least one user interface of the mobile computing device;

activating at least one image sensor of the mobile computing device at least partially based on the accepting at least one indication of at least one attribute of at least one individual;

accepting at least some sensor data from the at least one image sensor of the mobile computing device, the at least some sensor data including at least one or more images of at least a portion of a face of the user;

matching, at least partially via at least one search conducted at least partially using at least one wireless transmission by the mobile computing device via at least one communications network, the at least some sensor data from the at least one image sensor with one or more health-related services options to obtain a set of health care options for presentation to the at least one individual, including at least transmitting an indication of one or more conditions of the at least one individual ascertained by the mobile computing device at least partially based on the one or more images of the at least a portion of the face of the user as a search term to obtain the set of health care options for presentation to the at least one individual; and presenting the set of health care options to the at least one individual via the mobile computing device at least partially based on the matching the at least some sensor data from the at least one image sensor, wherein at least one of the accepting, activating, matching, or presenting is at least partially implemented using at least one processing device.

45. A computer program product for a mobile computing device, comprising:
at least one non-transitory computer-readable medium including at least:
one or more instructions for accepting at least one indication of at least one attribute of at least one individual;
one or more instructions for activating at least one sensor at least partially based on the accepting at least one indication of at least one attribute of at least one individual via at least one user interface of the mobile computing device;
one or more instructions for activating at least one image sensor of the mobile computing device at least partially based on the accepting at least one indication of at least one attribute of at least one individual;
one or more instructions for matching, at least partially via at least one search conducted at least partially using at least one wireless transmission by the mobile computing device via at least one communications network, the at least some sensor data from the at least one image sensor with one or more health-related services options to obtain a set of health care options for presentation to the at least one individual, including at least transmitting an indication of one or more conditions of the at least one individual ascertained by the mobile computing device at least partially based on the one or more images of the at least a portion of the face of the user as a search term to obtain the set of health care options for presentation to the at least one individual; and
one or more instructions for presenting the set of health care options to the at least one individual via the mobile computing device at least partially based on the matching the at least some sensor data from the at least one image sensor.

46. The mobile computing device of claim 1, wherein circuitry configured for accepting at least one indication of at least one attribute of at least one individual via at least one user interface of the mobile computing device comprises:
circuitry configured for accepting at least one individual's input regarding at least one series of epileptic seizures; and
wherein circuitry configured for activating at least one image sensor of the mobile computing device at least partially based on the accepting at least one indication of at least one attribute of at least one individual includes at least:
circuitry configured for activating the at least one image sensor of the mobile computing device for detection of at least one brain activity surrogate marker; and
wherein circuitry configured for accepting at least some sensor data from the at least one image sensor of the mobile computing device, the at least some sensor data including at least one or more images of at least a portion of a face of the user includes at least:
circuitry configured for accepting at least one brain activity surrogate marker determined at least partially from one or more images of the at least a portion of the face of the user captured via the at least one image sensor of the mobile computing device;
wherein circuitry configured for matching, at least partially via at least one search conducted at least partially using at least one wireless transmission by the mobile computing device via at least one communications network, the at least some sensor data from the at least one image sensor with one or more health-related services options to obtain a set of health care options for presentation to the at least one individual, including at least transmitting an indication of one or more conditions of the at least one individual ascertained by the mobile computing device at least partially based on the one or more images of the at least a portion of the face of the user as a search term to obtain the set of health care options for presentation to the at least one individual includes at least:
circuitry configured for matching, at least partially via at least one search conducted via at least one communications network, the at least one brain activity surrogate marker with at least one set of epilepsy medications and at least one set of physicians specializing in treating epilepsy to obtain a set of health care options for presentation to the at least one individual; and
wherein circuitry configured for presenting the set of health care options to the at least one individual via the mobile computing device at least partially based on the matching the at least some sensor data from the at least one image sensor includes at least:
circuitry configured for presenting at least one set of epilepsy medications and at least one set of physicians specializing in treating epilepsy matching the at least one individual's input regarding at least one series of epileptic seizures and matching the at least one activity surrogate marker.

47. The mobile computing device of claim 1, wherein circuitry configured for accepting at least one indication of at least one attribute of at least one individual via at least one user interface of the mobile computing device comprises:
circuitry configured for accepting at least one individual's input regarding at least one personal medical history, a location of the at least one personal medical history associated with the at least one individual provided by the at least one individual via the at least one user interface of the mobile computing device; and
wherein circuitry configured for activating at least one image sensor of the mobile computing device at least partially based on the accepting at least one indication of at least one attribute of at least one individual includes at least:
circuitry configured for activating at least one image sensor of the mobile computing device at least partially based on the accepting at least one individual's input regarding at least one personal medical history to determine at least one subpopulation to which the at least one individual belongs at least partially based on one or more images of the at least one individual captured via the at least one image sensor of the mobile computing device; and wherein circuitry configured for presenting the set of health care options to the at least one individual via the mobile computing device at least partially based on the matching the at least some sensor data from the at least one image sensor includes at least:

circuitry configured for presenting, in response to accepting at least some image data from the at least one image sensor of the mobile device indicative of at least one subpopulation to which the at least one individual belongs, a set of health care options at least partially based on a search of at least one reference database using the at least one subpopulation to which the at least one individual belongs as a search term.

48. The mobile computing device of claim 1, wherein circuitry configured for presenting the set of health care options to the at least one individual via the mobile computing device at least partially based on the matching the at least some sensor data from the at least one image sensor comprises:

circuitry configured for filtering one or more health care options at least partially based on (i) at least one treatment goal of the at least one individual, (ii) at least one preference of the at least one individual relating to treatment modality, and (iii) at least one payment capacity associated with the at least one individual; and circuitry configured for presenting (a) at least one health care option remaining subsequent to filtering the one or more health care options and (b) at least one historical result corresponding with the at least one health care option remaining subsequent to filtering the one or more health care options.

49. The mobile computing device of claim 1, wherein circuitry configured for accepting at least some sensor data from the at least one image sensor of the mobile computing device, the at least some sensor data including at least one or more images of at least a portion of a face of the user comprises:

circuitry configured for causing the mobile computing device to prompt the at least one individual to focus on a visual target on a display of the mobile computing device;

circuitry configured for rendering the visual target via the display of the mobile computing device;

circuitry configured for causing the visual target to move forward and backward on the display of the computing device;

circuitry configured for monitoring at least one of pupil size or pupil position of the at least one individual while causing the visual target to move forward and backward on the display of the computing device; and circuitry configured for providing at least some monitored data as the indication of one or more conditions of the at least one individual ascertained by the mobile computing device for subsequent transmission in association with the at least one search.

50. The mobile computing device of claim 1, wherein circuitry configured for matching, at least partially via at least one search conducted at least partially using at least one wireless transmission by the mobile computing device via at least one communications network, the at least some sensor data from the at least one image sensor with one or more health-related services options to obtain a set of health care options for presentation to the at least one individual, including at least transmitting an indication of one or more conditions of the at least one individual ascertained by the mobile computing device at least partially based on the one or more images of the at least a portion of the face of the user as a search term to obtain the set of health care options for presentation to the at least one individual comprises:

circuitry configured for ascertaining the indication of one or more conditions of the at least one individual at least partially based on the one or more images of the at least a portion of the face of the user as a search term at least partially via comparing at least one of the one or more images of the at least a portion of the face of the user with at least one image of the at least one individual captured previously.

51. The mobile computing device of claim 50, wherein circuitry configured for ascertaining the indication of one or more conditions of the at least one individual at least partially based on the one or more images of the at least a portion of the face of the user as a search term at least partially via comparing at least one of the one or more images of the at least a portion of the face of the user with at least one image of the at least one individual captured previously comprises:

circuitry configured for monitoring progress of an anatomical feature of the at least one individual at least partially based on the at least one image of the at least one individual captured previously and the at least one of the one or more images of the at least a portion of the face of the user captured via the image sensor of the mobile computing device; and circuitry configured for providing an indication of the progress of the anatomical feature of the at least one individual ascertained by the mobile computing device for subsequent transmission in association with the at least one search.

* * * * *

UNITED STATES PATENT AND TRADEMARK OFFICE
CERTIFICATE OF CORRECTION

PATENT NO. : 9,886,729 B2
APPLICATION NO. : 12/658256
DATED : February 6, 2018
INVENTOR(S) : Shawn P. Firminger et al.

It is certified that error appears in the above-identified patent and that said Letters Patent is hereby corrected as shown below:

In the Claims

At Column 54, Line 48, Claim 46, "one activity surrogate marker" should read --one brain activity surrogate marker--

Signed and Sealed this
Twenty-fifth Day of June, 2019

Andrei Iancu
*Director of the United States Patent and Trademark Office*